(12) United States Patent
Carson et al.

(10) Patent No.: US 7,547,307 B2
(45) Date of Patent: Jun. 16, 2009

(54) COMPUTER ASSISTED KNEE ARTHROPLASTY INSTRUMENTATION, SYSTEMS, AND PROCESSES

(75) Inventors: Christopher Patrick Carson, Collierville, TN (US); Crista Smothers, Cordova, TN (US); Christopher M. Lyons, Hernando, MS (US)

(73) Assignee: Smith & Nephew, Inc., Memphis, TN (US)

( * ) Notice: Subject to any disclaimer, the term of this patent is extended or adjusted under 35 U.S.C. 154(b) by 872 days.

(21) Appl. No.: 10/229,372

(22) Filed: Aug. 27, 2002

(65) Prior Publication Data

US 2003/0069591 A1    Apr. 10, 2003

Related U.S. Application Data

(60) Provisional application No. 60/355,899, filed on Feb. 11, 2002.

(51) Int. Cl.
*A61F 2/38* (2006.01)
(52) U.S. Cl. ............... 606/88; 606/87; 606/89
(58) Field of Classification Search ........ 606/53, 606/54, 57, 60, 66, 79, 82, 86–89
See application file for complete search history.

(56) References Cited

U.S. PATENT DOCUMENTS

| | | |
|---|---|---|
| 1,076,971 A | 10/1913 | Geiger |
| 1,201,467 A | 10/1916 | Hoglund |
| 2,092,869 A | 9/1937 | Baum |
| 3,412,733 A | 11/1968 | Ross |
| 3,457,922 A | 7/1969 | Ray |
| 3,702,611 A | 11/1972 | Fishbein |
| 4,305,394 A | 12/1981 | Bertuch, Jr. |
| 4,323,080 A | 4/1982 | Melharty |
| 4,421,112 A | 12/1983 | Mains et al. |
| 4,456,010 A | 6/1984 | Reimels et al. |
| 4,457,307 A | 7/1984 | Stillwell |
| 4,483,554 A | 11/1984 | Ernst |

(Continued)

FOREIGN PATENT DOCUMENTS

DE    42 25 112 C    12/1993

(Continued)

OTHER PUBLICATIONS

Search Evolution Total Knee System—Relax—B. Braun Melsungen AG website http://www.orthopilot.com/index.cfm?uuid=26EA6AA4838D495B8A895420A83BD099&obj (3 pages, Sep. 2, 2003).

(Continued)

*Primary Examiner*—Michael J. Hayes
*Assistant Examiner*—Michael G. Mendoza
(74) *Attorney, Agent, or Firm*—Kilpatrick Stockton LLP

(57) ABSTRACT

Instrumentation, systems, and processes for tracking anatomy, instrumentation, trial implants, implants, and references, and rendering images and data related to them in connection with surgical operations, for example total knee arthroplasties ("TKA"). These instrumentation, systems, and processes are accomplished by using a computer to intraoperatively obtain images of body parts and to register, navigate, and track surgical instruments. Disclosed in this document are also alignment modules and other structures and processes which allow for coarse and fine alignment of instrumentation and other devices relative to bone for use in connection with the tracking systems of the present invention.

22 Claims, 75 Drawing Sheets

U.S. PATENT DOCUMENTS

| | | |
|---|---|---|
| 4,524,766 A | 6/1985 | Petersen |
| 4,534,364 A | 8/1985 | Lamoreux |
| 4,565,192 A | 1/1986 | Shapiro |
| 4,566,448 A | 1/1986 | Rohr, Jr. |
| 4,567,885 A | 2/1986 | Androphy |
| 4,567,886 A | 2/1986 | Petersen |
| 4,574,794 A | 3/1986 | Cooke et al. |
| 4,671,275 A | 6/1987 | Deyerle |
| 4,703,751 A | 11/1987 | Pohl |
| 4,712,951 A | 12/1987 | Brown |
| 4,718,413 A | 1/1988 | Johnson |
| 4,722,056 A | 1/1988 | Roberts et al. |
| 4,738,256 A | 4/1988 | Freeman et al. |
| 4,759,350 A | 7/1988 | Dunn et al. |
| 4,768,504 A | 9/1988 | Ender |
| 4,777,942 A | 10/1988 | Frey et al. |
| 4,802,468 A | 2/1989 | Powlan |
| 4,803,976 A | 2/1989 | Frigg et al. |
| 4,809,689 A | 3/1989 | Anapliotis |
| 4,815,899 A | 3/1989 | Regan |
| 4,875,475 A | 10/1989 | Comte et al. |
| 4,892,093 A | 1/1990 | Zarnowski et al. |
| 4,913,163 A | 4/1990 | Roger et al. |
| 4,938,762 A | 7/1990 | Wehrli |
| 4,952,213 A | 8/1990 | Bowman et al. |
| 4,964,862 A | 10/1990 | Arms |
| 5,002,545 A | 3/1991 | Whiteside et al. |
| 5,002,578 A | 3/1991 | Luman |
| 5,037,423 A | 8/1991 | Kenna |
| 5,049,149 A | 9/1991 | Schmidt |
| 5,053,039 A | 10/1991 | Hofmann et al. |
| 5,078,719 A | 1/1992 | Schreiber |
| 5,092,869 A | 3/1992 | Waldron |
| 5,098,426 A | 3/1992 | Sklar et al. |
| 5,116,338 A | 5/1992 | Poggie et al. |
| 5,122,144 A | 6/1992 | Bert et al. |
| 5,129,909 A | 7/1992 | Sutherland |
| 5,147,408 A | 9/1992 | Noble |
| 5,190,547 A | 3/1993 | Barber, Jr. et al. |
| 5,213,312 A | 5/1993 | MacDonald |
| 5,217,499 A | 6/1993 | Shelley |
| 5,230,338 A * | 7/1993 | Allen et al. .................. 600/429 |
| 5,246,444 A | 9/1993 | Schreiber |
| 5,254,119 A | 10/1993 | Schreiber |
| 5,263,972 A | 11/1993 | Evans et al. |
| 5,289,826 A | 3/1994 | Kovacevic |
| 5,305,203 A | 4/1994 | Raab |
| 5,342,366 A | 8/1994 | Whiteside et al. |
| 5,534,366 A | 8/1994 | Whiteside |
| 5,360,016 A | 11/1994 | Kovacevic |
| 5,364,401 A | 11/1994 | Ferrante et al. |
| 5,364,402 A | 11/1994 | Mumme et al. |
| 5,365,996 A | 11/1994 | Crook |
| 5,375,588 A | 12/1994 | Yoon |
| 5,379,133 A | 1/1995 | Kirk |
| 5,383,454 A | 1/1995 | Bucholz |
| 5,387,218 A | 2/1995 | Meswania et al. |
| 5,389,101 A | 2/1995 | Heilbrun et al. |
| 5,395,376 A | 3/1995 | Caspari et al. |
| 5,403,320 A | 4/1995 | Luman |
| 5,423,828 A | 6/1995 | Benson |
| 5,425,355 A | 6/1995 | Kulick |
| 5,445,166 A | 8/1995 | Taylor |
| 5,445,642 A | 8/1995 | McNulty et al. |
| 5,449,360 A | 9/1995 | Schreiber |
| 5,452,407 A | 9/1995 | Crook |
| 5,462,548 A | 10/1995 | Pappas et al. |
| 5,462,549 A | 10/1995 | Glock |
| 5,468,244 A | 11/1995 | Attfield et al. |
| 5,470,354 A | 11/1995 | Hershberger et al. |
| 5,474,559 A | 12/1995 | Bertin et al. |
| 5,484,437 A | 1/1996 | Michelson |
| 5,486,178 A | 1/1996 | Hodge |
| 5,490,854 A | 2/1996 | Fisher et al. |
| 5,491,510 A | 2/1996 | Gove |
| 5,507,824 A | 4/1996 | Lennox |
| 5,514,139 A | 5/1996 | Goldstein et al. |
| 5,517,990 A | 5/1996 | Kalfas et al. |
| 5,527,316 A | 6/1996 | Williamson |
| 5,540,691 A | 7/1996 | Elstrom et al. |
| 5,540,694 A | 7/1996 | DeCarlo, Jr. |
| 5,540,695 A | 7/1996 | Levy |
| 5,540,696 A | 7/1996 | Booth, Jr. et al. |
| 5,569,260 A | 10/1996 | Petersen |
| 5,597,379 A | 1/1997 | Haines et al. |
| 5,598,269 A | 1/1997 | Kitaevich et al. |
| 5,603,318 A | 2/1997 | Heilbrun et al. |
| 5,613,969 A | 3/1997 | Jenkins, Jr. |
| 5,643,268 A | 7/1997 | Vilsmeier et al. |
| 5,643,272 A | 7/1997 | Haines et al. |
| 5,658,290 A | 8/1997 | Lechot |
| 5,669,914 A | 9/1997 | Eckhoff |
| 5,676,668 A | 10/1997 | McCue et al. |
| 5,681,316 A | 10/1997 | DeOrio et al. |
| 5,682,886 A | 11/1997 | Delp et al. |
| 5,683,397 A | 11/1997 | Vendrely et al. |
| 5,688,279 A | 11/1997 | McNulty et al. |
| 5,693,056 A | 12/1997 | Carls et al. |
| 5,695,501 A * | 12/1997 | Carol et al. .................. 606/130 |
| 5,702,406 A | 12/1997 | Vilsmeier et al. |
| 5,704,941 A | 1/1998 | Jacober et al. |
| 5,707,370 A * | 1/1998 | Berki et al. .................... 606/59 |
| 5,709,689 A | 1/1998 | Ferrante et al. |
| 5,715,836 A | 2/1998 | Kliegis et al. |
| 5,716,361 A | 2/1998 | Masini |
| 5,720,752 A | 2/1998 | Elliott et al. |
| 5,722,978 A | 3/1998 | Jenkins, Jr. |
| 5,733,292 A | 3/1998 | Gustilo et al. |
| 5,735,904 A | 4/1998 | Pappas |
| 5,743,915 A | 4/1998 | Bertin et al. |
| 5,748,767 A | 5/1998 | Raab |
| 5,755,725 A | 5/1998 | Druais |
| 5,755,803 A | 5/1998 | Haines et al. |
| 5,769,861 A | 6/1998 | Vilsmeier |
| 5,772,593 A | 6/1998 | Hakamata |
| 5,772,594 A | 6/1998 | Barrick |
| 5,776,064 A | 7/1998 | Kalfas et al. |
| 5,782,842 A | 7/1998 | Kloess et al. |
| 5,792,147 A | 8/1998 | Evans et al. |
| 5,797,924 A | 8/1998 | Schulte et al. |
| 5,799,055 A | 8/1998 | Peshkin et al. |
| 5,800,352 A | 9/1998 | Ferre et al. |
| 5,800,438 A | 9/1998 | Tuke et al. |
| 5,807,252 A | 9/1998 | Hassfeld et al. |
| 5,810,827 A | 9/1998 | Haines et al. |
| 5,810,841 A | 9/1998 | McNeirney et al. |
| 5,817,097 A | 10/1998 | Howard et al. |
| 5,830,214 A | 11/1998 | Flom et al. |
| 5,836,954 A | 11/1998 | Heilbrun et al. |
| 5,848,967 A | 12/1998 | Cosman |
| 5,850,836 A | 12/1998 | Steiger et al. |
| 5,860,981 A | 1/1999 | Bertin et al. |
| 5,865,809 A | 2/1999 | Moenning et al. |
| 5,871,018 A | 2/1999 | Delp et al. |
| 5,871,445 A | 2/1999 | Bucholz |
| 5,879,352 A | 3/1999 | Filoso et al. |
| 5,879,354 A | 3/1999 | Haines et al. |
| 5,880,976 A | 3/1999 | DiGioia III et al. |
| 5,885,296 A | 3/1999 | Masini |
| 5,885,297 A | 3/1999 | Matsen, III |
| 5,897,559 A | 4/1999 | Masinie |
| 5,916,221 A | 6/1999 | Hodorek et al. |
| 5,920,395 A | 7/1999 | Schulz |
| 5,921,992 A | 7/1999 | Costales et al. |

| | | | | | | |
|---|---|---|---|---|---|---|
| 5,925,049 | A | 7/1999 | Gustilo et al. | 6,258,095 B1 | 7/2001 | Lombardo et al. |
| 5,935,128 | A | 8/1999 | Carter et al. | 6,258,096 B1 | 7/2001 | Seki |
| 5,938,665 | A | 8/1999 | Martin | 6,264,647 B1 | 7/2001 | Lechot |
| 5,944,722 | A | 8/1999 | Masini | 6,283,971 B1 | 9/2001 | Temeles |
| 5,947,971 | A | 9/1999 | Kuslich et al. | 6,285,902 B1 | 9/2001 | Kienzle, III et al. |
| 5,947,973 | A | 9/1999 | Masini | 6,295,513 B1 | 9/2001 | Thackston |
| 5,951,561 | A | 9/1999 | Pepper et al. | 6,317,616 B1 | 11/2001 | Glossop |
| 5,957,926 | A | 9/1999 | Masini | 6,319,256 B1 | 11/2001 | Spotorno |
| 5,961,523 | A | 10/1999 | Masini | 6,332,891 B1 | 12/2001 | Himes |
| 5,971,989 | A | 10/1999 | Masini | 6,333,971 B2 | 12/2001 | McCrory et al. |
| 5,980,526 | A | 11/1999 | Johnson et al. | 6,344,853 B1 | 2/2002 | Knight |
| 5,980,535 | A | 11/1999 | Barnett et al. | 6,347,240 B1 | 2/2002 | Foley et al. |
| 5,999,837 | A | 12/1999 | Messner et al. | 6,351,659 B1 | 2/2002 | Vilsmeier |
| 6,001,106 | A | 12/1999 | Ryan et al. | 6,351,661 B1 | 2/2002 | Cosman |
| 6,002,859 | A | 12/1999 | DiGioia, III et al. | 6,377,839 B1 | 4/2002 | Kalfas et al. |
| 6,006,126 | A | 12/1999 | Cosman | 6,383,188 B2 | 5/2002 | Kuslich et al. |
| 6,007,537 | A | 12/1999 | Burkinshaw et al. | 6,385,475 B1 | 5/2002 | Cinquin et al. |
| 6,010,506 | A | 1/2000 | Gosney et al. | 6,405,072 B1 | 6/2002 | Cosman |
| 6,011,987 | A | 1/2000 | Barnett | 6,413,261 B1 | 7/2002 | Grundei |
| 6,016,606 | A | 1/2000 | Oliver et al. | 6,434,507 B1 | 8/2002 | Clayton et al. |
| 6,021,342 | A | 2/2000 | Brabrand | 6,440,140 B2 | 8/2002 | Bullivant et al. |
| 6,021,343 | A | 2/2000 | Foley et al. | 6,443,956 B1 | 9/2002 | Ray |
| 6,022,377 | A | 2/2000 | Nuelle et al. | 6,451,059 B1 | 9/2002 | Janas et al. |
| 6,026,315 | A | 2/2000 | Lenz et al. | 6,458,135 B1 | 10/2002 | Harwin et al. |
| 6,030,391 | A * | 2/2000 | Brainard et al. ............... 606/87 | 6,463,351 B1 | 10/2002 | Clynch |
| 6,033,410 | A | 3/2000 | McLean et al. | 6,468,202 B1 | 10/2002 | Irion et al. |
| 6,041,249 | A | 3/2000 | Regn | 6,477,400 B1 | 11/2002 | Barrick |
| 6,044,291 | A | 3/2000 | Rockseisen | 6,478,799 B1 | 11/2002 | Williamson |
| 6,045,556 | A | 4/2000 | Cohen | 6,490,467 B1 | 12/2002 | Bucholz et al. |
| 6,050,724 | A | 4/2000 | Schmitz et al. | 6,491,429 B1 | 12/2002 | Suhm |
| 6,053,922 | A | 4/2000 | Krause et al. | 6,491,702 B2 | 12/2002 | Heilbrun et al. |
| 6,056,756 | A | 5/2000 | Eng et al. | 6,503,249 B1 | 1/2003 | Krause |
| 6,068,633 | A | 5/2000 | Masini | 6,503,254 B2 | 1/2003 | Masini |
| 6,069,932 | A | 5/2000 | Peshkin et al. | 6,527,443 B1 | 3/2003 | Vilsmeier et al. |
| 6,073,044 | A | 6/2000 | Fitzpatrick et al. | 6,540,739 B2 | 4/2003 | Lechot |
| 6,077,269 | A | 6/2000 | Masini | 6,546,279 B1 | 4/2003 | Bova et al. |
| 6,081,336 | A | 6/2000 | Messner et al. | 6,551,319 B2 | 4/2003 | Lieberman |
| 6,083,163 | A | 7/2000 | Wegner et al. | 6,551,324 B2 | 4/2003 | Muller |
| 6,096,048 | A | 8/2000 | Howard et al. | 6,551,325 B2 | 4/2003 | Neubauer et al. |
| 6,102,916 | A | 8/2000 | Masini | 6,554,837 B1 | 4/2003 | Hauri et al. |
| 6,132,433 | A | 10/2000 | Whelan | 6,558,391 B2 | 5/2003 | Axelson, Jr. et al. |
| 6,143,390 | A | 11/2000 | Takamiya et al. | 6,558,421 B1 | 5/2003 | Fell et al. |
| 6,144,875 | A | 11/2000 | Schweikard et al. | 6,567,687 B2 | 5/2003 | Front et al. |
| 6,146,390 | A | 11/2000 | Heilbrun et al. | 6,574,493 B2 | 6/2003 | Rasche et al. |
| 6,148,280 | A | 11/2000 | Kramer | 6,595,997 B2 | 7/2003 | Axelson, Jr. et al. |
| 6,161,033 | A | 12/2000 | Kuhn | 6,602,259 B1 | 8/2003 | Masini |
| 6,162,190 | A | 12/2000 | Kramer | 6,620,268 B2 | 9/2003 | Cho et al. |
| 6,165,181 | A | 12/2000 | Heilbrun et al. | 6,640,127 B1 | 10/2003 | Kosaka et al. |
| 6,167,292 | A | 12/2000 | Badano et al. | 6,652,142 B2 | 11/2003 | Launay et al. |
| 6,167,295 | A | 12/2000 | Cosman | 6,662,036 B2 | 12/2003 | Cosman |
| 6,167,296 | A | 12/2000 | Shahidi | 6,673,077 B1 | 1/2004 | Katz |
| 6,168,627 | B1 | 1/2001 | Huebner | 6,685,711 B2 | 2/2004 | Axelson, Jr. et al. |
| 6,174,335 | B1 | 1/2001 | Varieur | 6,690,964 B2 | 2/2004 | Bieger et al. |
| 6,185,315 | B1 | 2/2001 | Schmucker et al. | 6,692,447 B1 | 2/2004 | Picard |
| 6,187,010 | B1 | 2/2001 | Masini | 6,695,848 B2 | 2/2004 | Haines |
| 6,190,320 | B1 | 2/2001 | Lelong | 6,702,821 B2 | 3/2004 | Bonutti |
| 6,190,395 | B1 | 2/2001 | Williams | 6,711,431 B2 | 3/2004 | Sarin et al. |
| 6,195,168 | B1 | 2/2001 | De Lega et al. | 6,712,823 B2 * | 3/2004 | Terrill-Grisoni et al. ...... 606/87 |
| 6,197,064 | B1 | 3/2001 | Haines et al. | 6,712,824 B2 | 3/2004 | Millard et al. |
| 6,198,794 | B1 | 3/2001 | Peshkin et al. | 6,716,249 B2 | 4/2004 | Hyde |
| 6,200,316 | B1 | 3/2001 | Zwirkoski et al. | 6,718,194 B2 | 4/2004 | Kienzle |
| 6,205,411 | B1 | 3/2001 | DiGioia, III et al. | 6,725,082 B2 | 4/2004 | Sati et al. |
| 6,211,976 | B1 | 4/2001 | Popovich et al. | 6,728,599 B2 | 4/2004 | Wang |
| 6,214,011 | B1 | 4/2001 | Masini | 6,772,026 B2 | 8/2004 | Bradbury et al. |
| 6,216,029 | B1 | 4/2001 | Paltieli | 6,780,190 B2 | 8/2004 | Maroney |
| 6,223,067 | B1 | 4/2001 | Vilsmeier et al. | 6,785,593 B2 | 8/2004 | Wang |
| 6,226,548 | B1 | 5/2001 | Foley et al. | 6,799,088 B2 | 9/2004 | Wang |
| 6,228,090 | B1 | 5/2001 | Waddell | 6,814,490 B1 | 11/2004 | Suhm et al. |
| 6,228,092 | B1 | 5/2001 | Mikhail | 6,827,723 B2 | 12/2004 | Carson |
| 6,235,038 | B1 | 5/2001 | Hunter et al. | 6,836,703 B2 | 12/2004 | Wang |
| 6,236,875 | B1 | 5/2001 | Bucholz et al. | 6,871,117 B2 | 3/2005 | Wang |
| 6,241,735 | B1 | 6/2001 | Marmulla | 6,882,982 B2 | 4/2005 | McMenimen |
| 6,249,581 | B1 | 6/2001 | Kok | 6,892,112 B2 | 5/2005 | Wang |

| | | |
|---|---|---|
| 6,905,514 B2 | 6/2005 | Carignan et al. |
| 6,923,817 B2 | 8/2005 | Carson |
| 6,947,786 B2 | 9/2005 | Simon et al. |
| 6,993,374 B2 | 1/2006 | Sasso |
| 7,001,346 B2 | 2/2006 | White |
| 7,035,702 B2 | 4/2006 | Jelonek et al. |
| 7,237,556 B2 | 7/2007 | Smothers |
| 7,241,298 B2 | 7/2007 | Nemec et al. |
| 2001/0001120 A1 | 5/2001 | Masini |
| 2001/0014772 A1 | 8/2001 | Lampotang et al. |
| 2001/0016745 A1 | 8/2001 | Bullivant et al. |
| 2001/0036245 A1 | 11/2001 | Kienzle, III et al. |
| 2001/0039421 A1 | 11/2001 | Heilbrun et al. |
| 2002/0002330 A1 | 1/2002 | Vilsmeier |
| 2002/0002365 A1 | 1/2002 | Lechot |
| 2002/0007294 A1 | 1/2002 | Bradbury et al. |
| 2002/0011594 A1 | 1/2002 | DeSouza |
| 2002/0016540 A1 | 2/2002 | Mikus et al. |
| 2002/0018981 A1 | 2/2002 | Andersson et al. |
| 2002/0029041 A1 | 3/2002 | Hover et al. |
| 2002/0032451 A1 | 3/2002 | Tierney et al. |
| 2002/0038085 A1 | 3/2002 | Immerz |
| 2002/0052606 A1 | 5/2002 | Bonutti |
| 2002/0065461 A1 | 5/2002 | Cosman |
| 2002/0068942 A1 | 6/2002 | Neubauer et al. |
| 2002/0072748 A1 | 6/2002 | Robioneck |
| 2002/0072821 A1 | 6/2002 | Baker |
| 2002/0077533 A1 | 6/2002 | Bieger et al. |
| 2002/0077540 A1 | 6/2002 | Kienzle, III |
| 2002/0085681 A1 | 7/2002 | Jensen |
| 2002/0087101 A1 | 7/2002 | Barrick et al. |
| 2002/0095081 A1 | 7/2002 | Vilsmeier |
| 2002/0102214 A1 | 8/2002 | Briley-Saebo et al. |
| 2002/0107518 A1 | 8/2002 | Neubauer et al. |
| 2002/0133161 A1 | 9/2002 | Axelson et al. |
| 2002/0133175 A1 | 9/2002 | Carson |
| 2002/0147455 A1 | 10/2002 | Carson |
| 2002/0151894 A1 | 10/2002 | Melkent et al. |
| 2002/0151898 A1 | 10/2002 | Sohngen et al. |
| 2002/0156371 A1 | 10/2002 | Hedlund et al. |
| 2002/0156479 A1 | 10/2002 | Schulzki et al. |
| 2002/0188194 A1 | 12/2002 | Cosman |
| 2002/0193800 A1 | 12/2002 | Kienzle, III et al. |
| 2002/0198448 A1 | 12/2002 | Zuk et al. |
| 2002/0198451 A1 | 12/2002 | Carson |
| 2002/0198531 A1 | 12/2002 | Millard et al. |
| 2003/0006107 A1 | 1/2003 | Thompson |
| 2003/0018338 A1 | 1/2003 | Axelson, Jr. et al. |
| 2003/0045883 A1 | 3/2003 | Chow et al. |
| 2003/0050643 A1 | 3/2003 | Taft |
| 2003/0030787 A1 | 4/2003 | Bradbury |
| 2003/0069591 A1 | 4/2003 | Carson |
| 2003/0073901 A1 | 4/2003 | Simon et al. |
| 2003/0153829 A1 | 8/2003 | Sarin et al. |
| 2003/0153859 A1 | 8/2003 | Hinshon |
| 2003/0153978 A1 | 8/2003 | Whiteside |
| 2003/0164172 A1 | 9/2003 | Chumas et al. |
| 2003/0181918 A1 | 9/2003 | Smothers et al. |
| 2003/0187351 A1 | 10/2003 | Franck et al. |
| 2003/0187452 A1 | 10/2003 | Smith et al. |
| 2003/0192557 A1 | 10/2003 | Krag et al. |
| 2003/0225329 A1 | 12/2003 | Rossner et al. |
| 2004/0019382 A1 | 1/2004 | Amirouche et al. |
| 2004/0073279 A1 | 4/2004 | Malackowski et al. |
| 2004/0087852 A1 | 5/2004 | Chen et al. |
| 2004/0097952 A1 | 5/2004 | Sarin et al. |
| 2004/0152970 A1 | 8/2004 | Hunter et al. |
| 2004/0153081 A1 | 8/2004 | Tulkis |
| 2004/0153083 A1 | 8/2004 | Nemec et al. |
| 2004/0171924 A1 | 9/2004 | Mire et al. |
| 2004/0243481 A1 | 12/2004 | Therics et al. |
| 2004/0254588 A1 | 12/2004 | Sarin |
| 2004/0260290 A1 | 12/2004 | Zander et al. |
| 2005/0021037 A1 | 1/2005 | McCombs et al. |
| 2005/0021043 A1 | 1/2005 | Jansen |
| 2005/0075632 A1 | 4/2005 | Russell et al. |
| 2005/0085715 A1 | 4/2005 | Dukesherer et al. |
| 2005/0085822 A1 | 4/2005 | Thornberry et al. |
| 2005/0101966 A1 | 5/2005 | Lavallee |
| 2005/0109855 A1 | 5/2005 | McCombs |
| 2005/0113658 A1 | 5/2005 | Jacobson et al. |
| 2005/0113659 A1 | 5/2005 | Pothier |
| 2005/0113846 A1 | 5/2005 | Carson |
| 2005/0119639 A1 | 6/2005 | McCombs |
| 2005/0119777 A1 | 6/2005 | Arbogast et al. |
| 2005/0124988 A1 | 6/2005 | Terrill-Grisoni et al. |
| 2005/0148843 A1 | 7/2005 | Roose |
| 2005/0149003 A1 | 7/2005 | Tierney et al. |
| 2005/0149041 A1 | 7/2005 | McGinley |
| 2005/0154331 A1 | 7/2005 | Christie et al. |
| 2005/0159759 A1 | 7/2005 | Harbaugh et al. |
| 2005/0177172 A1 | 8/2005 | Acker |
| 2005/0197569 A1 | 9/2005 | McCombs |
| 2005/0197814 A1 | 9/2005 | Aram et al. |
| 2005/0203384 A1 | 9/2005 | Sati et al. |
| 2005/0209726 A1 | 9/2005 | Voit et al. |
| 2005/0216305 A1 | 9/2005 | Funderud |
| 2005/0228266 A1 | 10/2005 | McCombs |
| 2005/0228404 A1 | 10/2005 | Vandevelde |
| 2005/0234332 A1 | 10/2005 | Murphy |
| 2005/0234465 A1 | 10/2005 | McCombs |
| 2005/0234466 A1 | 10/2005 | Stallings |
| 2005/0234468 A1 | 10/2005 | Carson |
| 2005/0245808 A1 | 11/2005 | Carson |
| 2005/0288676 A1 | 12/2005 | Schnieders |
| 2006/0015120 A1 | 1/2006 | Richard et al. |
| 2006/0161051 A1 | 7/2006 | Terrill-Grisoni et al. |
| 2006/0190011 A1 | 8/2006 | Landrem |
| 2006/0200025 A1 | 9/2006 | Elliott |
| 2006/0229626 A1 | 10/2006 | Kelman |
| 2007/0118055 A1 | 5/2007 | McCombs |
| 2007/0123912 A1 | 5/2007 | Carson |
| 2007/0169782 A1 | 7/2007 | Castleman |

FOREIGN PATENT DOCUMENTS

| | | |
|---|---|---|
| DE | 196 29 011 A1 | 1/1998 |
| DE | 197 09 960 A | 9/1998 |
| DE | 299 06 438 U1 | 9/1999 |
| DE | 296 23 941 U1 | 11/2000 |
| DE | 200 21 494 | 3/2001 |
| DE | 201 03 416 U1 | 7/2001 |
| DE | 100 12 042 | 8/2001 |
| DE | 100 31 887 A1 | 1/2002 |
| DE | 102 07 035 | 2/2002 |
| DE | 100 45 381 A1 | 4/2002 |
| DE | 202 13 243 | 10/2002 |
| DE | 203 09 399 | 8/2003 |
| EP | 0 327 509 B1 | 8/1989 |
| EP | 0 337 901 A1 | 10/1989 |
| EP | 0 340 176 A2 | 11/1989 |
| EP | 0 216 794 | 12/1989 |
| EP | 0 366 488 B1 | 5/1990 |
| EP | 0 376 657 B1 | 7/1990 |
| EP | 0 380 451 A2 | 8/1990 |
| EP | 0 415 837 A2 | 3/1991 |
| EP | 0 428 303 A1 | 5/1991 |
| EP | 0 466 659 A2 | 1/1992 |
| EP | 0 359 097 B1 | 8/1992 |
| EP | 0 538 152 A1 | 4/1993 |
| EP | 0 538 153 B1 | 4/1993 |
| EP | 0 555 003 B1 | 8/1993 |
| EP | 0 676 178 A | 10/1995 |
| EP | 0 720 834 A2 | 7/1996 |
| EP | 0 619 097 B1 | 6/1999 |
| EP | 1 149 562 A2 | 10/2001 |

| | | | |
|---|---|---|---|
| EP | 1 033 108 A1 | 2/2002 |
| EP | 1 190 676 B1 | 3/2002 |
| EP | 1 226 788 | 7/2002 |
| EP | 1 226 788 A1 | 7/2002 |
| EP | 0 782 842 B1 | 9/2002 |
| EP | 1 236 450 A1 | 9/2002 |
| EP | 1 249 207 | 10/2002 |
| EP | 1 348 384 A2 | 10/2003 |
| EP | 1 384 456 A2 | 1/2004 |
| EP | 1 405 603 A2 | 4/2004 |
| EP | 1 406 203 | 4/2004 |
| EP | 1 435 223 A1 | 7/2004 |
| EP | 1 459 686 A2 | 9/2004 |
| EP | 1 532 946 A2 | 5/2005 |
| EP | 1 563 795 A1 | 8/2005 |
| FR | 2 828 397 A | 2/2003 |
| GB | 2 224 937 | 5/1990 |
| GB | 2 397 769 A | 8/2004 |
| JP | 2002-304439 | 10/2002 |
| WO | WO 1986/05384 | 9/1986 |
| WO | WO 1989/09570 | 10/1989 |
| WO | WO94/17733 | 8/1994 |
| WO | WO95/15714 | 6/1995 |
| WO | WO96/35387 | 11/1996 |
| WO | WO97/16129 | 5/1997 |
| WO | WO97/23172 | 7/1997 |
| WO | WO97/29683 | 8/1997 |
| WO | WO98/29032 | 7/1998 |
| WO | WO98/46169 | 10/1998 |
| WO | WO99/15097 | 4/1999 |
| WO | WO99/27860 | 6/1999 |
| WO | WO99/60939 | 12/1999 |
| WO | WO99/65380 | 12/1999 |
| WO | WO 00/00093 | 1/2000 |
| WO | WO 00/21442 | 4/2000 |
| WO | WO 00/47103 | 8/2000 |
| WO | WO 00/64367 | 11/2000 |
| WO | WO 01/01845 A2 | 1/2001 |
| WO | WO 01/19271 A2 | 3/2001 |
| WO | WO 2001/34050 A2 | 5/2001 |
| WO | WO 01/64124 A1 | 9/2001 |
| WO | WO 01/67979 A1 | 9/2001 |
| WO | WO 01/91647 | 12/2001 |
| WO | WO 01/91647 A1 | 12/2001 |
| WO | WO 01/93770 A1 | 12/2001 |
| WO | WO 02/24096 A1 | 3/2002 |
| WO | WO 02/041794 A1 | 5/2002 |
| WO | WO 02/063236 A1 | 8/2002 |
| WO | WO 02/063236 A3 | 8/2002 |
| WO | WO 02/064042 | 8/2002 |
| WO | WO 02/067783 | 9/2002 |
| WO | WO 02/067784 | 9/2002 |
| WO | WO 02/067800 | 9/2002 |
| WO | WO 02/080824 A1 | 10/2002 |
| WO | WO 03/006107 | 1/2003 |
| WO | WO 2003/015642 | 2/2003 |
| WO | WO 2003/015642 A1 | 2/2003 |
| WO | WO 2003/030787 | 4/2003 |
| WO | WO 2003/034213 A2 | 4/2003 |
| WO | WO 03/034933 A1 | 5/2003 |
| WO | WO 03/041566 A2 | 5/2003 |
| WO | WO 2003/037192 A1 | 5/2003 |
| WO | WO 03/065931 | 8/2003 |
| WO | WO 03/065949 A2 | 8/2003 |
| WO | WO 03/068090 A1 | 8/2003 |
| WO | WO 03/075740 A2 | 9/2003 |
| WO | WO 2003/071969 A1 | 9/2003 |
| WO | WO 03/079940 | 10/2003 |
| WO | WO 03/096870 A2 | 11/2003 |
| WO | WO 2004/001569 A2 | 12/2003 |
| WO | WO 2004/017842 A2 | 3/2004 |
| WO | WO 2004/019792 | 3/2004 |
| WO | WO 2004/029908 A1 | 4/2004 |
| WO | WO 2004/030556 A2 | 4/2004 |
| WO | WO 2004/030559 A1 | 4/2004 |
| WO | WO 04/046754 A2 | 6/2004 |
| WO | WO 2004/069036 | 8/2004 |
| WO | WO 2004/070580 | 8/2004 |
| WO | WO 2004/084740 A1 | 10/2004 |
| WO | WO 2005/009303 | 2/2005 |
| WO | WO 2005/039430 A2 | 5/2005 |
| WO | WO 2005/041802 A1 | 5/2005 |
| WO | WO 2005/044126 A1 | 5/2005 |
| WO | WO05/048851 A1 | 6/2005 |
| WO | WO 05/053559 A1 | 6/2005 |
| WO | WO 2005/057439 | 6/2005 |
| WO | WO05/070312 A1 | 8/2005 |
| WO | WO 2005/070319 A1 | 8/2005 |
| WO | WO 2005/072629 A1 | 8/2005 |
| WO | WO 2005/096982 | 10/2005 |
| WO | WO 2006/044367 A1 | 4/2006 |
| WO | WO 2006/060631 A1 | 6/2006 |
| WO | WO 2006078236 A1 | 7/2006 |
| WO | WO 2008/021494 | 2/2008 |

OTHER PUBLICATIONS

BrainLAB Brochure entitled "Ortho . . . Your Partner for the Future" pp. 1-28 (2002).

Barnes et al., "Unicompartmental Knee Arthroplasty," Bombay Hospital Journal, Issue Special, www.bhj.org/journal/1996/3803_july/special_486.htm.

Croitoru, et al.., Fixation-Based Surgery: A New Technique for Distal Radius Osteotomy, Clinical Paper, Computer Aided Surgery 2001, 160-169, vol. 6.

Delp, et al., "Computer-Assisted Knee Replacement," *Clinical Orthopaedics and Related Research*. 354:49-56 (1998).

Deluzio et al., "Static alignment and the adduction moment in unicompartmental arthroplasty patients," Presented at NACOB 98: North American Congress on Biomechanics, University of Waterloo, Ontario, Canada, Aug. 14-18, 1998.

DiGioia et al., Computer Assisted Orthopedic Surgery, Clinical Orthopaedics, Sep. 1998, vol. 354, No. 8-16.

Ellis, et al., "A Surgical Planning and Guidance System for High Tibial Osteotomy," *Journal of Computer-Assisted Surgery*, 4(5):264-274 (1999).

Foley et al., "Percutaneous pedicle screw fixation of the lumbar spine," *Neurosurg. Focus*, vol. 10(4), pp. 1-8 (2001).

Iyun, et al.., Planning and Performing the Ilizarov Method with the Taylor Spatial Frame, Abstract, at $2^{nd}$ Annual Meeting of International Society for Computer Assisted Orthopaedic Surgery, Jun. 21, 2002.

Kanada, et al., "Image-Based Computer Assisted Orthopedic Surgery System," Bonecraft, Inc. (2 pages) (Apr. 30, 2001.

Kiefer et al., Computer Aided Knee Arthroplasty Versus Conventional Technique—First Results, First Annual Meeting of the International Society for Computer Assisted Orthopedic Surgery (Davos. Switzerland, Feb. 8-10, 2001).

Krause, Computer-Aided Bone Deformity Correction, http://www.nd.edu/~gcopping/files/bonecraft6.pdf, May 21, 2001.

Kunz et al., Development and Verification of a Non-CT Based Total Knee Arthroplasty System for the LCS Prosthesis, First Annual Meeting of the International Society for Computer Assisted Orthopedic Surgery (Davos. Switzerland, Feb. 8-10, 2001).

Munoz, et al., Computer Assisted Planning of Hig Tibial Osteotomy for the Treatment of Knee Osteoarthritis. http://www.utc.fr/esb/esb09/abs_htm/570.html (Feb. 21, 2002) (three pages).

Picard et al., Kneenav. TKR: Concept and Clinical Application (Computer Assisted Orthopedic Surgery USA 2000 Meeting, Pittsburgh, PA., Jun. 15-17, 2000).

Saragaglia et al., Computer Assisted Total Knee Arthroplasty: Comparison with a Conventional Procedure, First Annual Meeting of the International Society for Computer Assisted Orthopedic Surgery (Davos, Switzerland, Feb. 8-10, 2001).

Simon et al., The Fundamentals of Virtual Fluoroscopy, Medtronic Surgical Navigation Technologies, Medtronic, pp. 57-66 (Computer Assisted Orthopedic Surgery USA 2000 Meeting, Pittsburgh, PA, Jun. 15-17, 2000).

Tenbusch et al., First Results Using the Robodoc System for Total Knee Replacement, First Annual Meeting of the International Society for Computer Assisted Orthopedic Surgery (Davos, Switzerland, Feb. 8-10, 2001).

Stryker Navigation System brochure entitled ". . . best alignment for gap kinematics," two pages (undated).

Bonutti, et al., "Minimal Incision Total Knee Arthroplasty Using the Suspended Leg Technique," *Orthopedics*, (published Sep. 2003), 6 pages http://www.orthobluejournal.com/0903/9tips.asp.

Bonutti, "Total Joint Replacement Surgery in the 21st Century—New 'Limited-Incision' Total Knee Replacement Offers Important Advantages," 01 page (undated).

Ellis, et al., "A Surgical Planning and Guidance System for High Tibial Osteotomy," *Journal of Computer-Assisted Surgery*, 4(5):264-274 (1999).

Glossop, http:/www/traxta.com/papers/cua/model.html, 8 pages (Feb. 6, 2002).

Sugano, et al., "Medical Robotics and Computer-Assisted Surgery in the Surgical Treatment of Patients and Rheumatic Diseases," *Cutting Edge Reports*, http://www/rheuma21st.com/archives/cutting_edge_Robotics_Japan.html (Apr. 27, 2000).

Suhm, et al., "Adapting the C-Arm Fluoroscope for Image Guided Orthopaedic Surgery," *CAOS*, pp. 212-214 (2002).

Valstar, et al., "Towards computer-assisted surgery in should joint replacement," *ISPRS Journal of Photogrammetry & Remote Sensing*, 56:326-337 (2002).

Patent Abstracts of Japan, vol. 2002, No. 05, May 3, 2002 & JP 2002 017740A (Ochi Takahiro; Yonenobu Sakuo: MMT:KK) Jan. 22, 2002 Abstract.

iON™ Smith & Nephew Orthopaedics Brochure entitled "You'll Never Look At Your Patients The Same Way Again." 10 pages (Jan. 2001).

Smith & Nephew—Orthopaedics—TriGen Reducer http://www.smithnephew.com/US/Standard.asp?NodeID=2996, one page (Jan. 21, 2003).

Smith & Nephew—Orthopaedics—TriGen Flexible Reamer System http://www.smithnephew.com/US/Standard.asp?NodeID=2998, 02 pages (Jan. 21, 2003).

AO Development Institute "MEPUC Motorized Exact Positioning Unit . . . " one page (Mar. 26, 2003) http://www/ao-asif.ch/development/adi/examples/mepuc.shtml.

AO Development Institute "MEPUC Motorized Exact Positioning Unit for C-arm," one page (Jul. 7, 2003) http://www.ao-asif.ch/development/adi/examples/mepuc.shtml.

Smith & Nephew—Orthopaedics—CAS—Knees Computer Assisted Total Knee Replacement Surgery, 02 pages (Oct. 13, 2004) http://ortho.smith-nephew.com/us/Standard.asp?NodeId=3396.

Smith & Nephew ORTHOPAEDIC product bulletin , 01 page.

Smith & Nephew Brochure entitled "Surgical Technique Mini Incision Hip Posterior Approach," 20 pages (Mar. 2003).

Tricon Total Knee System, "Tricon-M® with Pro-Fit™ Surgical Procedures," Richards Brochure, pp. 1-29 (undated).

Smith & Nephew Richards Genesis® Total Knee System, "Revision Posterior Referencing Instrumentaion Surgical Technique," Brochure, pp. 1-51 (Dec. 1993).

Smith & Nephew Richards Genesis® "Total Knee System Primary Surgical Technique Anterior Referencing Instrumentation," pp. 59 (Dec. 1993).

Smith & Nephew Genesis II "Total Knee System Primary Surgical Technique," Brochure, pp. 1-36 (Mar. 2001).

Smith & Nephew First Choice in Orthopaedics Brochure Entitled "Achieve Computer Assisted Surgery Trauma Applications The Orbiter Base Station & Satellite Surgical Platform," 18 pages (undated).

Medtronic Surgical Navigation Technologies SNT VERTEK photograph, one page (undated).

Medtronic Surgical Navigation Technologies System Components photograph VERTEK Platform, one page (undated).

Medtronic Surgical Navigation Technologies "Overview Image-Guided Surgery An Advanced Solution to Traditional Surgery," two pages (undated).

Bonecraft Carnegie Mellon Computer-Aided Bone Deformity Correction Brochure, pp. 1-5 (undated).

Smith & Nephew Total Hip Replacement Surgery, HipReplacementInfo.com, 3 pages, Nov. 8, 2005, http://www/hipreplacementinfo.com/hip-total-replacement.htm.

Smith & Nephew Brochure, Design Features, "Opera" pp. 4-15 (1999).

Corinth Surgeon Performs Revolutionary Hip Replacement, Mississippi Medical News, pp. 1-2 (Nov. 17, 2005), http://host1.bondware.com/~mississippi/news.php?viewsStory=347.

Dario, et al., 'Smart Surgical Tools and Augmenting Devices,' IEEE Trans. Rob. Autom., 19(5):782-792 (2003).

Fernandez-Lozano, et al., 'Human-machine interface evaluation in a computer assisted surgical system,' Proc. IEEE Int. Conf. Rob. Autom., 2004:231-236 (2004).

Martelli, et al., 'Criteria of Interface evaluation for computer assisted surgery systems,' Int. J. Med. Informatics, 72:35-45 (2003).

Visarius, et al., 'Man-machine interfaces in computer assisted surgery,' Computer Aided Surgery, pp. 102-107 (2004).

DePuy, a Johnson & Johnson Company, Brochure entitled 'S-ROM Modular Hip System Minimally Invazive Calcar Miller Surgical Technique,' 12 pages (2004).

"Implant", Merriam-Webster Online Dictionary [online], [retrieved on Jan. 11, 2007], Retrieved from the Internet URL:www.m-w.com.

* cited by examiner

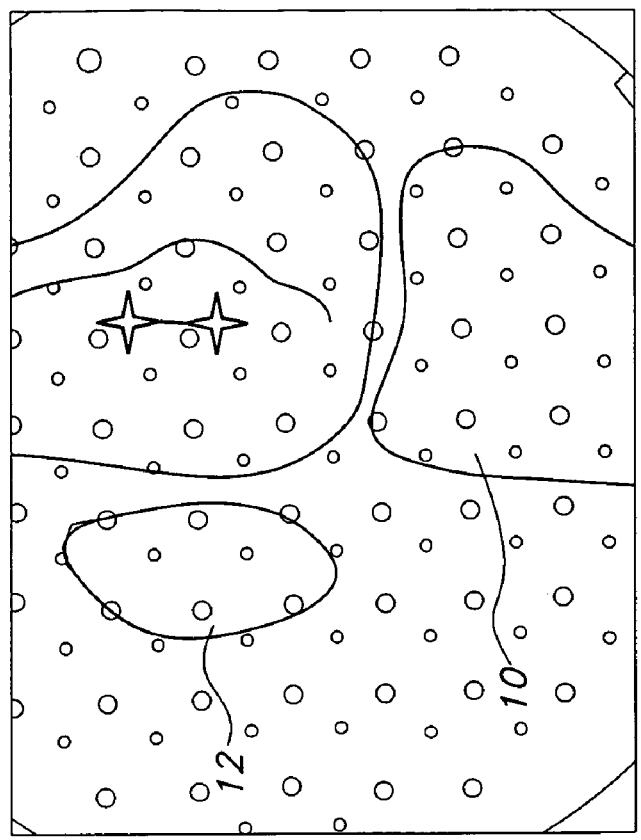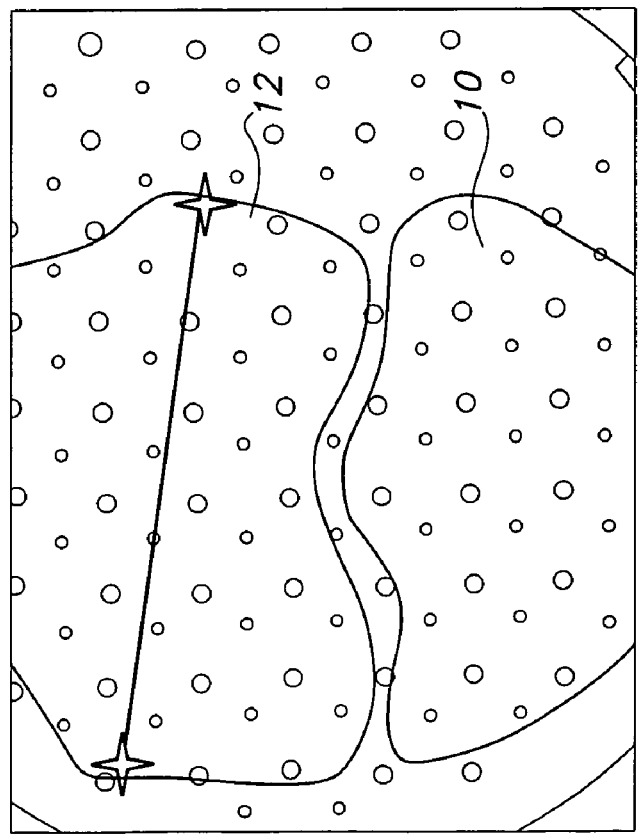
FIG. 20

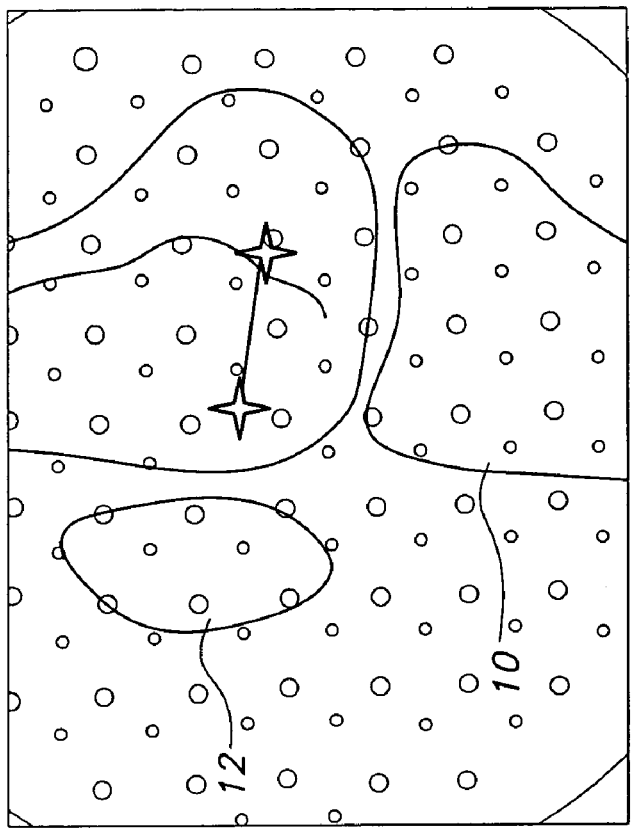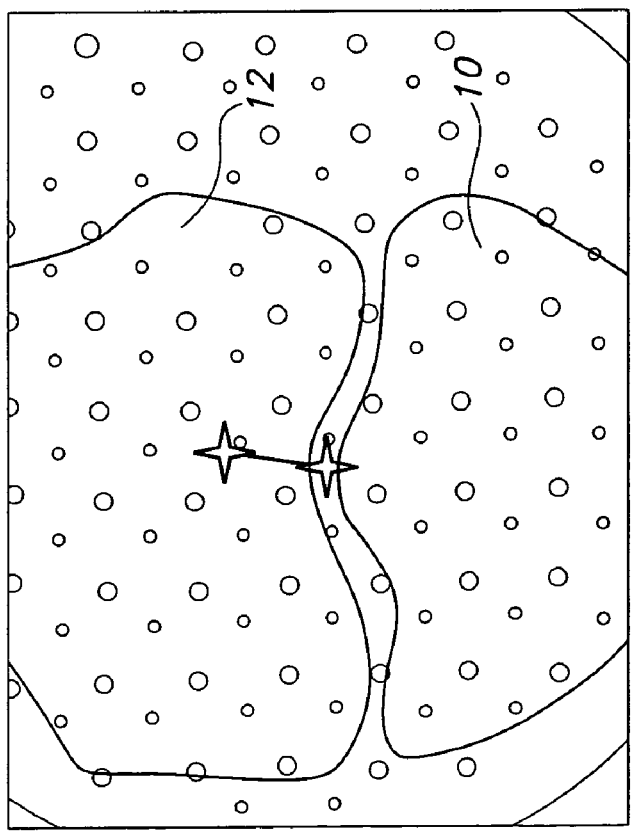
FIG. 21

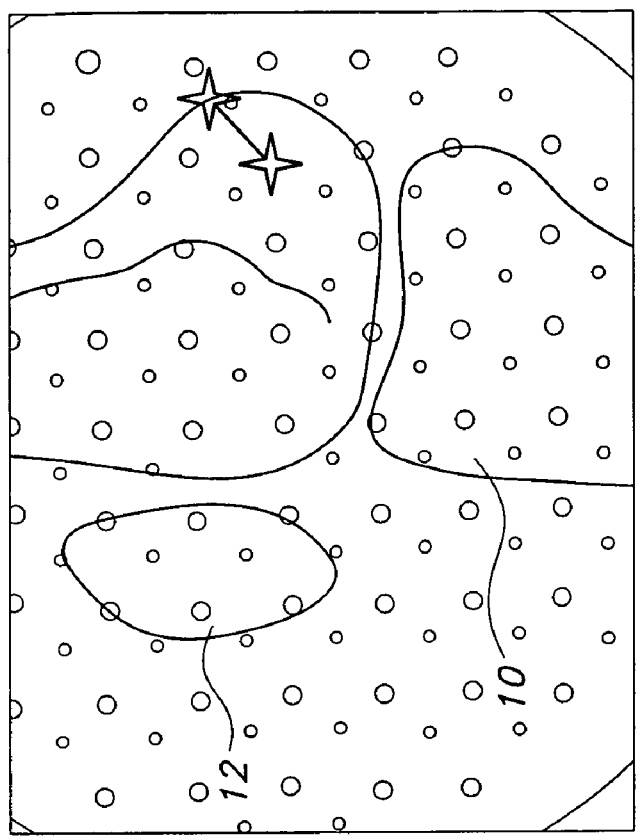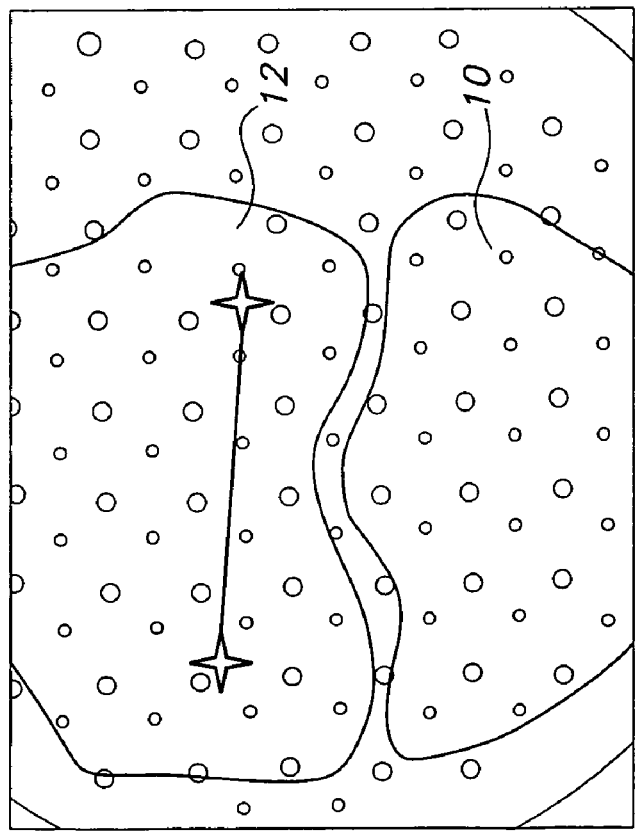
FIG. 22

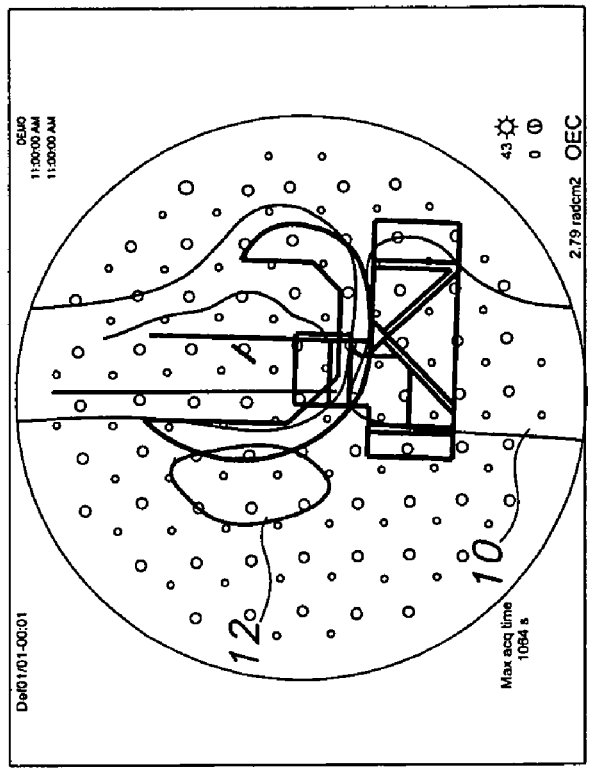
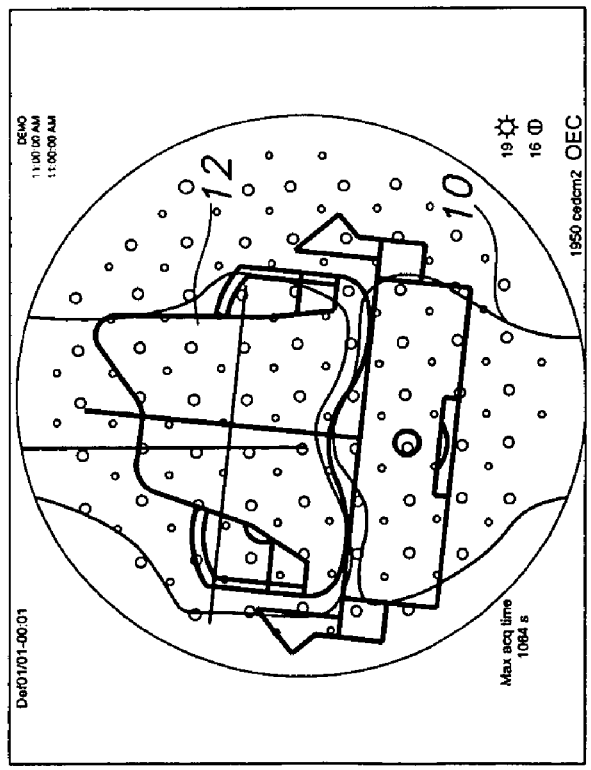
FIG. 34

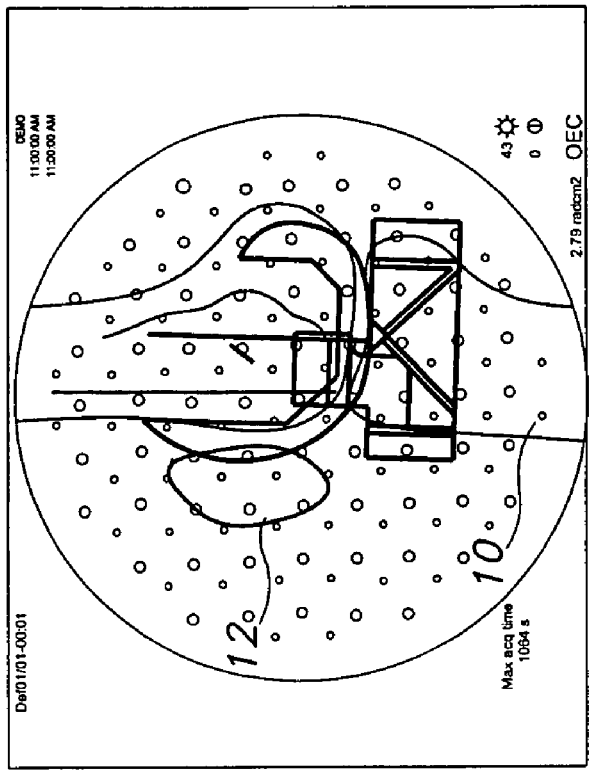
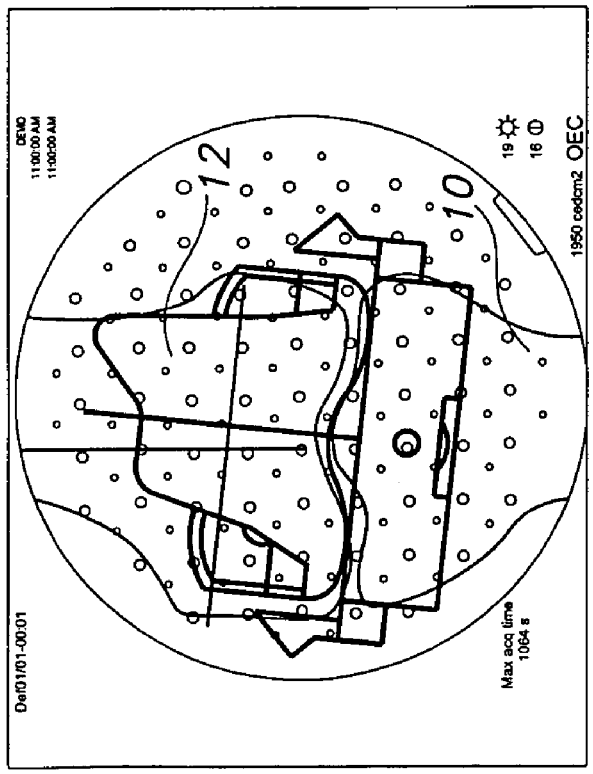
FIG. 35

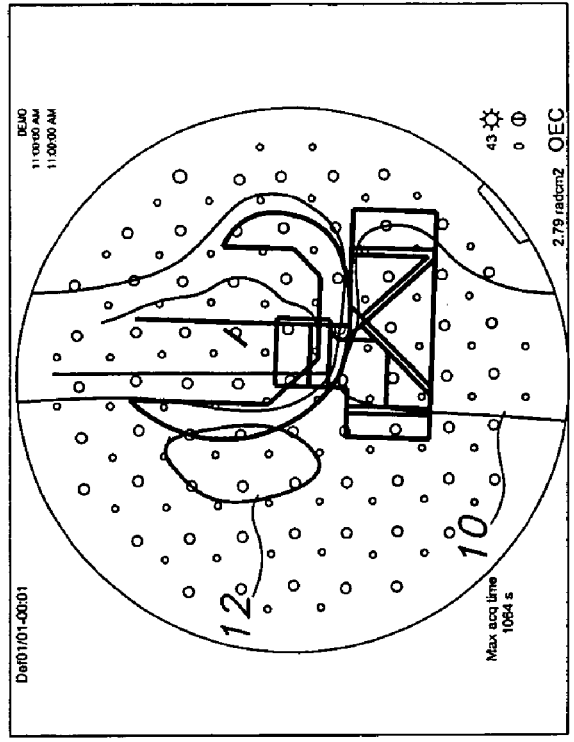
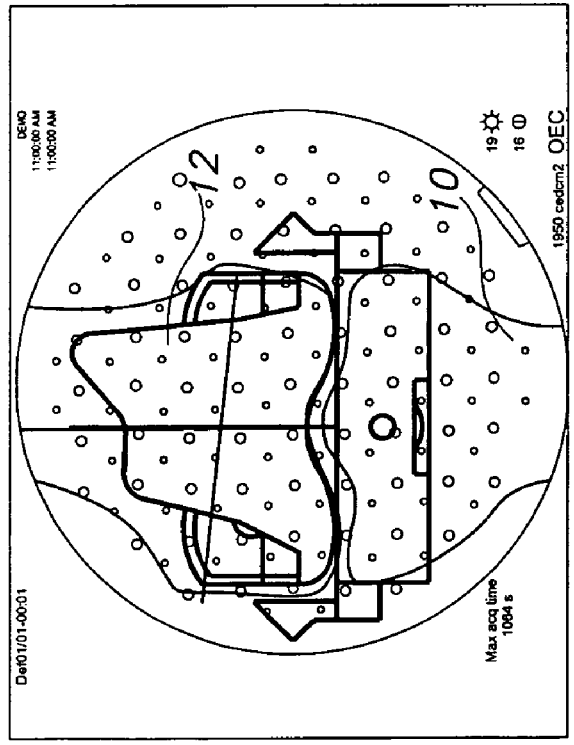
FIG. 36

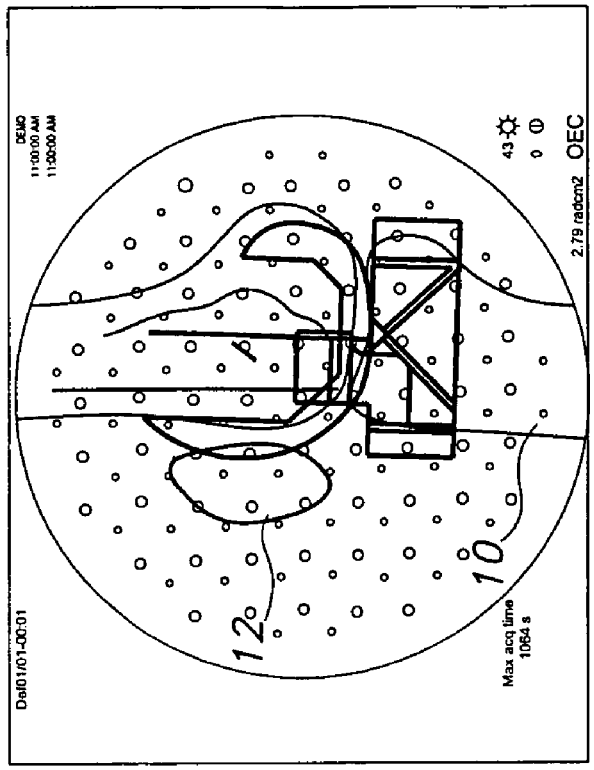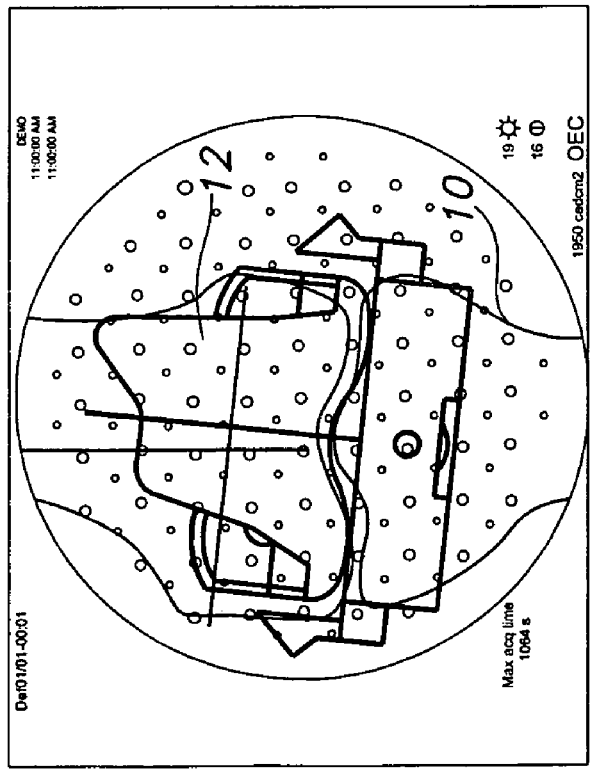
FIG. 37

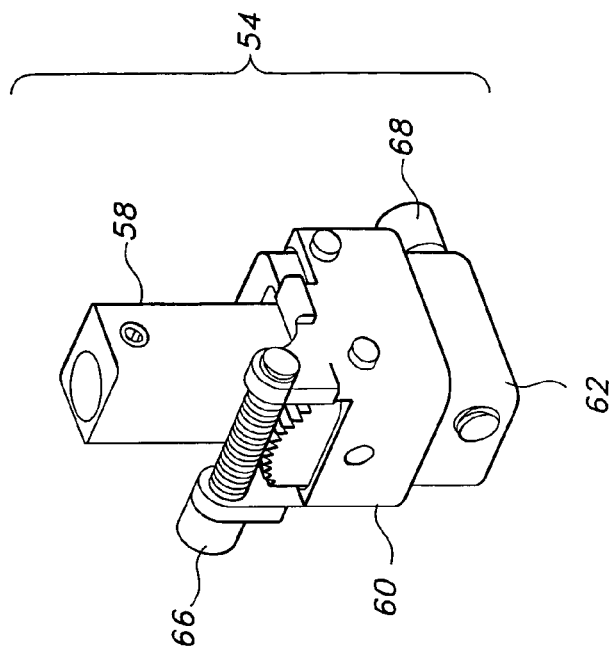
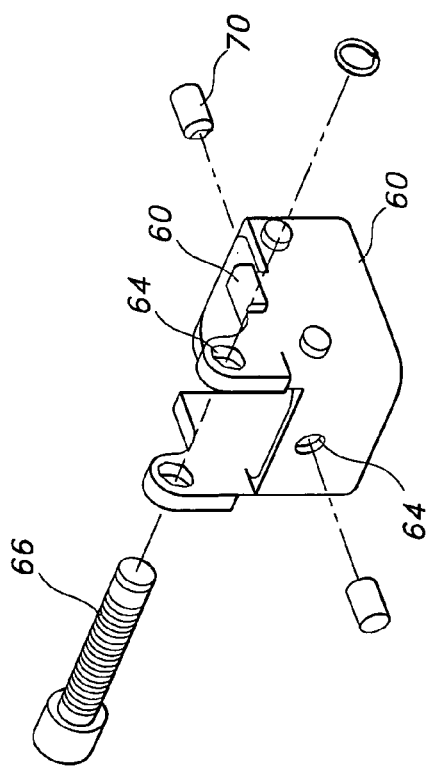
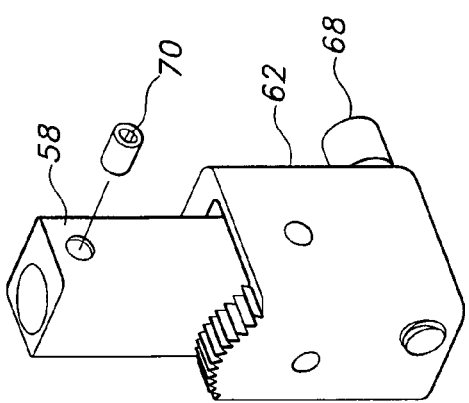
FIG. 38A
FIG. 38B
FIG. 38C

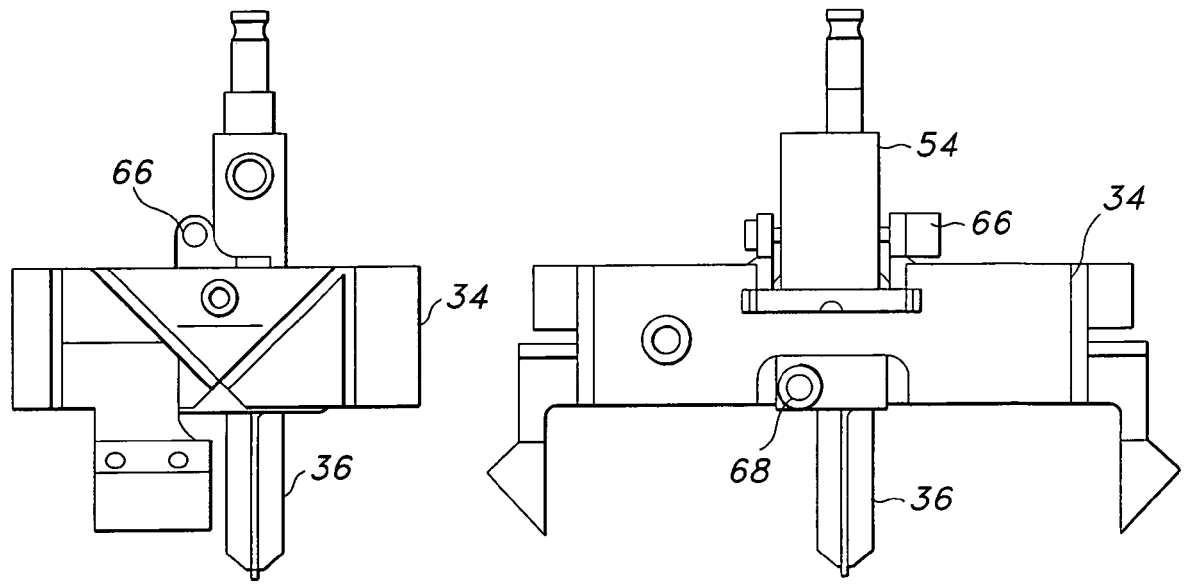
FIG. 40A   FIG. 40B
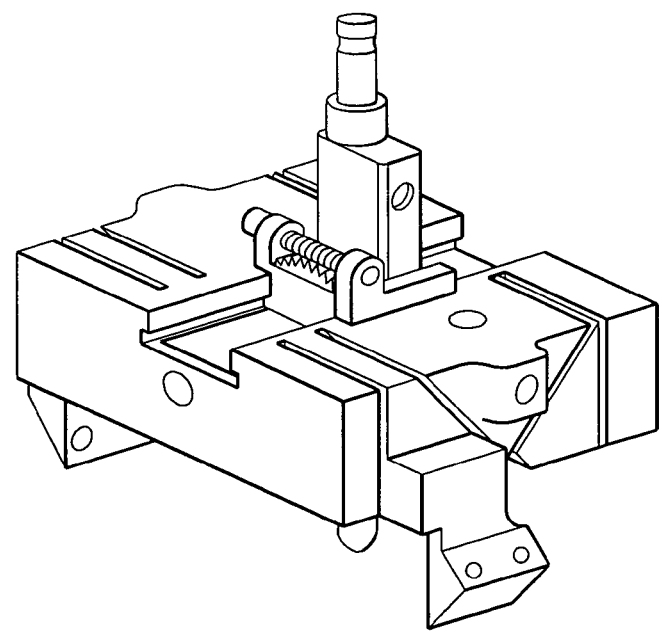
FIG. 40C

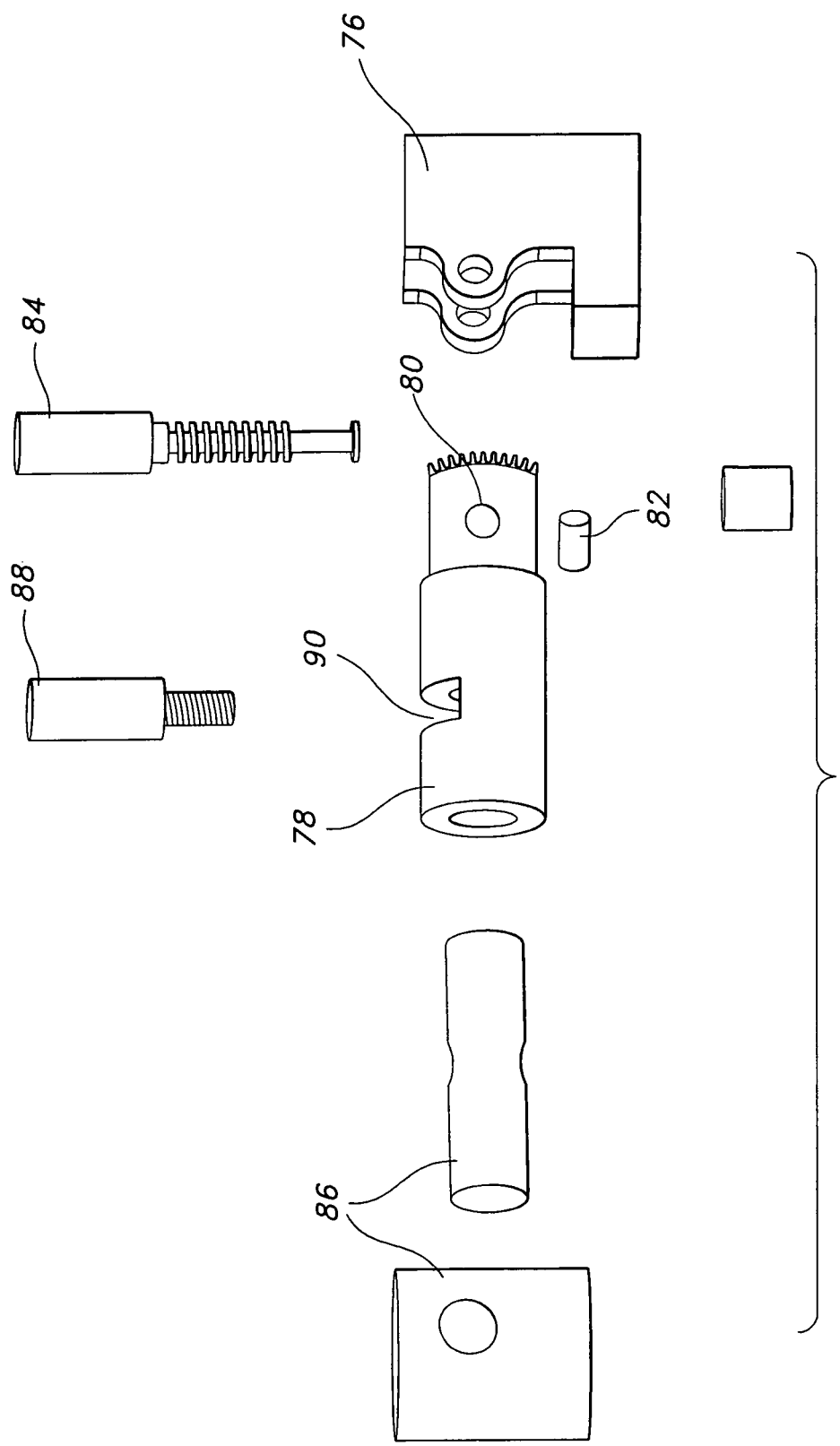

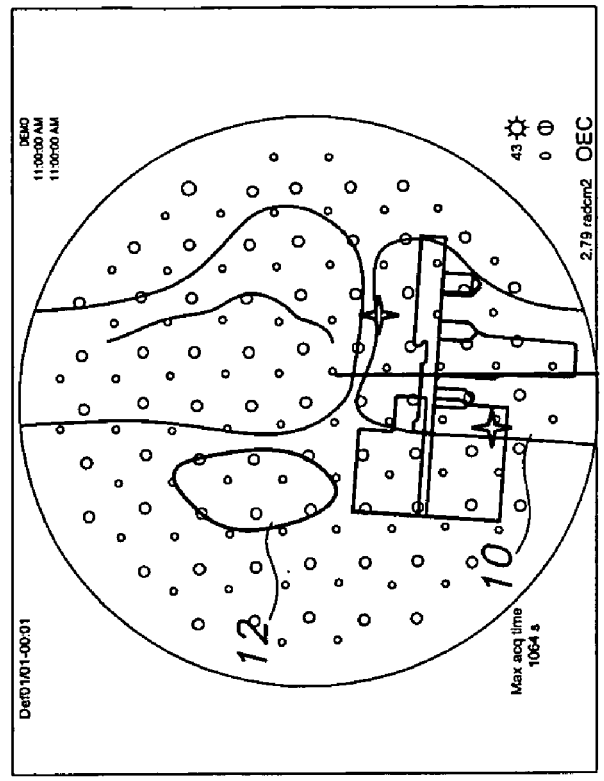
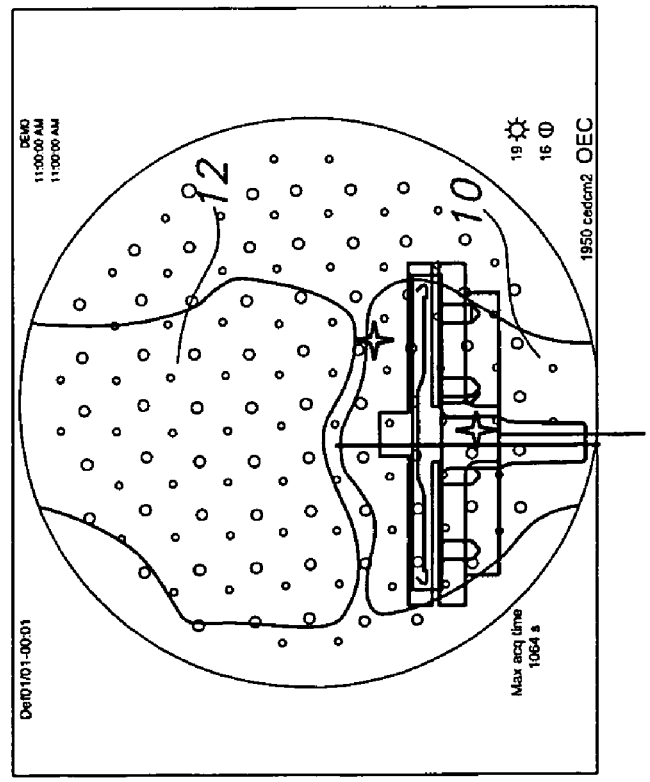
FIG. 50

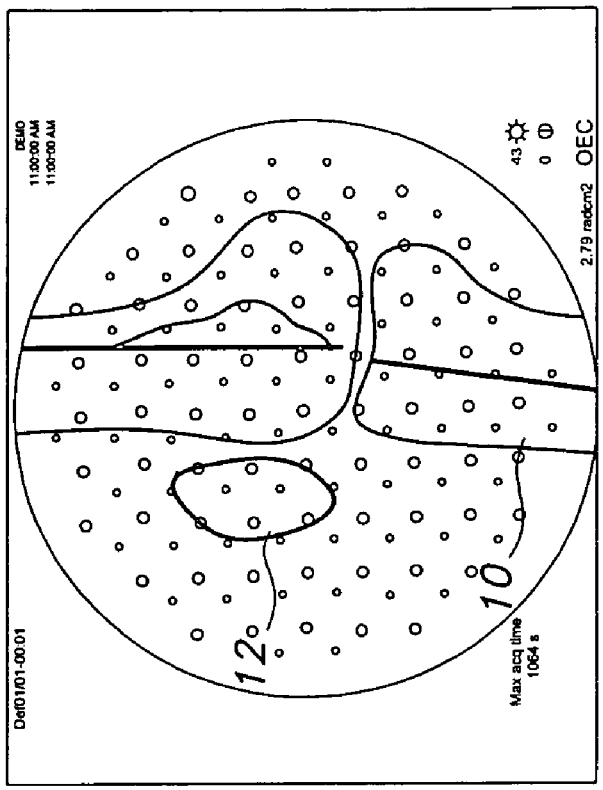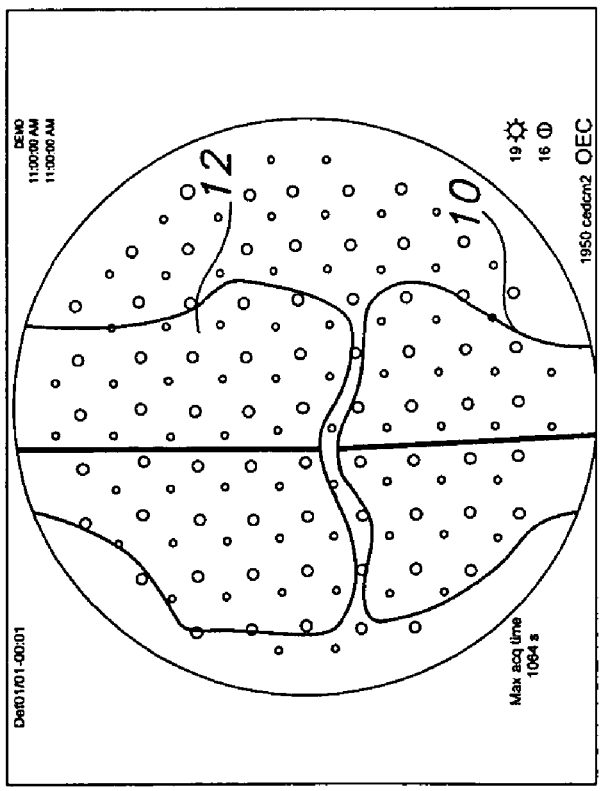
FIG. 72

COMPUTER ASSISTED KNEE ARTHROPLASTY INSTRUMENTATION, SYSTEMS, AND PROCESSES

RELATED APPLICATION DATA

This application claims priority to U.S. Ser. No. 10/084,012 filed on Feb. 27, 2002, which claims the benefit of U.S. Provisional Application No. 60/355,899 filed on Feb. 11, 2002 and U.S. Provisional Application No. 60/271,818 filed on Feb. 27, 2001.

FIELD OF INVENTION

Instrumentation, systems, and processes for tracking anatomy, implements, instrumentation, trial implants, implant components and virtual constructs or references, and rendering images and data related to them in connection with orthopedic, surgical and other operations, for example Total Knee Arthroplasty ("TKA"). Anatomical structures and such items may be attached to or otherwise associated with fiducial functionality, and constructs may be registered in position using fiducial functionality whose position and orientation can be sensed and tracked by systems and according to processes of the present invention in three dimensions in order to perform TKA. Such structures, items and constructs can be rendered onscreen properly positioned and oriented relative to each other using associated image files, data files, image input, other sensory input, based on the tracking. Such instrumentation, systems, and processes, among other things, allow surgeons to navigate and perform TKA using images that reveal interior portions of the body combined with computer generated or transmitted images that show surgical implements, instruments, trials, implants, and/or other devices located and oriented properly relative to the body part. Such instrumentation, systems, and processes allow, among other things, more accurate and effective resection of bone, placement and assessment of trial implants and joint performance, and placement and assessment of performance of actual implants and joint performance.

BACKGROUND AND SUMMARY

A leading cause of wear and revision in prosthetics such as knee implants, hip implants and shoulder implants is less than optimum implant alignment. In a Total Knee Arthroplasty, for example, current instrument design for resection of bone limits the alignment of the femoral and tibial resections to average values for varus/valgus flexion/extension, and external/internal rotation. Additionally, surgeons often use visual landmarks or "rules of thumb" for alignment which can be misleading due to anatomical variability. Intramedullary referencing instruments also violate the femoral and tibial canal. This intrusion increases the risk of fat embolism and unnecessary blood loss in the patient. Surgeons also rely on instrumentation to predict the appropriate implant size for the femur and tibia instead of the ability to intraoperatively template the appropriate size of the implants for optimal performance. Another challenge for surgeons is soft tissue or ligament balancing after the bone resections have been made. Releasing some of the soft tissue points can change the balance of the knee; however, the multiple options can be confusing for many surgeons. In revision TKA, for example, many of the visual landmarks are no longer present, making alignment and restoration of the joint line difficult. The present invention is applicable not only for knee repair, reconstruction or replacement surgery, but also repair, reconstruction or replacement surgery in connection with any other joint of the body as well as any other surgical or other operation where it is useful to track position and orientation of body parts, non-body components and/or virtual references such as rotational axes, and to display and output data regarding positioning and orientation of them relative to each other for use in navigation and performance of the operation.

Several providers have developed and marketed various forms of imaging systems for use in surgery. Many are based on CT scans and/or MRI data or on digitized points on the anatomy. Other systems align preoperative CT scans, MRIs or other images with intraoperative patient positions. A preoperative planning system allows the surgeon to select reference points and to determine the final implant position. Intraoperatively, the system calibrates the patient position to that preoperative plan, such as using a "point cloud" technique, and can use a robot to make femoral and tibial preparations.

Instrumentation, systems, and processes according to one embodiment of the present invention use position and/or orientation tracking sensors such as infrared sensors acting stereoscopically or otherwise to track positions of body parts, surgery-related items such as implements, instrumentation, trial prosthetics, prosthetic components, and virtual constructs or references such as rotational axes which have been calculated and stored based on designation of bone landmarks. Processing capability such as any desired form of computer functionality, whether standalone, networked, or otherwise, takes into account the position and orientation information as to various items in the position sensing field (which may correspond generally or specifically to all or portions or more than all of the surgical field) based on sensed position and orientation of their associated fiducials or based on stored position and/or orientation information. The processing functionality correlates this position and orientation information for each object with stored information regarding the items, such as a computerized fluoroscopic imaged file of a femur or tibia, a wire frame data file for rendering a representation of an instrumentation component, trial prosthesis or actual prosthesis, or a computer generated file relating to a rotational axis or other virtual construct or reference. The processing functionality then displays position and orientation of these objects on a screen or monitor, or otherwise. Thus, instrumentation, systems, and processes according to one embodiment of the invention can display and otherwise output useful data relating to predicted or actual position and orientation of body parts, surgically related items, implants, and virtual constructs for use in navigation, assessment, and otherwise performing surgery or other operations.

As one example, images such as fluoroscopy images showing internal aspects of the femur and tibia can be displayed on the monitor in combination with actual or predicted shape, position and orientation of surgical implements, instrumentation components, trial implants, actual prosthetic components, and rotational axes in order to allow the surgeon to properly position and assess performance of various aspects of the joint being repaired, reconstructed or replaced. The surgeon may navigate tools, instrumentation, trial prostheses, actual prostheses and other items relative to bones and other body parts in order to perform TKA's more accurately, efficiently, and with better alignment and stability. Instrumentation, systems, and processes according to the present invention can also use the position tracking information and, if desired, data relating to shape and configuration of surgical related items and virtual constructs or references in order to produce numerical data which may be used with or without graphic imaging to perform tasks such as assessing performance of trial prosthetics statically and throughout a range of motion, appropriately modifying tissue such as ligaments to improve such performance and similarly assessing performance of actual prosthetic components which have been placed in the patient for alignment and stability. Instrumentation, systems, and processes according to the present invention can also generate data based on position tracking and, if desired, other information to provide cues on screen, aurally or as otherwise desired to assist in the surgery such as suggesting certain bone modification steps or measures which may be taken to release certain ligaments or portions of them based on performance of components as sensed by instrumentation, systems, and processes according to the present invention.

According to a preferred embodiment of instrumentation, systems, and processes according to the present invention, at least the following steps are involved:

1. Obtain appropriate images such as fluoroscopy images of appropriate body parts such as femur and tibia, the imager being tracked in position via an associated fiducial whose position and orientation is tracked by position/orientation sensors such as stereoscopic infrared (active or passive) sensors according to the present invention.

2. Register tools, instrumentation, trial components, prosthetic components, and other items to be used in surgery, each of which corresponds to a fiducial whose position and orientation can be tracked by the position/orientation sensors.

3. Locating and registering body structure such as designating points on the femur and tibia using a probe associated with a fiducial in order to provide the processing functionality information relating to the body part such as rotational axes.

4. Navigating and positioning instrumentation such as cutting instrumentation in order to modify bone, at least partially using images generated by the processing functionality corresponding to what is being tracked and/or has been tracked, and/or is predicted by the system, and thereby resecting bone effectively, efficiently and accurately.

5. Navigating and positioning trial components such as femoral components and tibial components, some or all of which may be installed using impactors with a fiducial and, if desired, at the appropriate time discontinuing tracking the position and orientation of the trial component using the impactor fiducial and starting to track that position and orientation using the body part fiducial on which the component is installed.

6. Assessing alignment and stability of the trial components and joint, both statically and dynamically as desired, using images of the body parts in combination with images of the trial components while conducting appropriate rotation, anterior-posterior drawer and flexion/extension tests and automatically storing and calculating results to present data or information which allows the surgeon to assess alignment and stability.

7. Releasing tissue such as ligaments if necessary and adjusting trial components as desired for acceptable alignment and stability.

8. Installing implant components whose positions may be tracked at first via fiducials associated with impactors for the components and then tracked via fiducials on the body parts in which the components are installed.

9. Assessing alignment and stability of the implant components and joint by use of some or all tests mentioned above and/or other tests as desired, releasing tissue if desired, adjusting if desired, and otherwise verifying acceptable alignment, stability and performance of the prosthesis, both statically and dynamically.

This process, or processes including it or some of it may be used in any total or partial joint repair, reconstruction or replacement, including knees, hips, shoulders, elbows, ankles and any other desired joint in the body.

Such processes are disclosed in U.S. Ser. No. 60/271,818 filed Feb. 27, 2001, entitled Image Guided System for Arthroplasty, which is incorporated herein by reference as are all documents incorporated by reference therein.

Instrumentation, systems, and processes according to the present invention represent significant improvement over other previous instrumentation, systems, and processes. For instance, systems which use CT and MRI data generally require the placement of reference frames pre-operatively which can lead to infection at the pin site. The resulting 3D images must then be registered, or calibrated, to the patient anatomy intraoperatively. Current registration methods are less accurate than the fluoroscopic system. These imaging modalities are also more expensive. Some "imageless" systems, or non-imaging systems, require digitizing a large number of points to define the complex anatomical geometries of the knee at each desired site. This can be very time intensive resulting in longer operating room time. Other imageless systems determine the mechanical axis of the knee by performing an intraoperative kinematic motion to determine the center of rotation at the hip, knee, and ankle. This requires placement of reference frames at the iliac crest of the pelvis and in or on the ankle. This calculation is also time consuming at the system must find multiple points in different planes in order to find the center of rotation. This is also problematic in patients with a pathologic condition. Ligaments and soft tissues in the arthritic patient are not normal and thus will give a center of rotation that is not desirable for normal knees. Robotic systems require expensive CT or MRI scans and also require pre-operative placement of reference frames, usually the day before surgery. These systems are also much slower, almost doubling operating room time and expense.

Some systems provide variable alignment modules, but none of these systems allow gross placement of cutting instruments followed by fine adjustment of cutting instruments through computer assisted navigation technology. Further, these systems can only be used with tibial instrumentation and cannot be used for femoral alignment and cutting.

None of these systems can effectively track femoral and/or tibial trials during a range of motion and calculate the relative positions of the articular surfaces, among other things. Also, none of them currently make suggestions on ligament balancing, display ligament balancing techniques, or surgical techniques. Additionally, none of these systems currently track the patella.

An object of certain aspects of the present invention is to use computer processing functionality in combination with imaging and position and/or orientation tracking sensors to present to the surgeon during surgical operations visual and data information useful to navigate, track and/or position implements, instrumentation, trial components, prosthetic components and other items and virtual constructs relative to the human body in order to improve performance of a repaired, replaced or reconstructed knee joint.

Another object of certain aspects of the present invention is to use computer processing functionality in combination with imaging and position and/or orientation tracking sensors to present to the surgeon during surgical operations visual and data information useful to assess performance of a knee and certain items positioned therein, including components such as trial components and prosthetic components, for stability, alignment and other factors, and to adjust tissue and body and non-body structure in order to improve such performance of a repaired, reconstructed or replaced knee joint.

Another object of certain aspects of the present invention is to use computer processing functionality in combination with imaging and position and/or orientation tracking sensors to present to the surgeon during surgical operations visual and data information useful to show predicted position and movement of implements, instrumentation, trial components, prosthetic components and other items and virtual constructs relative to the human body in order to select appropriate components, resect bone accurately, effectively and efficiently, and thereby improve performance of a repaired, replaced or reconstructed knee joint.

Other objects, features and advantages of the present invention are apparent with respect to the remainder of this document.

BRIEF DESCRIPTION OF THE DRAWINGS

FIG. 20 is a screen face produced according to one embodiment of the present invention during designation of landmarks to determine an epicondylar axis.

FIG. 21 is a screen face produced according to one embodiment of the present invention during designation of landmarks to determine an anterior-posterior axis.

FIG. 22 is a screen face produced according to one embodiment of the present invention during designation of landmarks to determine a posterior condylar axis.

FIG. 34 is a screen face which shows a fluoroscopic image of bone in combination with computer generated images of axes and components in accordance with one embodiment of the present invention.

FIG. 35 is a screen face which shows a fluoroscopic image of bone in combination with computer generated images of axes and components in accordance with one embodiment of the present invention.

FIG. 36 is a screen face which shows a fluoroscopic image of bone in combination with computer generated images of axes and components in accordance with one embodiment of the present invention.

FIG. 37 is a screen face which shows a fluoroscopic image of bone in combination with computer generated images of axes and components in accordance with one embodiment of the present invention.

FIGS. 38A–C are views showing certain aspects of a gimbal alignment module according to one embodiment of the present invention.

FIGS. 40A, 40B and 40C show other aspects of the module shown in FIGS. 38A–C.

FIG. 43 shows other aspects of the module shown in FIGS. 42A and 42B.

FIG. 50 is a screen face which shows a fluoroscopic image of bone in combination with computer generated images of axes and components in accordance with one embodiment of the present invention.

FIG. 58 is another view showing navigation and placement of a cutting block according to one embodiment of the present invention.

FIG. 72 is a screen face according to one embodiment of the present invention which contains images and textural suggestions for assisting in assessing performance and making adjustments to improve performance of a joint in accordance with one aspect of the invention.

DETAILED DESCRIPTION

Figure 1:
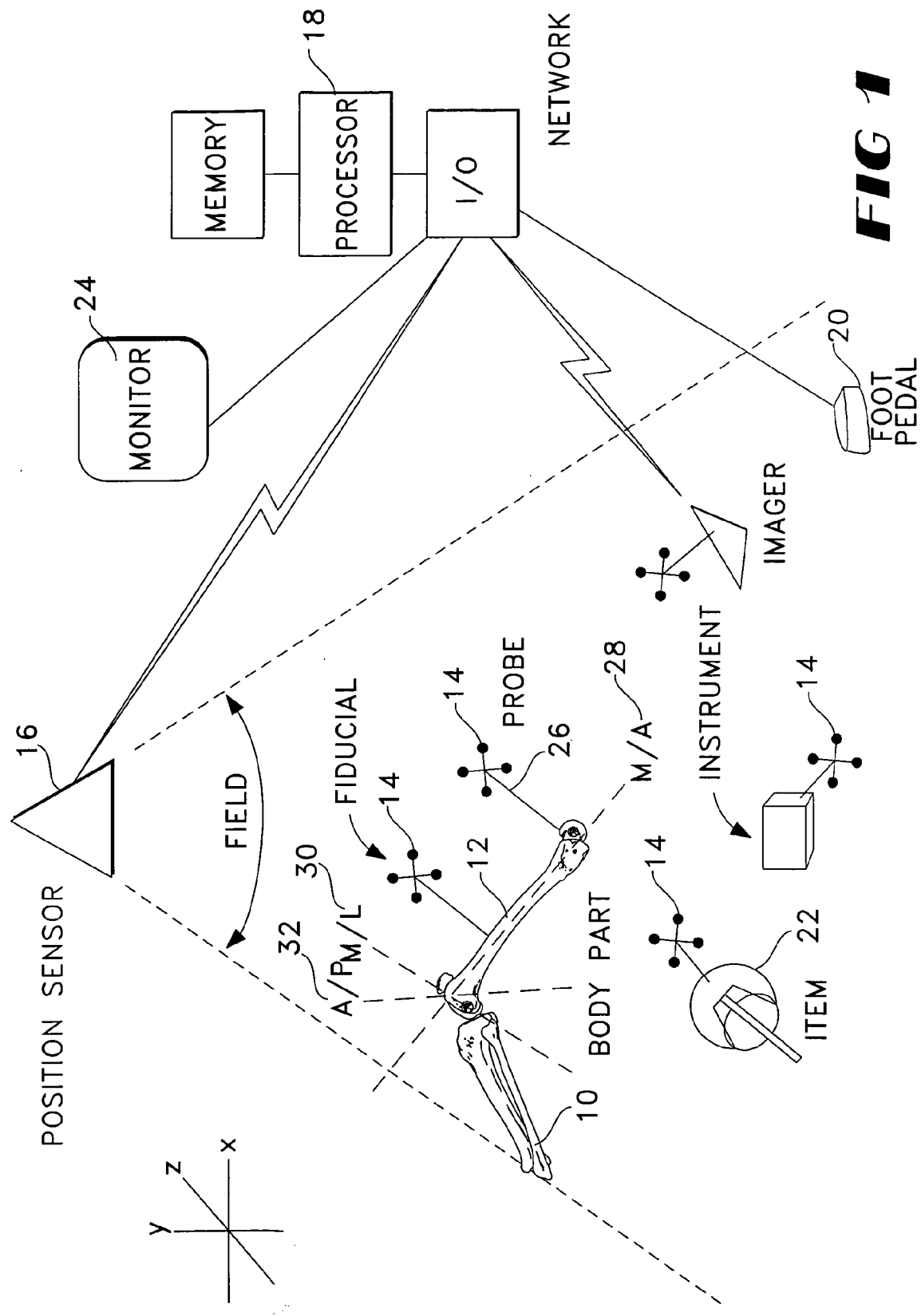
FIG. 1 is a schematic view of a particular embodiment of instrumentation, systems, and processes according to the present invention.

Instrumentation, systems, and processes according to a preferred embodiment of the present invention use computer capacity, including standalone and/or networked, to store data regarding spatial aspects of surgically related items and virtual constructs or references including body parts, implements, instrumentation, trial components, prosthetic components and rotational axes of body parts. Any or all of these may be physically or virtually connected to or incorporate any desired form of mark, structure, component, or other fiducial or reference device or technique which allows position and/or orientation of the item to which it is attached to be sensed and tracked, preferably in three dimensions of translation and three degrees of rotation as well as in time if desired. In the preferred embodiment, such "fidicuals" are reference frames each containing at least three, preferably four, sometimes more, reflective elements such as spheres reflective of lightwave or infrared energy, or active elements such as LEDs.

In a preferred embodiment, orientation of the elements on a particular fiducial varies from one fiducial to the next so that sensors according to the present invention may distinguish between various components to which the fiducials are attached in order to correlate for display and other purposes data files or images of the components. In a preferred embodiment of the present invention, some fiducials use reflective elements and some use active elements, both of which may be tracked by preferably two, sometimes more infrared sensors whose output may be processed in concert to geometrically calculate position and orientation of the item to which the fiducial is attached.

Position/orientation tracking sensors and fiducials need not be confined to the infrared spectrum. Any electromagnetic, electrostatic, light, sound, radiofrequency or other desired technique may be used. Alternatively, each item such as a surgical implement, instrumentation component, trial component, implant component or other device may contain its own "active" fiducial such as a microchip with appropriate field sensing or position/orientation sensing functionality and communications link such as spread spectrum RF link, in order to report position and orientation of the item. Such active fiducials, or hybrid active/passive fiducials such as transponders can be implanted in the body parts or in any of the surgically related devices mentioned above, or conveniently located at their surface or otherwise as desired. Fiducials may also take the form of conventional structures such as a screw driven into a bone, or any other three dimensional item attached to another item, position and orientation of such three dimensional item able to be tracked in order to track position and orientation of body parts and surgically related items. Hybrid fiducials may be partly passive, partly active such as inductive components or transponders which respond with a certain signal or data set when queried by sensors according to the present invention.

Instrumentation, systems, and processes according to a preferred embodiment of the present invention employ a computer to calculate and store reference axes of body components such as in a TKA, for example, the mechanical axis of the femur and tibia. From these axes such systems track the position of the instrumentation and osteotomy guides so that bone resections will locate the implant position optimally, usually aligned with the mechanical axis. Furthermore, during trial reduction of the knee, the systems provide feedback on the balancing of the ligaments in a range of motion and under varus/valgus, anterior/posterior and rotary stresses and can suggest or at least provide more accurate information than in the past about which ligaments the surgeon should release in order to obtain correct balancing, alignment and stability. Instrumentation, systems and processes according to the present invention allow the attachment of a variable alignment module so that a surgeon can grossly place a cutting block based on visual landmarks or navigation and then finely adjust the cutting block based on navigation and feedback from the system.

Instrumentation, systems, and processes according to the present invention can also suggest modifications to implant size, positioning, and other techniques to achieve optimal kinematics. Instrumentation, systems, and processes according to the present invention can also include databases of information regarding tasks such as ligament balancing, in order to provide suggestions to the surgeon based on performance of test results as automatically calculated by such instrumentation, systems, and processes.

FIG. 1 is a schematic view showing one embodiment of a system according to the present invention and one version of a setting according to the present invention in which surgery on a knee, in this case a Total Knee Arthroplasty, may be performed. Instrumentation, systems, and processes according to the present invention can track various body parts such as tibia 10 and femur 12 to which fiducials of the sort described above or any other sort may be implanted, attached, or otherwise associated physically, virtually, or otherwise. In the embodiment shown in FIG. 1, fiducials 14 are structural frames some of which contain reflective elements, some of which contain LED active elements, some of which can contain both, for tracking using stereoscopic infrared sensors suitable, at least operating in concert, for sensing, storing, processing and/or outputting data relating to ("tracking") position and orientation of fiducials 14 and thus components such as 10 and 12 to which they are attached or otherwise associated. Position sensor 16, as mentioned above, may be any sort of sensor functionality for sensing position and orientation of fiducials 14 and therefore items with which they are associated, according to whatever desired electrical, magnetic, electromagnetic, sound, physical, radio frequency, or other active or passive technique. In the preferred embodiment, position sensor 16 is a pair of infrared sensors disposed on the order of a meter, sometimes more, sometimes less, apart and whose output can be processed in concert to provide position and orientation information regarding fiducials 14.

In the embodiment shown in FIG. 1, computing functionality 18 can include processing functionality, memory functionality, input/output functionality whether on a standalone or distributed basis, via any desired standard, architecture, interface and/or network topology. In this embodiment, computing functionality 18 is connected to a monitor on which graphics and data may be presented to the surgeon during surgery. The screen preferably has a tactile interface so that the surgeon may point and click on screen for tactile screen input in addition to or instead of, if desired, keyboard and mouse conventional interfaces. Additionally, a foot pedal 20 or other convenient interface may be coupled to functionality 18 as can any other wireless or wireline interface to allow the surgeon, nurse or other desired user to control or direct functionality 18 in order to, among other things, capture position/orientation information when certain components are oriented or aligned properly. Items 22 such as trial components and instrumentation components may be tracked in position and orientation relative to body parts 10 and 12 using fiducials 14.

Computing functionality 18 can process, store and output on monitor 24 and otherwise various forms of data which correspond in whole or part to body parts 10 and 12 and other components for item 22. For example, in the embodiment shown in FIG. 1, body parts 10 and 12 are shown in cross-section or at least various internal aspects of them such as bone canals and surface structure are shown using fluoroscopic images. These images are obtained using a C-arm attached to a fiducial 14. The body parts, for example, tibia 10 and femur 12, also have fiducials attached. When the fluoroscopy images are obtained using the C-arm with fiducial 14, a position/orientation sensor 16 "sees" and tracks the position of the fluoroscopy head as well as the positions and orientations of the tibia 10 and femur 12. The computer stores the fluoroscopic images with this position/orientation information, thus correlating position and orientation of the fluoroscopic image relative to the relevant body part or parts. Thus, when the tibia 10 and corresponding fiducial 14 move, the computer automatically and correspondingly senses the new position of tibia 10 in space and can correspondingly move implements, instruments, references, trials and/or implants on the monitor 24 relative to the image of tibia 10. Similarly, the image of the body part can be moved, both the body part and such items may be moved, or the on screen image otherwise presented to suit the preferences of the surgeon or others and carry out the imaging that is desired. Similarly, when an item 22 such as an extramedullary rod 36 (See, e.g., FIG. 28), intramedullary rod, or other type of rod, that is being tracked moves, its image moves on monitor 24 so that the monitor shows the item 22 in proper position and orientation on monitor 24 relative to the femur 12. The rod 36 can thus appear on the monitor 24 in proper or improper alignment with respect to the mechanical axis and other features of the femur 12, as if the surgeon were able to see into the body in order to navigate and position rod 36 properly The computer functionality 18 can also store data relating to configuration, size and other properties of items 22 such as implements, instrumentation, trial components, implant components and other items used in surgery. When those are introduced into the field of position/orientation sensor 16, computer functionality 18 can generate and display overlain or in combination with the fluoroscopic images of the body parts 10 and 12, computer generated images of implements, instrumentation components, trial components, implant components and other items 22 for navigation, positioning, assessment and other uses.

Additionally, computer functionality 18 can track any point in the position/orientation sensor 16 field such as by using a designator or a probe 26. The probe also can contain or be attached to a fiducial 14. The surgeon, nurse, or other user touches the tip of probe 26 to a point such as a landmark on bone structure and actuates the foot pedal 20 or otherwise instructs the computer 18 to note the landmark position. The position/orientation sensor 16 "sees" the position and orientation of fiducial 14 "knows" where the tip of probe 26 is relative to that fiducial 14 and thus calculates and stores, and can display on monitor 24 whenever desired and in whatever form or fashion or color, the point or other position designated by probe 26 when the foot pedal 20 is hit or other command is given. Thus, probe 26 can be used to designate landmarks on bone structure in order to allow the computer 18 to store and track, relative to movement of the bone fiducial 14, virtual or logical information such as mechanical axis 28, medial laterial axis 30 and anterior/posterior axis 32 of femur 12, tibia 10 and other body parts in addition to any other virtual or actual construct or reference.

Figure 2:
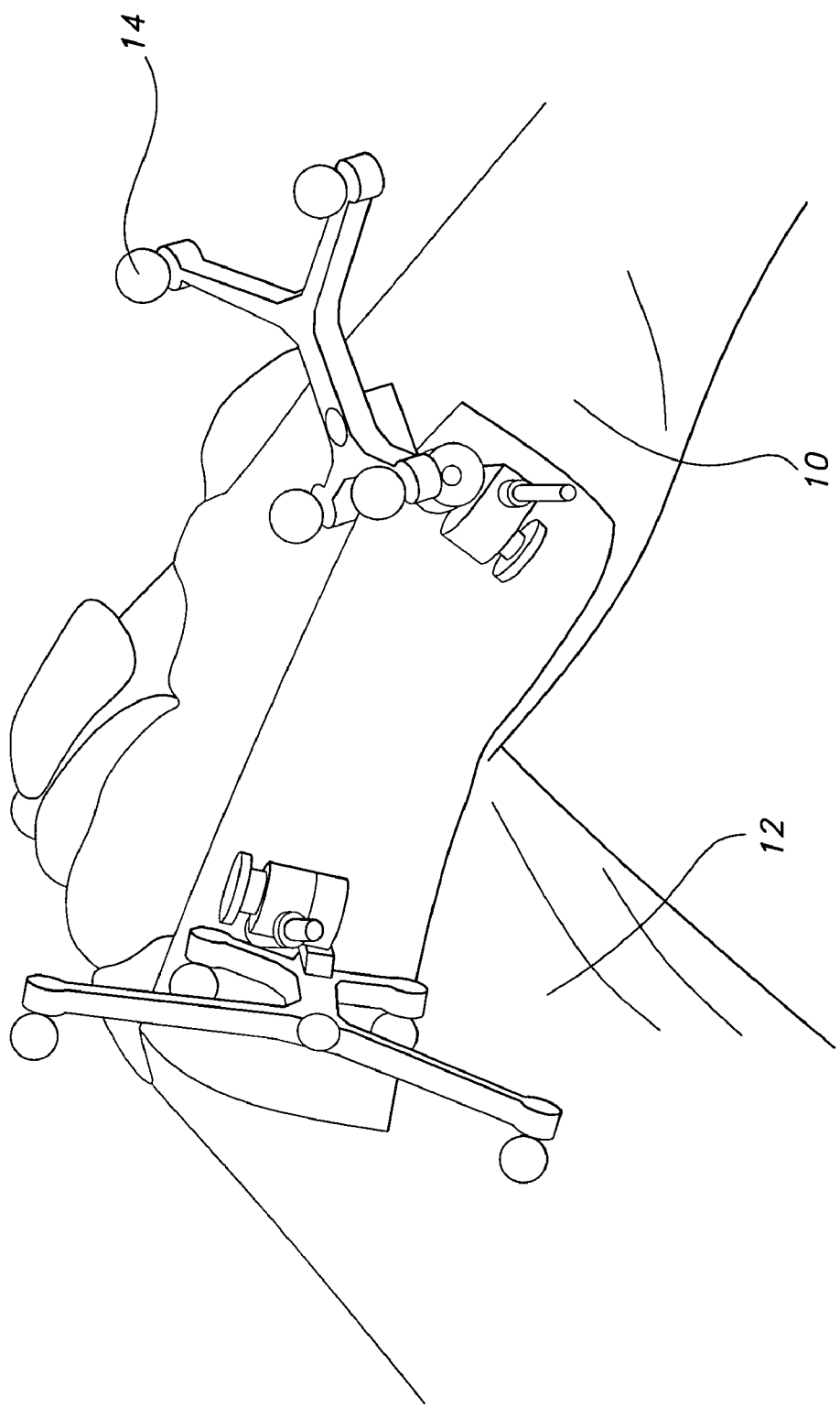
FIG. 2 is a view of a knee prepared for surgery, including a femur and a tibia, to which fiducials according to one embodiment of the present invention have been attached.
Figure 75:
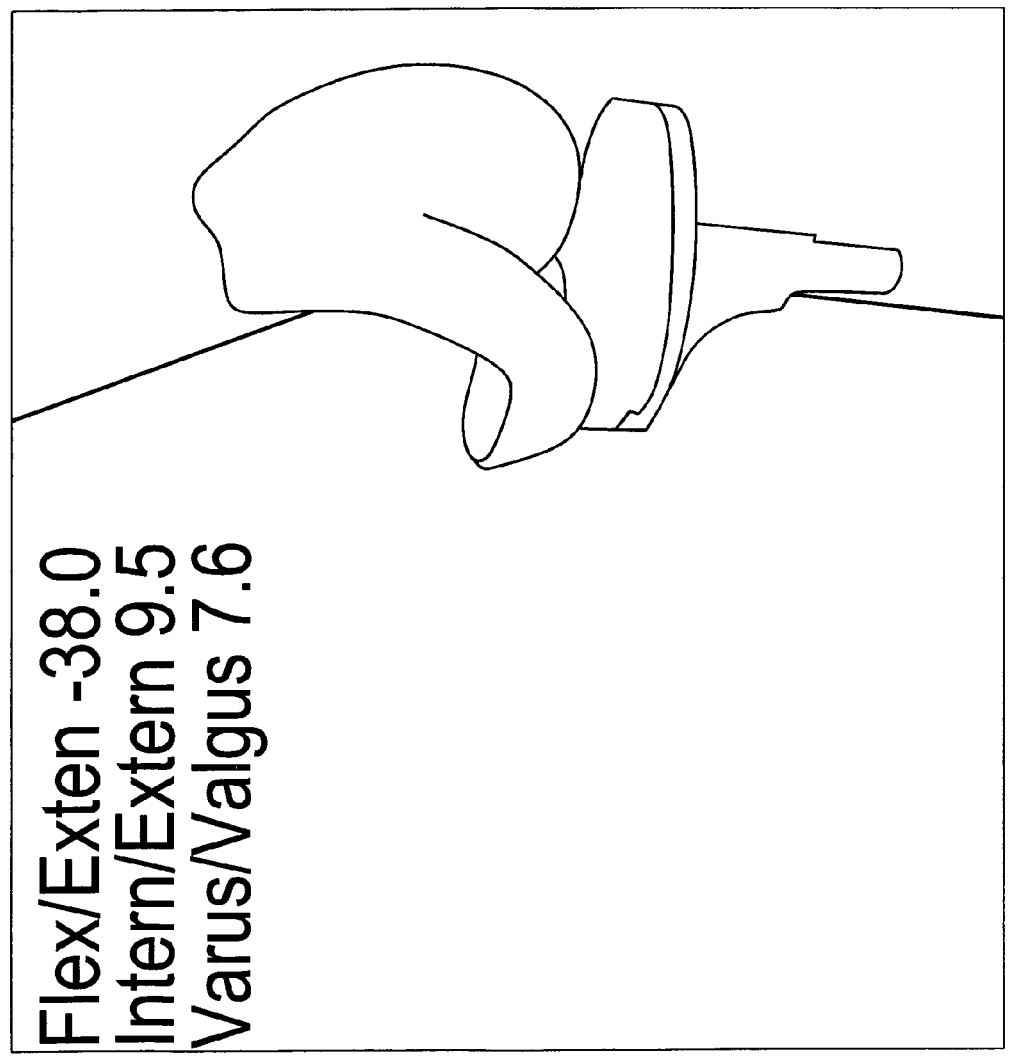
FIG. 75 is a computer generated graphic according to one embodiment of the present invention which allows visualization of trial or actual components installed in the bone structure according to one embodiment of the invention.

Instrumentation, systems, and processes according to an embodiment of the present invention such as the subject of FIGS. 2–75, can use the so-called FluoroNAV system and software provided by Medtronic Sofamor Danek Technologies. Such systems or aspects of them are disclosed in U.S. Pat. Nos. 5,383,454; 5,871,445; 6,146,390; 6,165,81; 6,235,038 and 6,236,875, and related (under 35 U.S.C. Section 119 and/or 120) patents, which are all incorporated herein by this reference. Any other desired systems can be used as mentioned above for imaging, storage of data, tracking of body parts and items and for other purposes. The FluoroNav system requires the use of reference frame type fiducials 14 which have four and in some cases five elements tracked by infrared sensors for position/orientation of the fiducials and thus of the body part, implement, instrumentation, trial component, implant component, or other device or structure being tracked. Such systems also use at least one probe 26 which the surgeon can use to select, designate, register, or otherwise make known to the system a point or points on the anatomy or other locations by placing the probe as appropriate and signaling or commanding the computer to note the location of, for instance, the tip of the probe. The FluoroNav system also tracks position and orientation of a C-arm used to obtain fluoroscopic images of body parts to which fiducials have been attached for capturing and storage of fluoroscopic images keyed to position/orientation information as tracked by the sensors 16. Thus, the monitor 24 can render fluoroscopic images of bones in combination with computer generated images of virtual constructs and references together with implements, instrumentation components, trial components, implant components and other items used in connection with surgery for navigation, resection of bone, assessment and other purposes.

Figure 3:
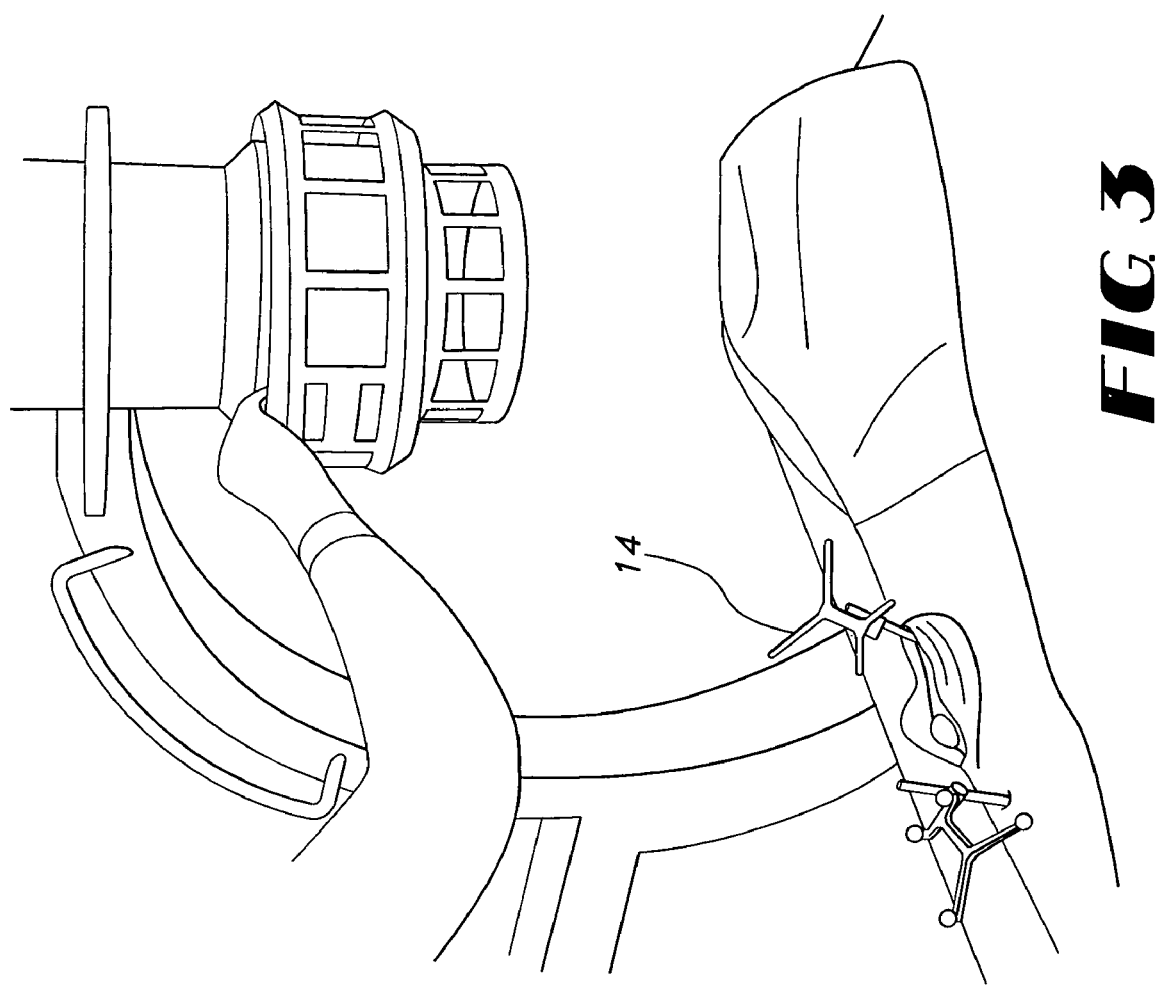
FIG. 3 is a view of a portion of a leg prepared for surgery according to the present invention with a C-arm for obtaining fluoroscopic images associated with a fiducial according to one embodiment of the present invention.

FIGS. 2–75 are various views associated with Total Knee Arthroplasty surgery processes according to one particular embodiment and version of the present invention being carried out with the FluoroNav system referred to above. FIG. 2 shows a human knee in the surgical field, as well as the corresponding femur and tibia, to which fiducials 14 have been rigidly attached in accordance with this embodiment of the invention. Attachment of fiducials 14 preferably is accomplished using structure that withstands vibration of surgical saws and other phenomenon which occur during surgery without allowing any substantial movement of fiducial 14 relative to body part being tracked by the system. FIG. 3 shows fluoroscopy images being obtained of the body parts with fiducials 14 attached. The fiducial 14 on the fluoroscopy head in this embodiment is a cylindrically shaped cage which contains LEDs or "active" emitters for tracking by the sensors 16. Fiducials 14 attached to tibia 10 and femur 12 can also be seen. The fiducial 14 attached to the femur 12 uses LEDs instead of reflective spheres and is thus active, fed power by the wire seen extending into the bottom of the image.

Figure 4:
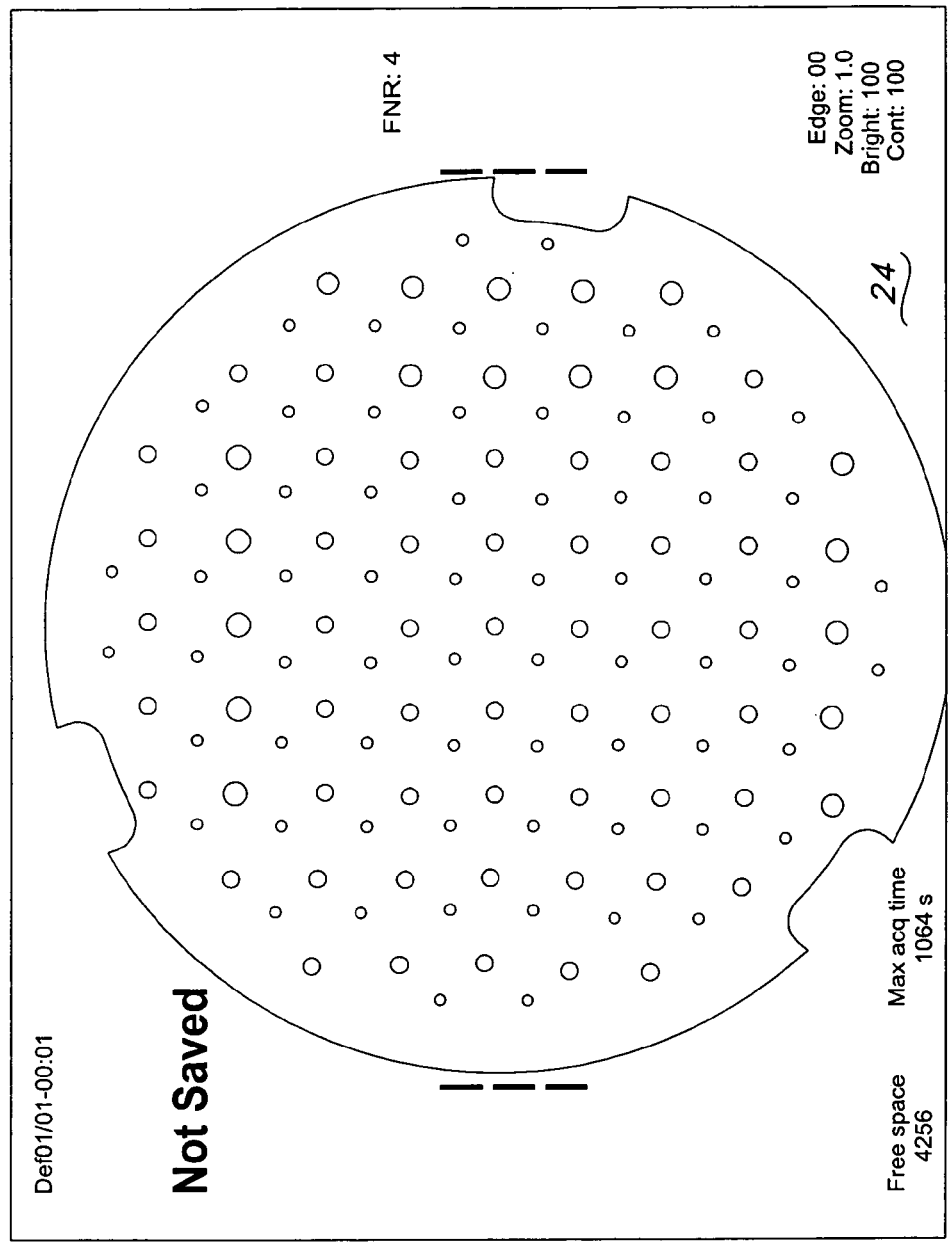
FIG. 4 is a fluoroscopic image of free space rendered on a monitor according to one embodiment of the present invention.
Figure 5:
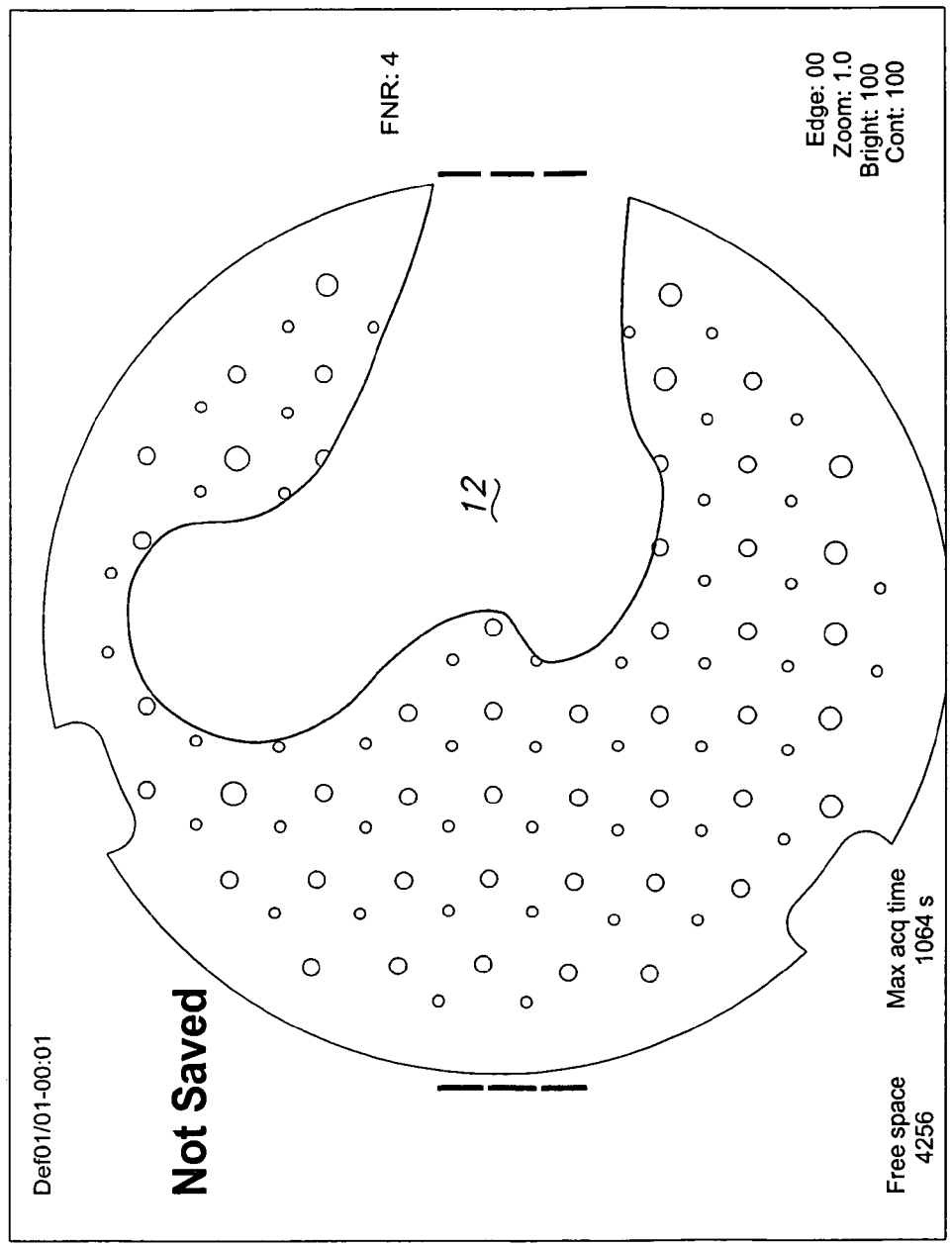
FIG. 5 is a fluoroscopic image of femoral head obtained and rendered according one embodiment of the present invention.

FIGS. 4–10 are fluoroscopic images shown on monitor 24 obtained with position and/or orientation information received by, noted and stored within computer 18. FIG. 4 is an open field with no body part image, but which shows the optical indicia which may be used to normalize the image obtained using a spherical fluoroscopy wave front with the substantially flat surface of the monitor 24. FIG. 5 shows an image of the femur 12 head. This image is taken in order to allow the surgeon to designate the center of rotation of the femoral head for purposes of establishing the mechanical axis and other relevant constructs relating to of the femur according to which the prosthetic components will ultimately be positioned. Such center of rotation can be established by articulating the femur within the acetabulum or a prosthesis to capture a number of samples of position and orientation information and thus in turn to allow the computer to calculate the average center of rotation. The center of rotation can be established by using the probe and designating a number of points on the femoral head and thus allowing the computer to calculate the geometrical center or a center which corresponds to the geometry of points collected. Additionally, graphical representations such as controllably sized circles displayed on the monitor can be fitted by the surgeon to the shape of the femoral head on planar images using tactile input on screen to designate the centers according to that graphic, such as are represented by the computer as intersection of axes of the circles. Other techniques for determining, calculating or establishing points or constructs in space, whether or not corresponding to bone structure, can be used in accordance with the present invention.

Figure 6:
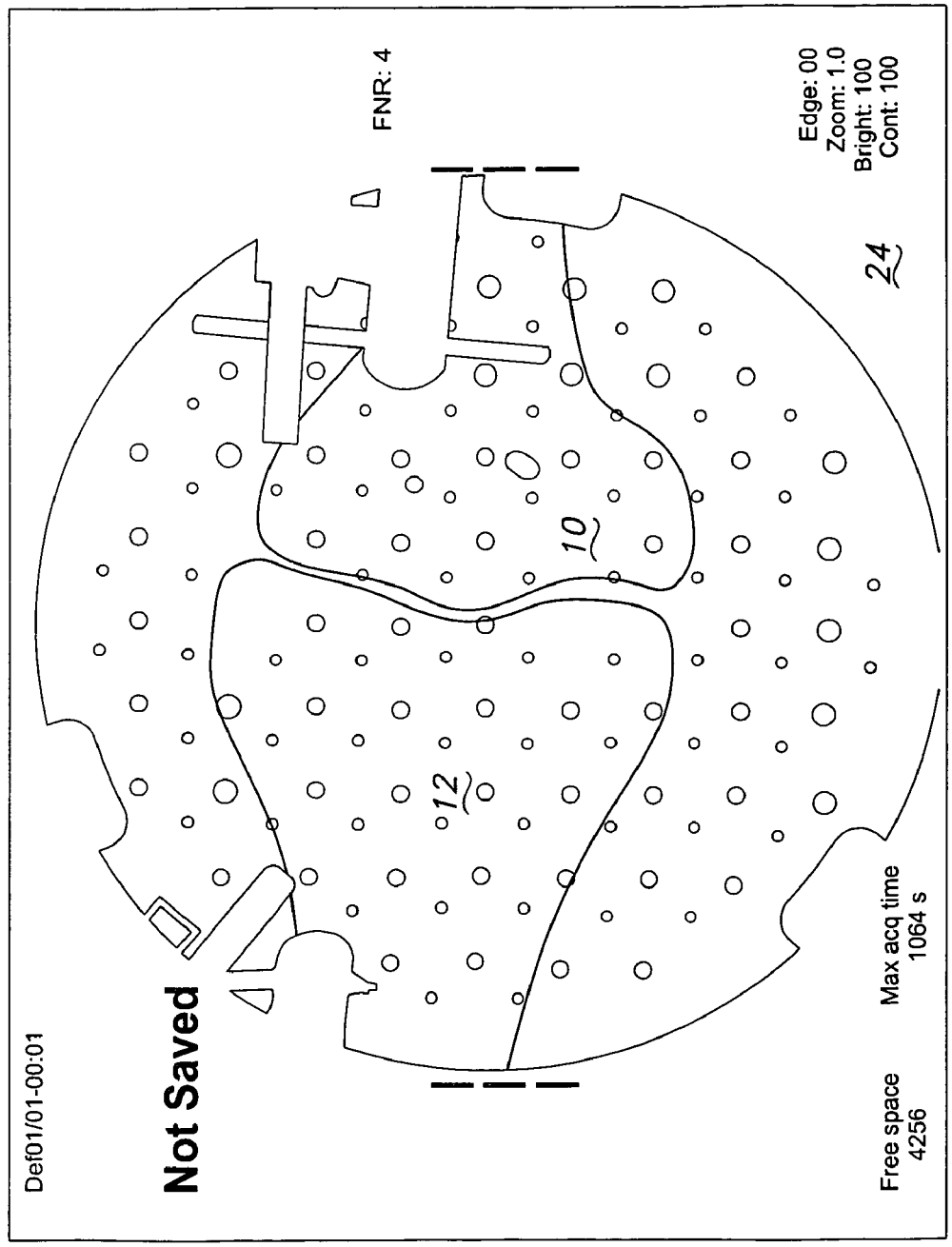
FIG. 6 is a fluoroscopic image of a knee obtained and rendered according to one embodiment of the present invention.
Figure 7:
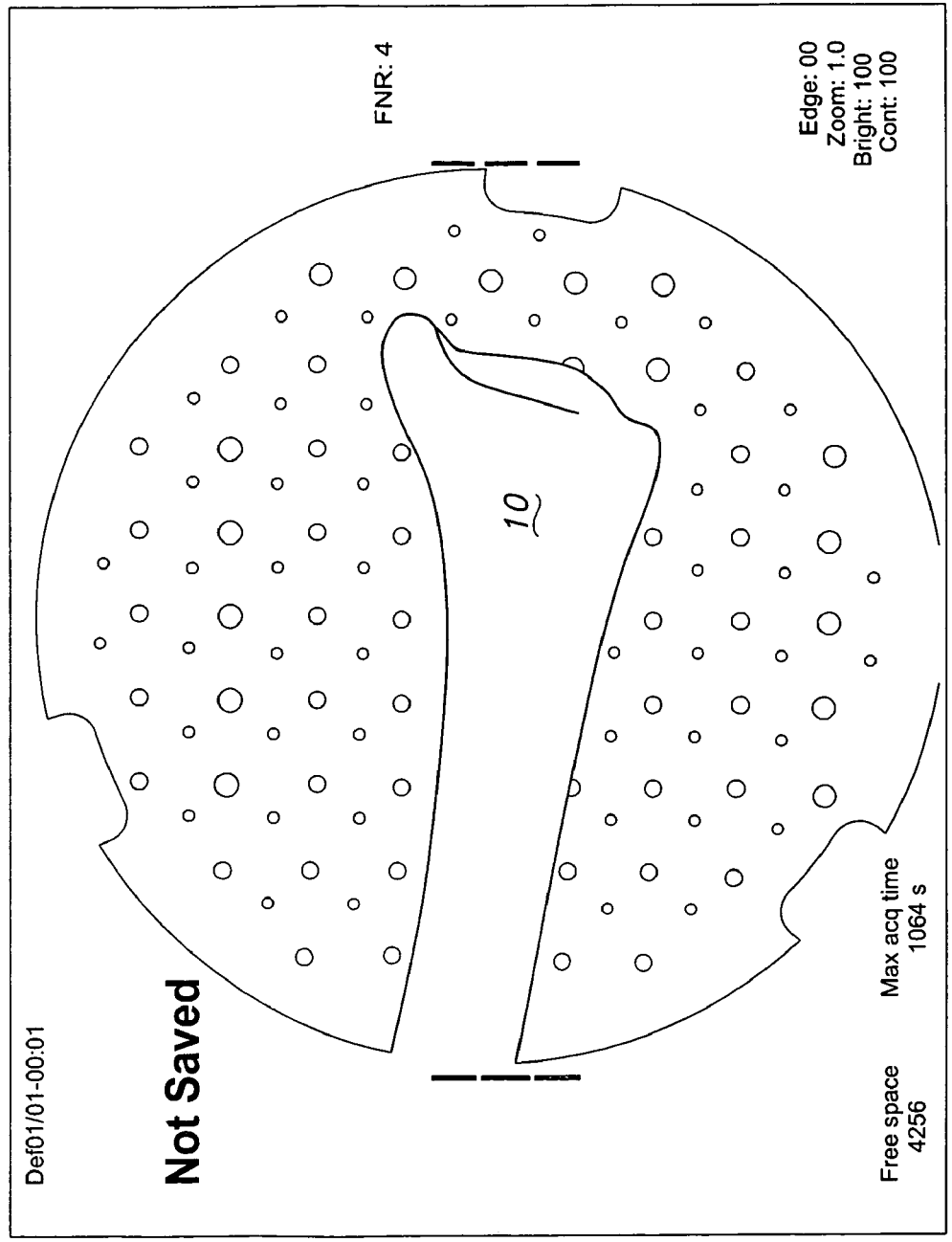
FIG. 7 is a fluoroscopic image of a tibia distal end obtained and rendered according to one embodiment of the present invention.
Figure 8:
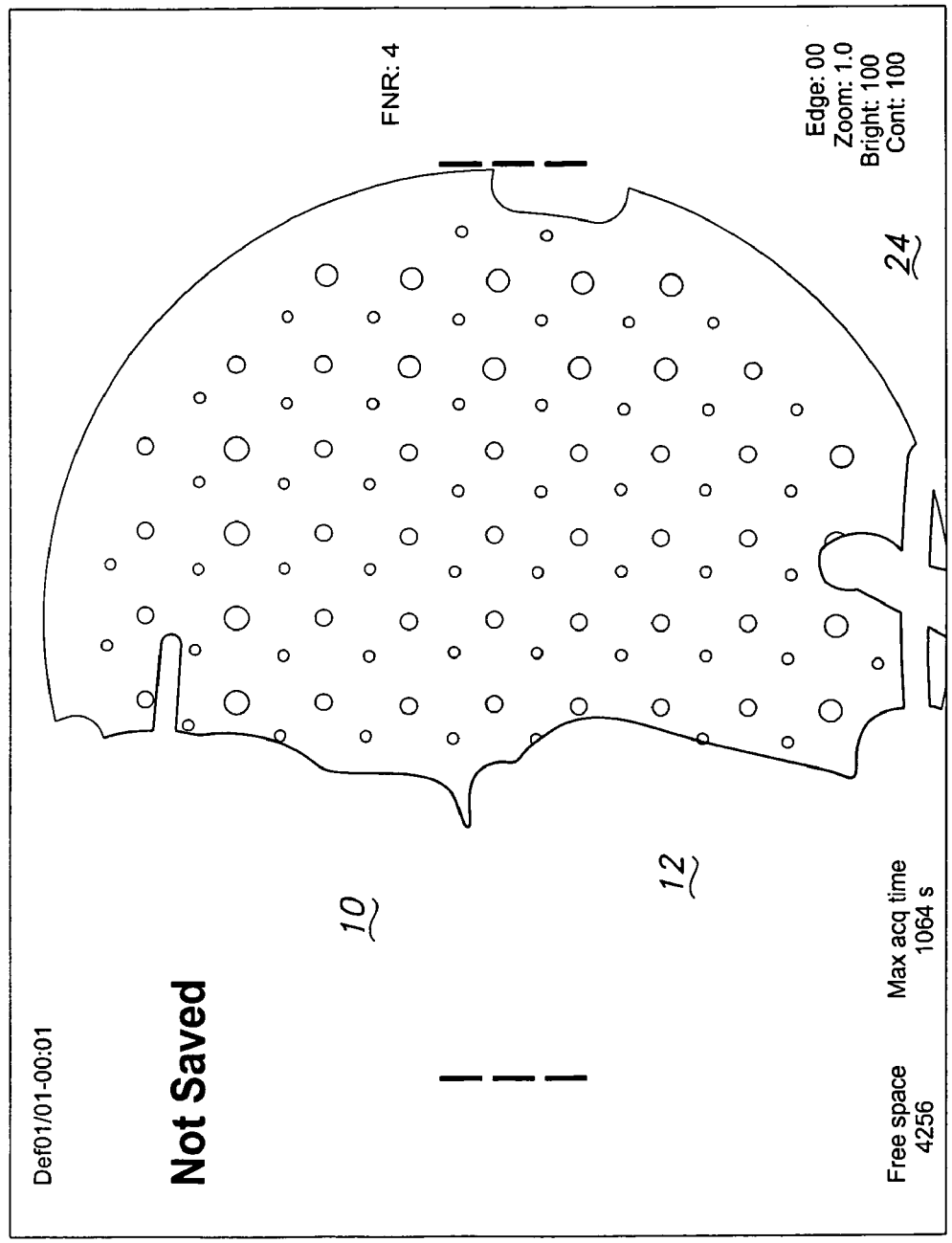
FIG. 8 is a fluoroscopic image of a lateral view of a knee obtained and rendered according to one embodiment of the present invention.
Figure 9:
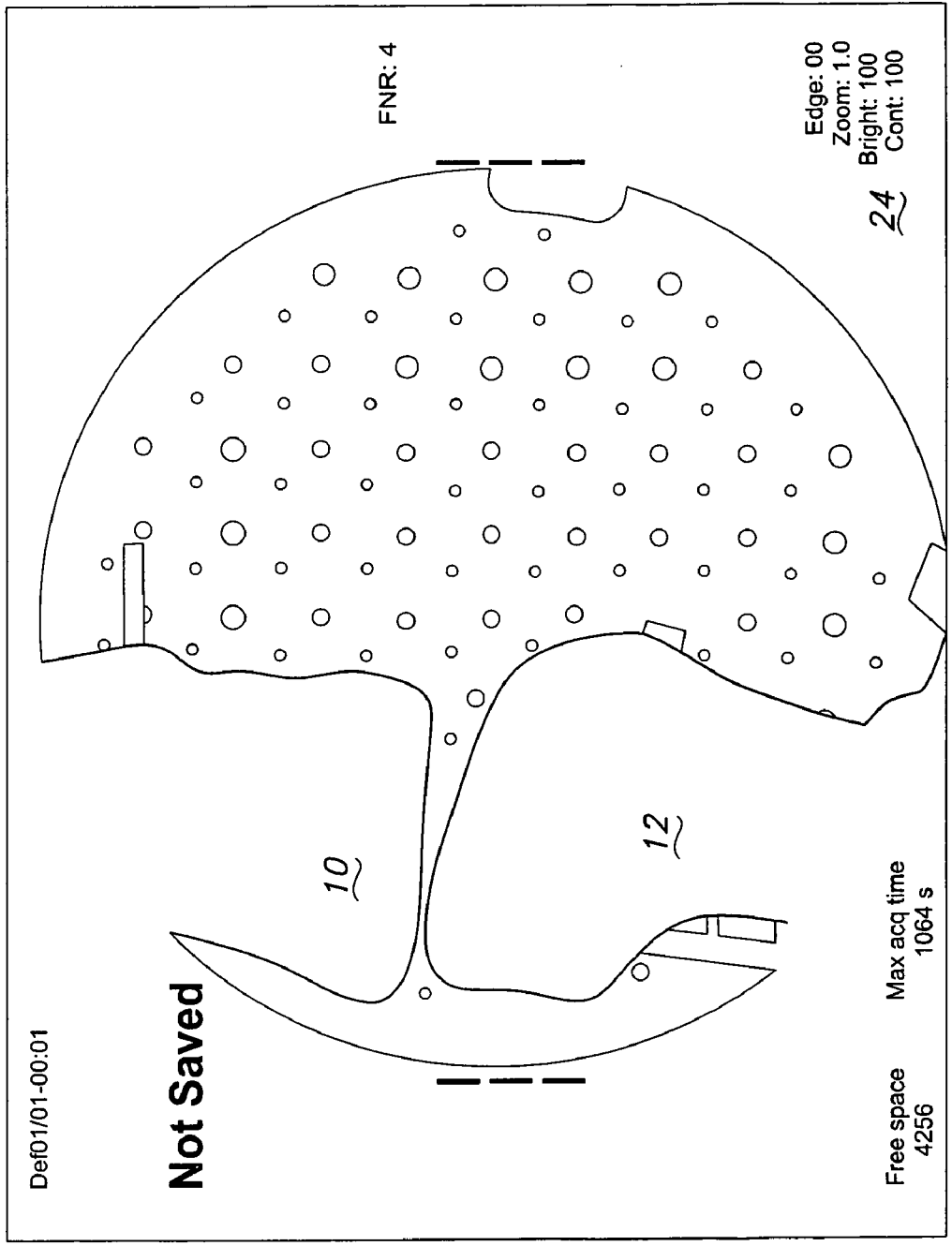
FIG. 9 is a fluoroscopic image of a lateral view of a knee obtained and rendered according to one embodiment of the present invention.
Figure 10:
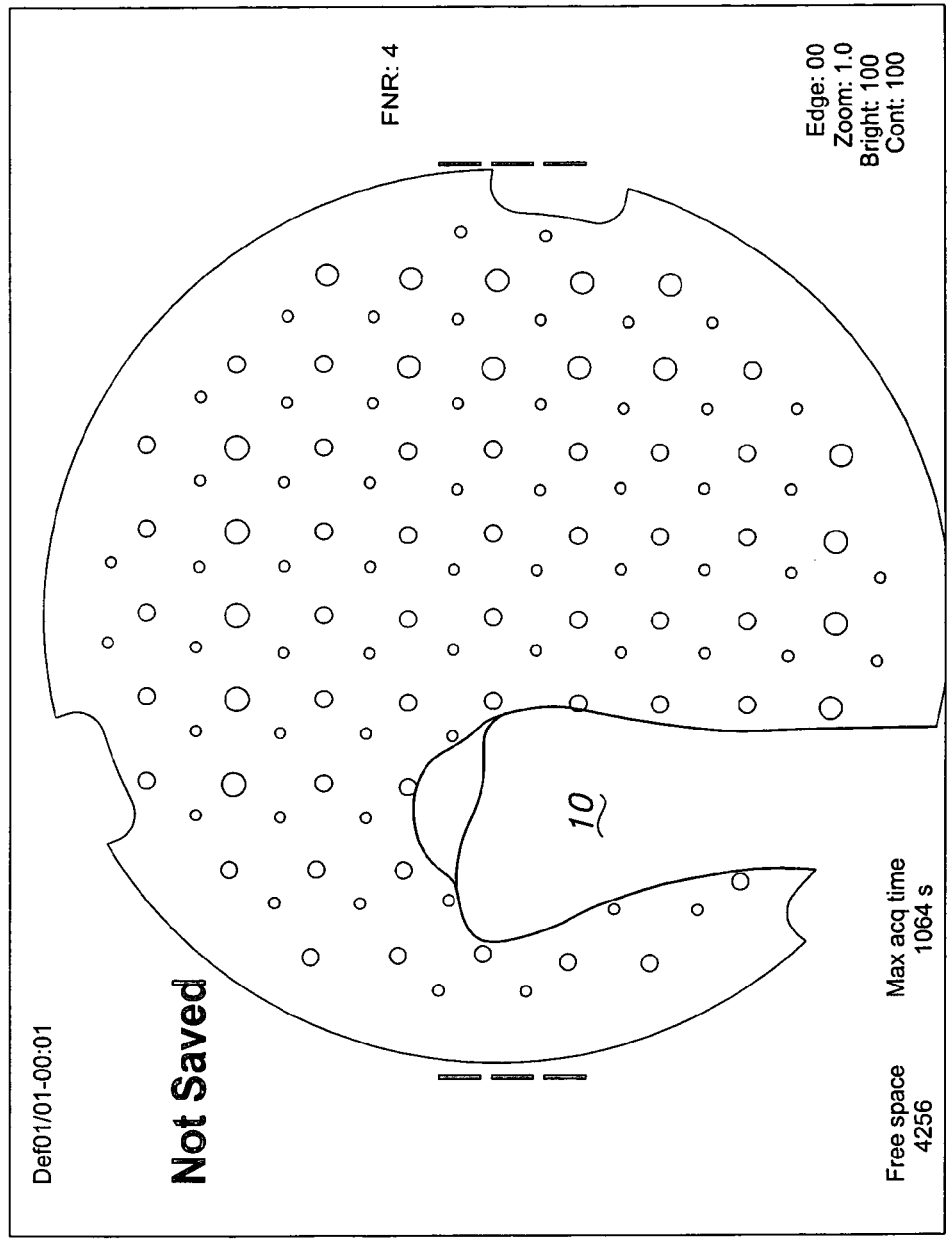
FIG. 10 is a fluoroscopic image of a lateral view of a tibia distal end obtained and rendered according to one embodiment of the present invention.

FIG. 5 shows a fluoroscopic image of the femoral head while FIG. 6 shows an anterior/posterior view of the knee which can be used to designate landmarks and establish axes or constructs such as the mechanical axis or other rotational axes. FIG. 7 shows the distal end of the tibia and FIG. 8 shows a lateral view of the knee. FIG. 9 shows another lateral view of the knee while FIG. 10 shows a lateral view of the distal end of the tibia.

Registration of Surgically Related Items

Figure 11:
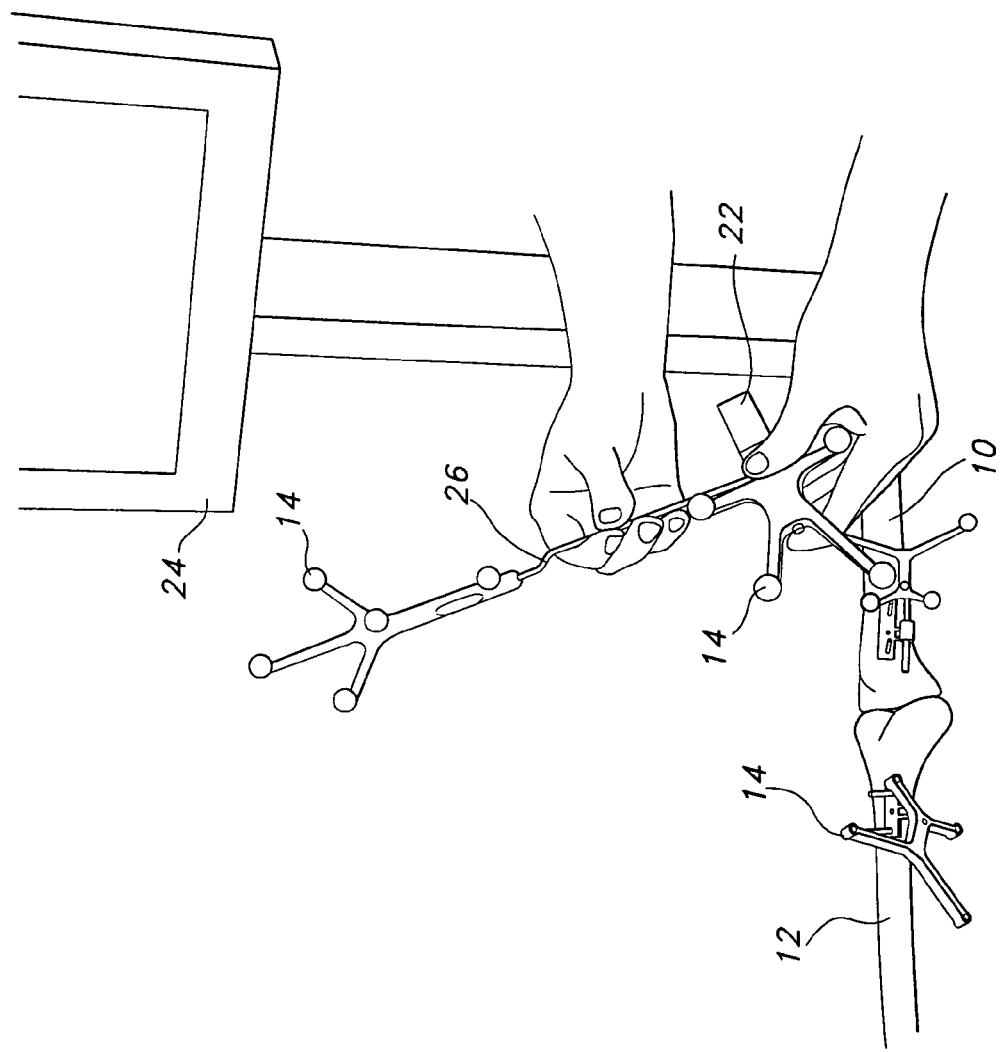
FIG. 11 shows a probe according to one embodiment of the present invention being used to register a surgically related component for tracking according to one embodiment of the present invention.
Figure 12:
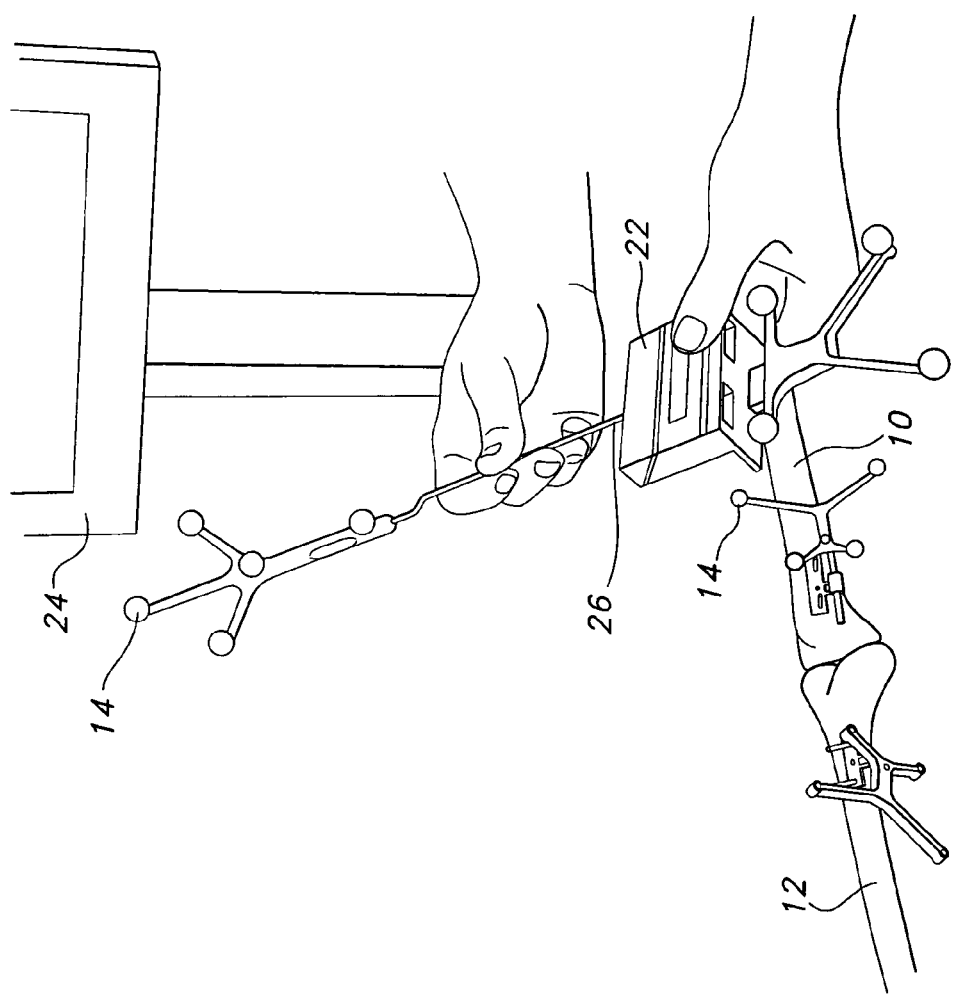
FIG. 12 shows a probe according to one embodiment of the present invention being used to register a cutting block for tracking according to one embodiment of the present invention.
Figure 13:
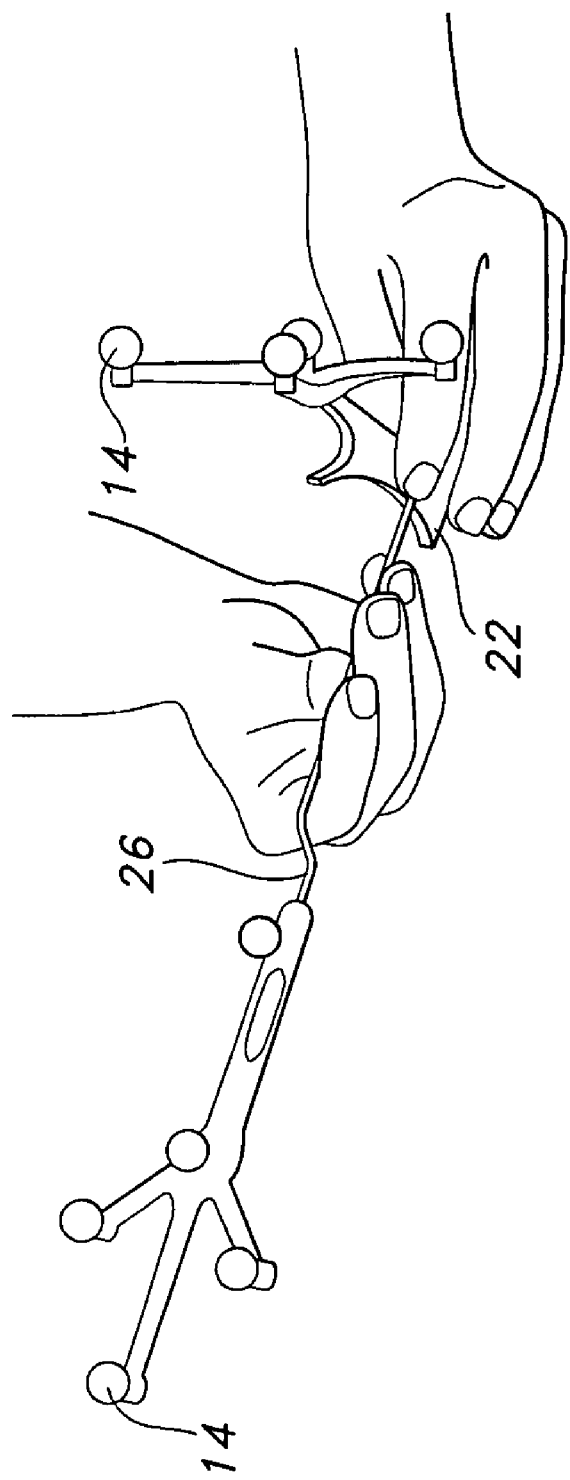
FIG. 13 shows a probe according to one embodiment of the present invention being used to register a tibial cutting block for tracking according to one embodiment of the present invention.
Figure 14:
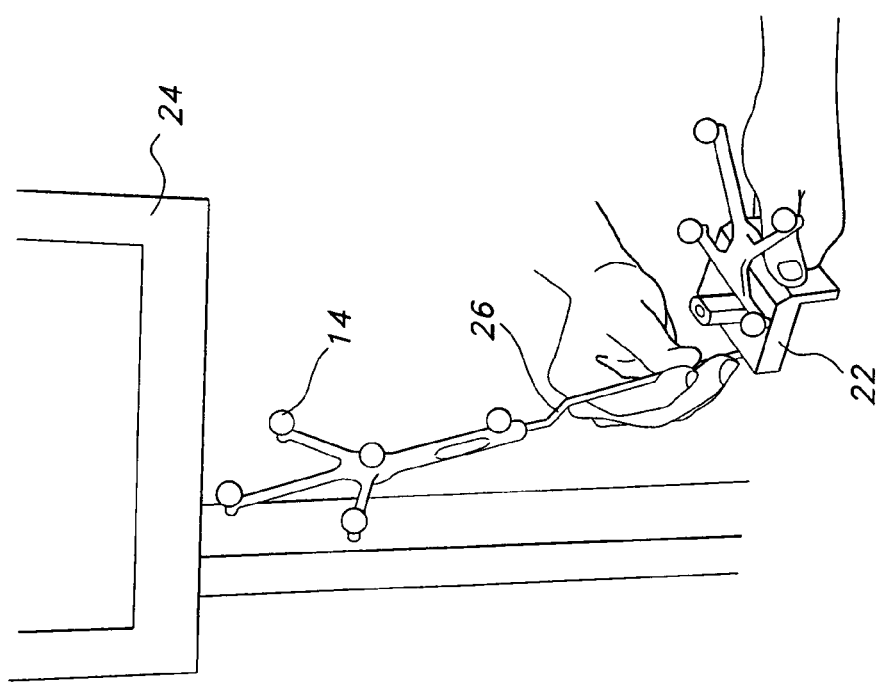
FIG. 14 shows a probe according to one embodiment of the present invention being used to register an alignment guide for tracking according to one embodiment of the present invention.

FIGS. 11–14 show designation or registration of items 22 which will be used in surgery. Registration simply means, however it is accomplished, ensuring that the computer knows which body part, item or construct corresponds to which fiducial or fiducials, and how the position and orientation of the body part, item or construct is related to the position and orientation of its corresponding fiducial or a fiducial attached to an impactor or other other component which is in turn attached to an item. Such registration or designation can be done before or after registering bone or body parts as discussed with respect to FIGS. 4–10. FIG. 11 shows a technician designating with probe 26 an item 22 such as an instrument component to which fiducial 14 is attached. The sensor 16 "sees" the position and orientation of the fiducial 14 attached to the item 22 and also the position and orientation of the fiducial 14 attached to the probe 26 whose tip is touching a landmark on the item 22. The technician designates onscreen or otherwise the identification of the item and then activates the foot pedal or otherwise instructs the computer to correlate the data corresponding to such identification, such as data needed to represent a particular cutting block component for a particular knee implant product, with the particularly shaped fiducial 14 attached to the component 22. The computer has then stored identification, position and orientation information relating to the fiducial for component 22 correlated with the data such as configuration and shape data for the item 22 so that upon registration, when sensor 16 tracks the item 22 fiducial 14 in the infrared field, monitor 24 can show the cutting block component 22 moving and turning, and properly positioned and oriented relative to the body part which is also being tracked. FIGS. 12–14 show similar registration for other instrumentation components 22.

Registration of Anatomy and Constructs

Figure 15:
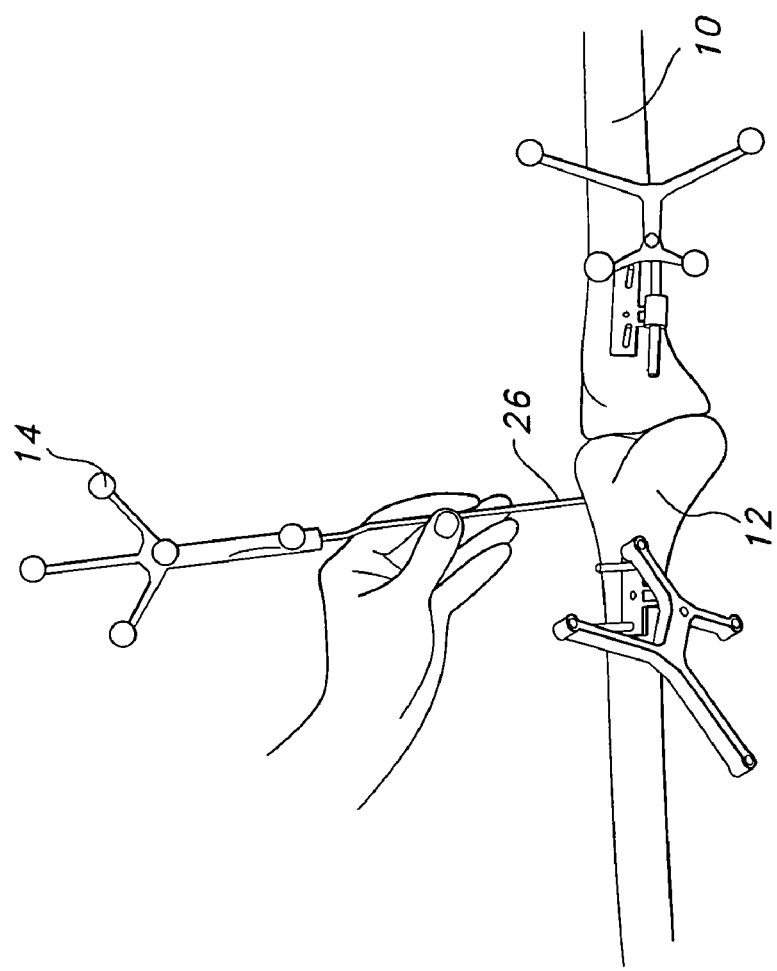
FIG. 15 shows a probe according to one embodiment of the present invention being used to designate landmarks on bone structure for tracking according one embodiment of the present invention.
Figure 16:
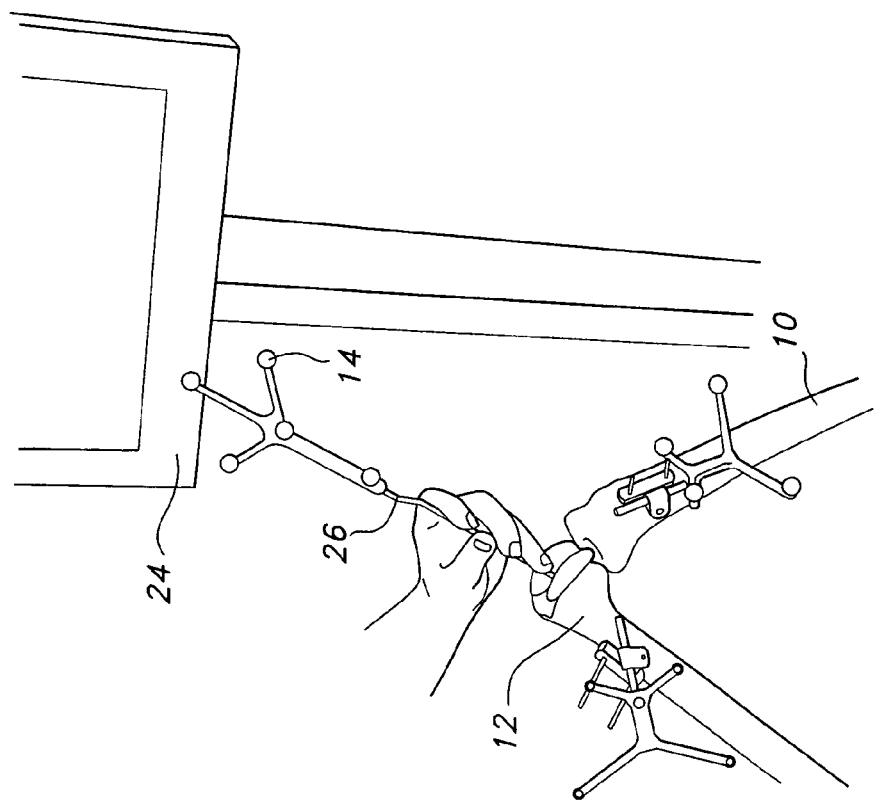
FIG. 16 is another view of a probe according to one embodiment of the present invention being used to designate landmarks on bone structure for tracking according one embodiment of the present invention.
Figure 17:
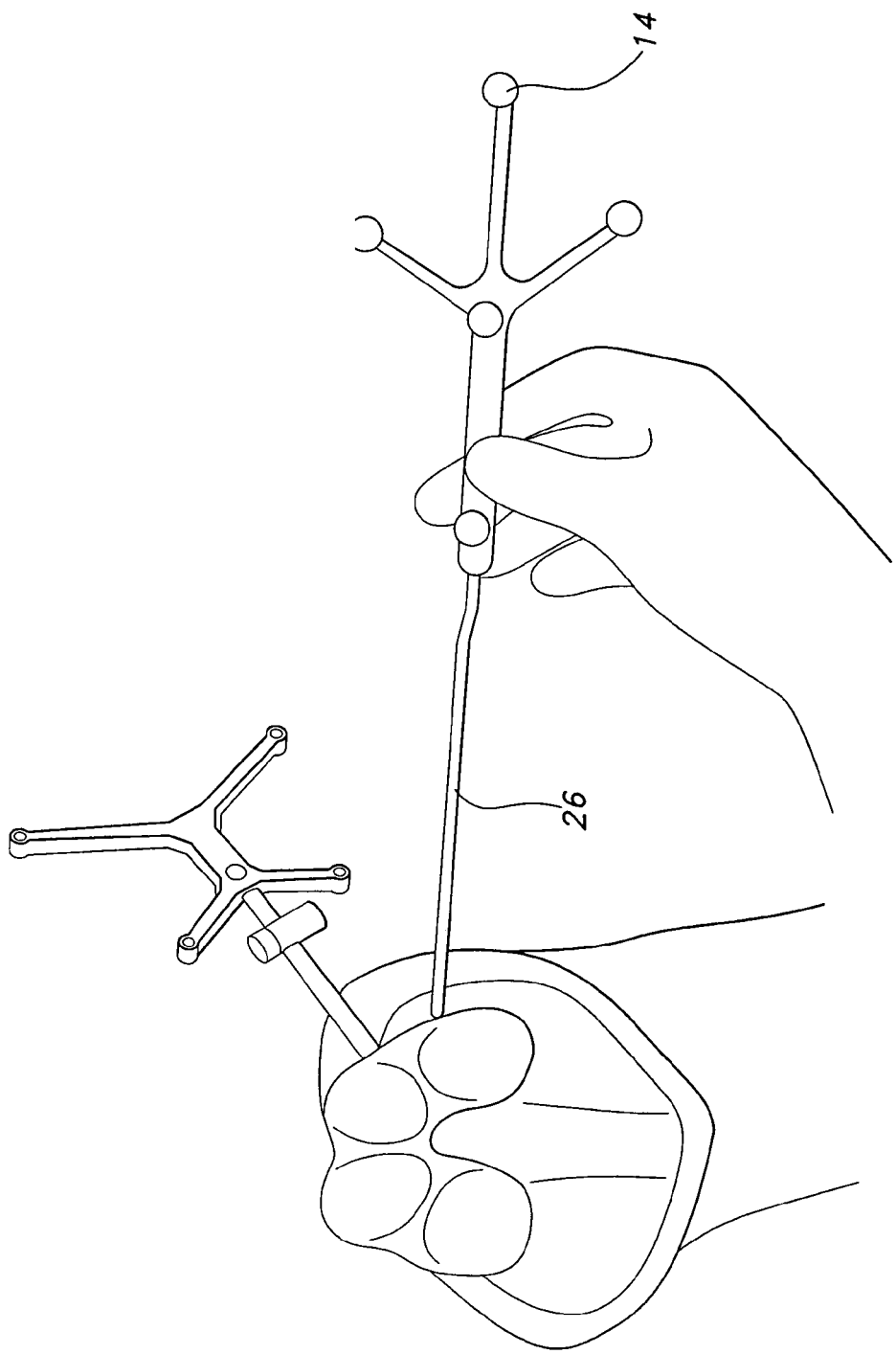
FIG. 17 is another view of a probe according to one embodiment of the present invention being used to designate landmarks on bone structure for tracking according one embodiment of the present invention.

Similarly, the mechanical axis and other axes or constructs of body parts 10 and 12 can also be "registered" for tracking by the system. Again, the system has employed a fluoroscope to obtain images of the femoral head, knee and ankle of the sort shown in FIGS. 4–10. The system correlates such images with the position and orientation of the C-arm and the patient anatomy in real time as discussed above with the use of fiducials 14 placed on the body parts before image acquisition and which remain in position during the surgical procedure. Using these images and/or the probe, the surgeon can select and register in the computer 18 the center of the femoral head and ankle in orthogonal views, usually anterior/posterior and lateral, on a touch screen. The surgeon uses the probe to select any desired anatomical landmarks or references at the operative site of the knee or on the skin or surgical draping over the skin, as on the ankle. These points are registered in three dimensional space by the system and are tracked relative to the fiducials on the patient anatomy which are preferably placed intraoperatively. FIG. 15 shows the surgeon using probe 26 to designate or register landmarks on the condylar portion of femur 12 using probe 26 in order to feed to the computer 18 the position of one point needed to determine, store, and display the epicondylar axis. (See FIG. 20 which shows the epicondylar axis and the anterior-posterior plane and for lateral plane.) Although registering points using actual bone structure such as in FIG. 15 is one preferred way to establish the axis, a cloud of points approach by which the probe 26 is used to designate multiple points on the surface of the bone structure can be employed, as can moving the body part and tracking movement to establish a center of rotation as discussed above. Once the center of rotation for the femoral head and the condylar component have been registered, the computer is able to calculate, store, and render, and otherwise use data for, the mechanical axis of the femur 12. FIG. 17 once again shows the probe 26 being used to designate points on the condylar component of the femur 12.

Figure 18:
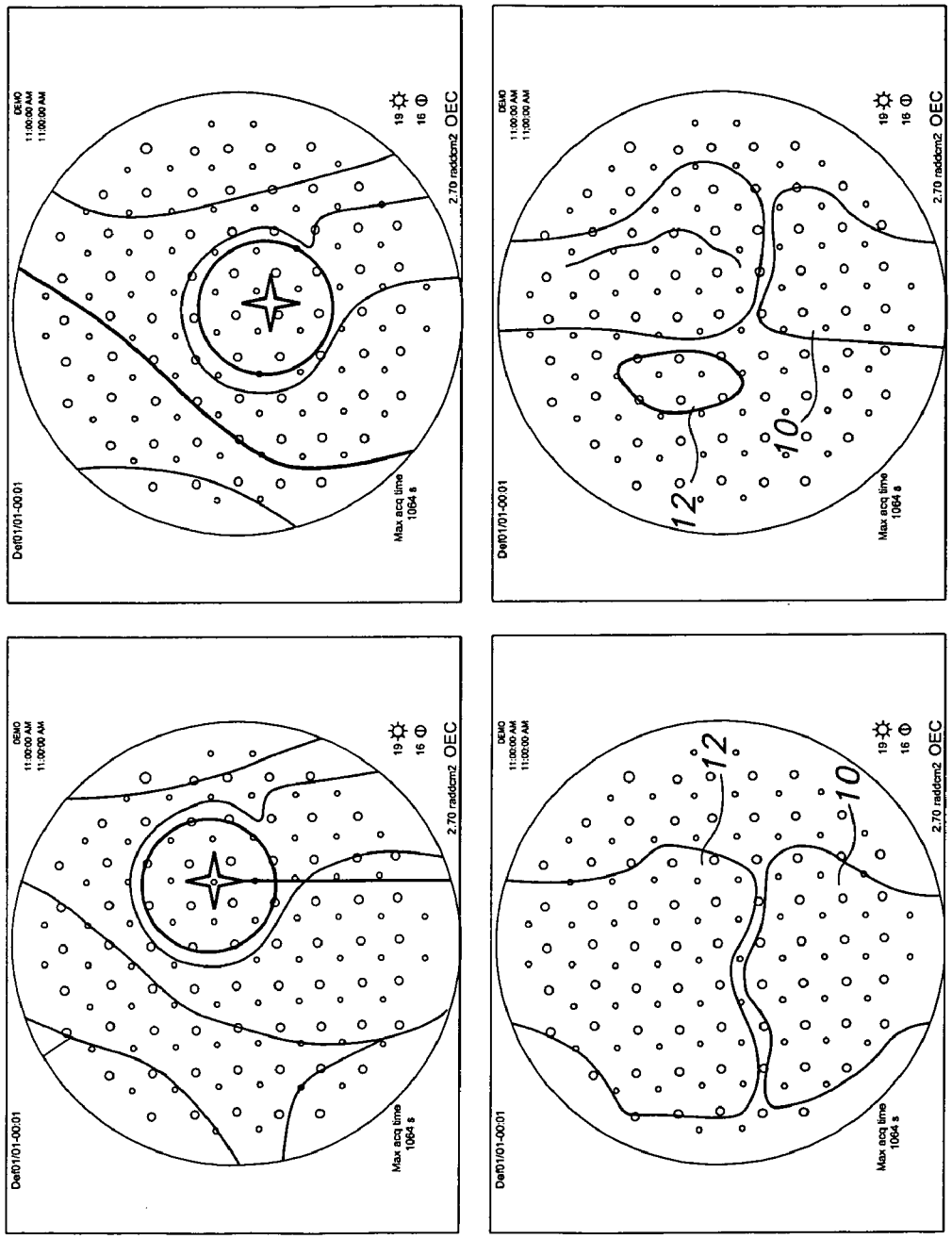
FIG. 18 is a screen face produced according to one embodiment of the present invention during designation of landmarks to determine a femoral mechanical axis.
Figure 19:
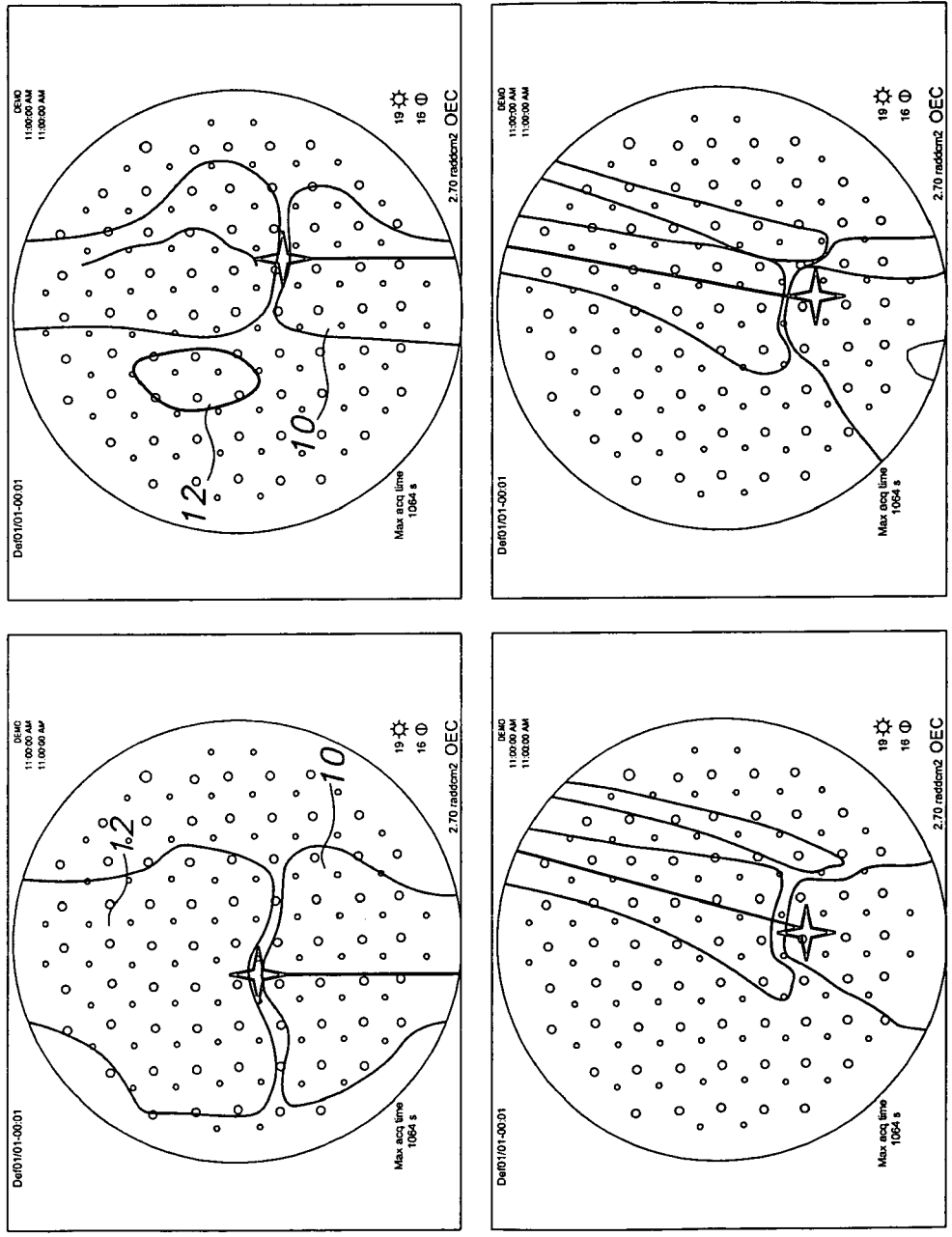
FIG. 19 is a view produced according to one embodiment of the present invention during designation of landmarks to determine a tibial mechanical axis.

FIG. 18 shows the onscreen images being obtained when the surgeon registers certain points on the bone surface using the probe 26 in order to establish the femoral mechanical axis. The tibial mechanical axis is then established by designating points to determine the centers of the proximal and distal ends of the tibia so that the mechanical axis can be calculated, stored, and subsequently used by the computer 18. FIG. 20 shows designated points for determining the epicondylar axis, both in the anterior/posterior and lateral planes while FIG. 21 shows such determination of the anterior-posterior axis as rendered onscreen. The posterior condylar axis is also determined by designating points or as otherwise desired, as rendered on the computer generated geometric images overlain or displayed in combination with the fluoroscopic images, all of which are keyed to fiducials 14 being tracked by sensors 16.

Figure 23:
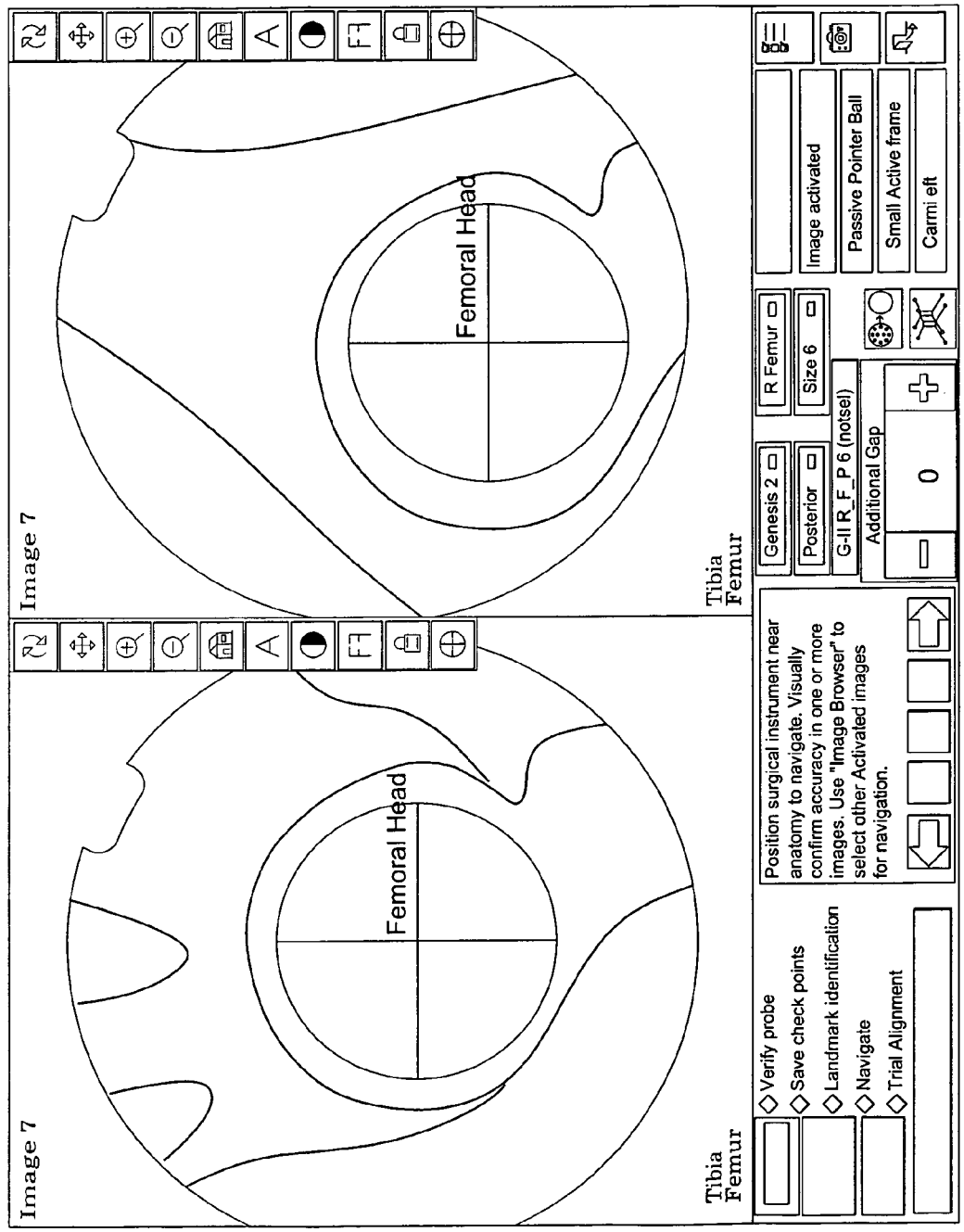
FIG. 23 is a screen face according to one embodiment of the present invention which presents graphic indicia which may be employed to help determine reference locations within bone structure.

FIG. 23 shows an adjustable circle graphic which can be generated and presented in combination with orthogonal fluoroscopic images of the femoral head, and tracked by the computer 18 when the surgeon moves it on screen in order to establish the centers of the femoral head in both the anterior-posterior and lateral planes.

Figure 24:
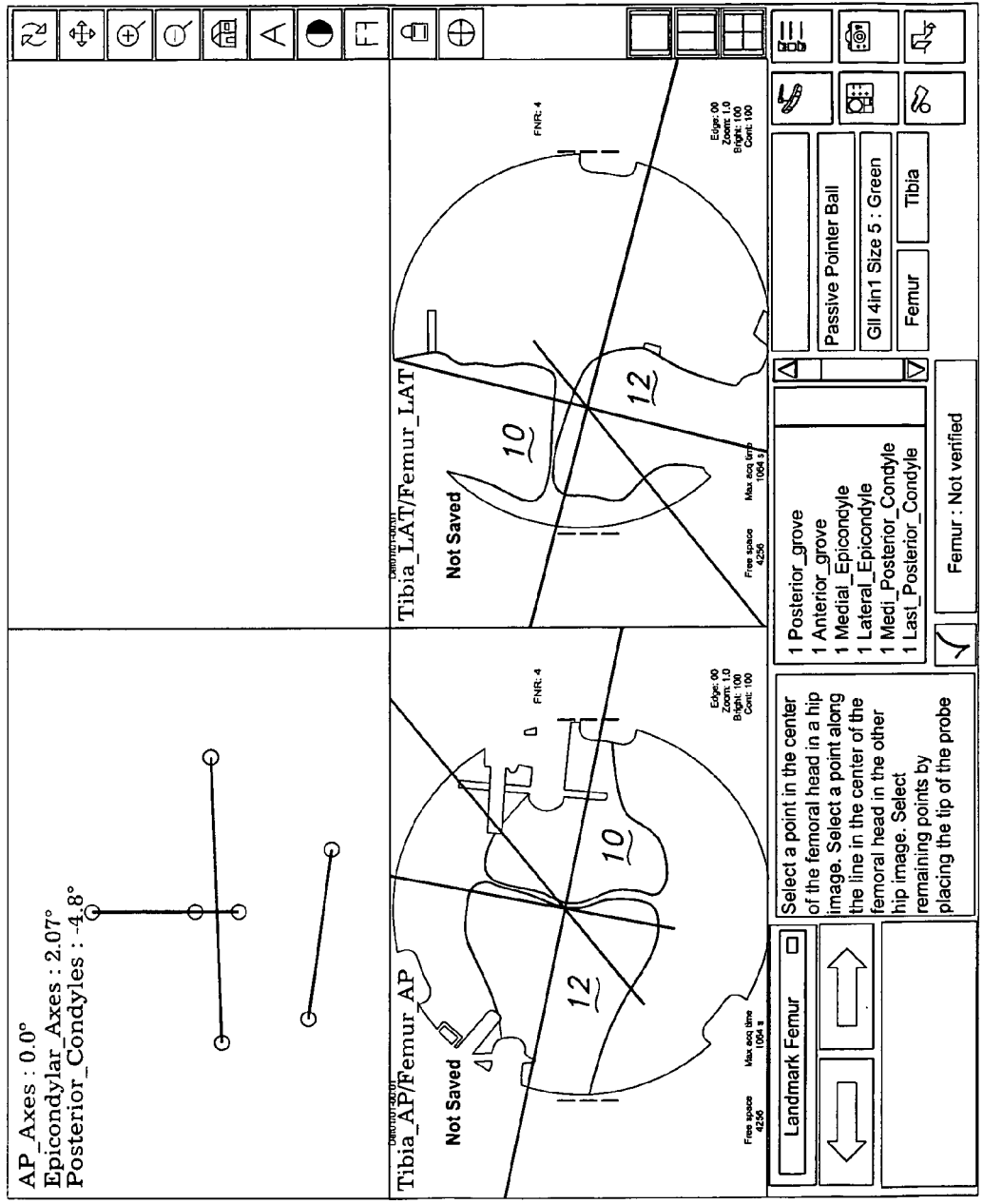
FIG. 24 is a screen face according to one embodiment of the present invention showing mechanical and other axes which have been established according to one embodiment of the present invention.

FIG. 24 is an onscreen image showing the anterior-posterior axis, epicondylar axis and posterior condylar axis from points which have been designated as described above. These constructs are generated by the computer 18 and presented on monitor 24 in combination with the fluoroscopic images of the femur 12, correctly positioned and oriented relative thereto as tracked by the system. In the fluoroscopic/computer generated image combination shown at left bottom of FIG. 24, a "sawbones" knee as shown in certain drawings above which contains radio opaque materials is represented fluoroscopically and tracked using sensor 16 while the computer generates and displays the mechanical axis of the femur 12 which runs generally horizontally. The epicondylar axis runs generally vertically, and the anterior/posterior axis runs generally diagonally. The image at bottom right shows similar information in a lateral view. Here, the anterior-posterior axis runs generally horizontally while the epicondylar axis runs generally diagonally, and the mechanical axis generally vertically.

FIG. 24, as is the case with a number of screen presentations generated and presented by the system of FIGS. 4–75, also shows at center a list of landmarks to be registered in order to generate relevant axes and constructs useful in navigation, positioning and assessment during surgery. Textual cues may also be presented which suggest to the surgeon next steps in the process of registering landmarks and establishing relevant axes. Such instructions may be generated as the computer 18 tracks, from one step to the next, registration of items 22 and bone locations as well as other measures being taken by the surgeon during the surgical operation.

Figure 25:
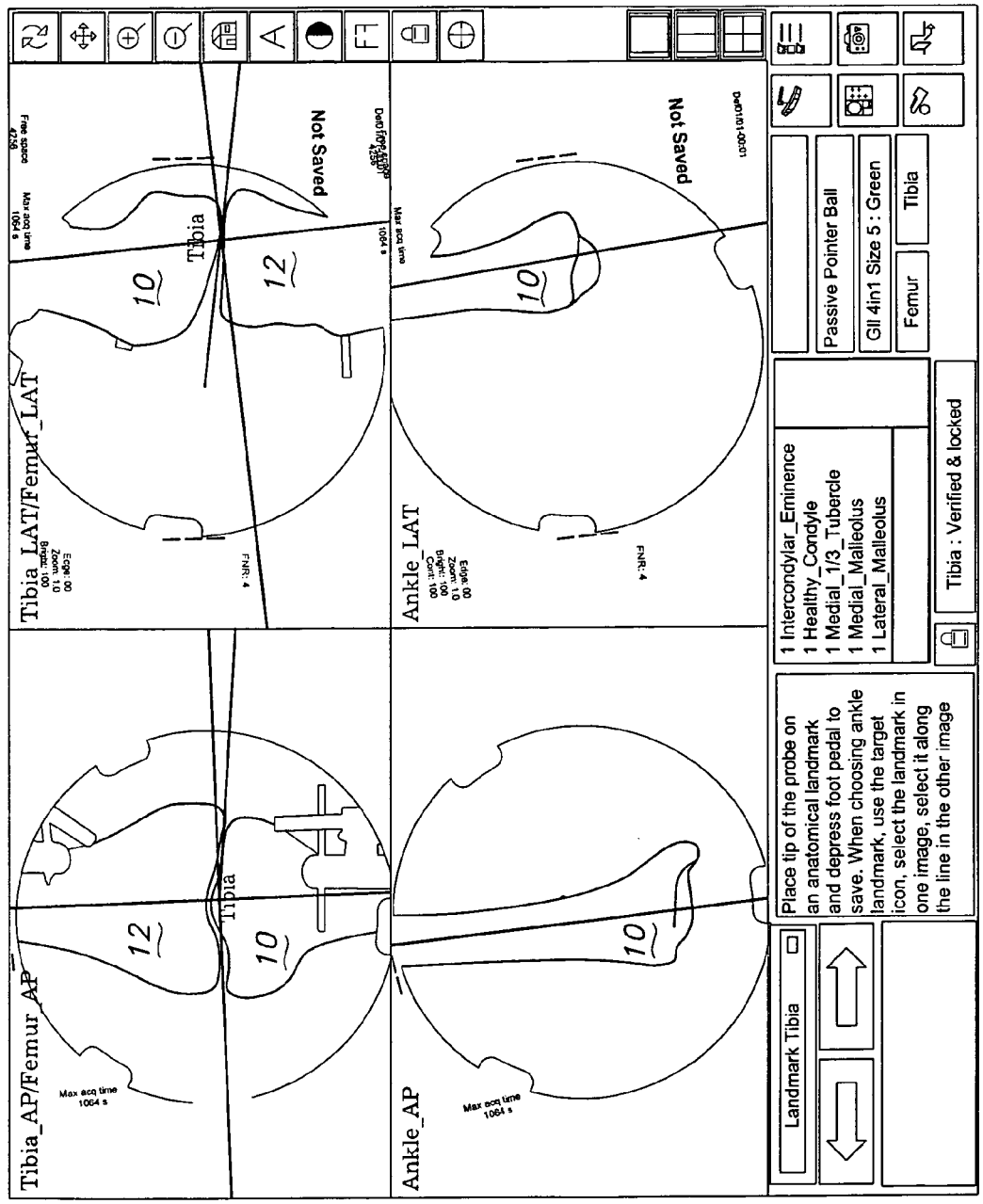
FIG. 25 is another screen face according to one embodiment of the present invention showing mechanical and other axes which have been established according to one embodiment of the present invention.

FIG. 25 shows mechanical, lateral, anterior-posterior axes for the tibia according to points are registered by the surgeon.

Figure 26:
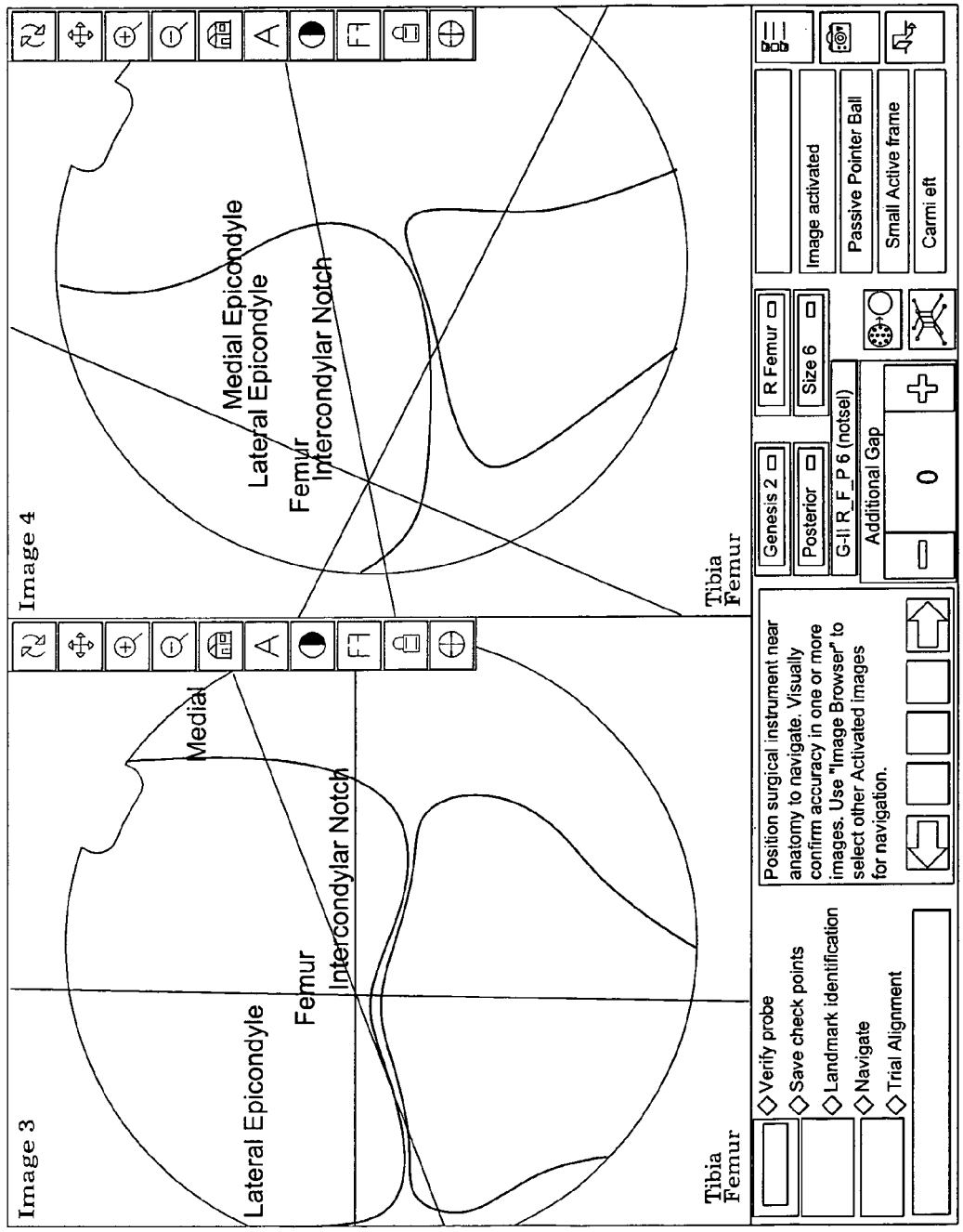
FIG. 26 is another screen face according to one embodiment of the present invention showing mechanical and other axes which have been established according to one embodiment of the present invention.

FIG. 26 is another onscreen image showing the axes for the femur 12.

Modifying Bone

After the mechanical axis and other rotation axes and constructs relating to the femur and tibia are established, instrumentation can be properly oriented to resect or modify bone in order to fit trial components and implant components properly according to the embodiment of the invention shown in FIGS. 4–75. Instrumentation such as, for instance, cutting blocks 34, to which fiducials 14 are mounted, can be employed. The system can then track cutting block 34 as the surgeon manipulates it for optimum positioning. In other words, the surgeon can "navigate" the cutting block 34 for optimum positioning using the system, the monitor, visual landmarks, and other devices, such as variable alignment modules 54. In this manner, instrumentation may be positioned according to the system of this embodiment in order to align the ostetomies to the mechanical and rotational axes or reference axes on an extramedullary rod 36 or any other structure that allows the instrumentation to be positioned without invading the medullary canal. The touchscreen 24 can then also display the instrument, such as the cutting block 34 and/or the implant and/or the variable alignment module 54 relative to the instruments and the rod 36 during this process, in order, among other things, properly to select size of implant and perhaps implant type. As the instrument moves, the varus/valgus, flexion/extension and internal/external rotation of the relative component position can be calculated and shown with respect to the referenced axes; in the preferred embodiment, this can be done at a rate of six cycles per second or faster. The instrument position is then fixed in the computer and physically and the bone resections are made.

Figure 27:
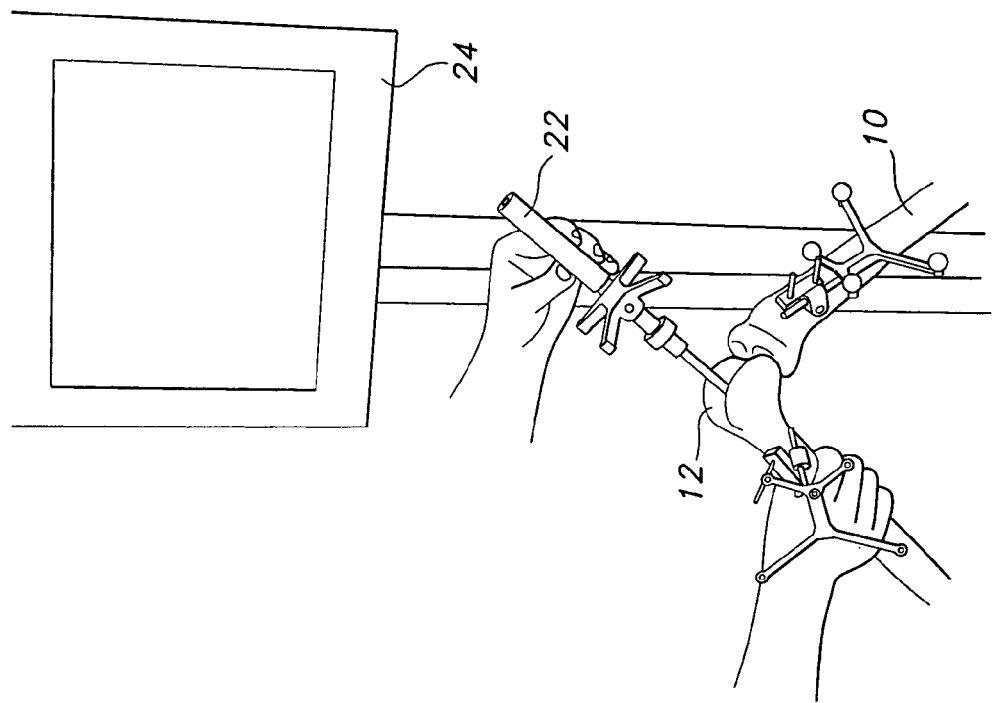
FIG. 27 shows navigation and placement of an extramedullary rod according to one embodiment of the present invention.
Figure 32:
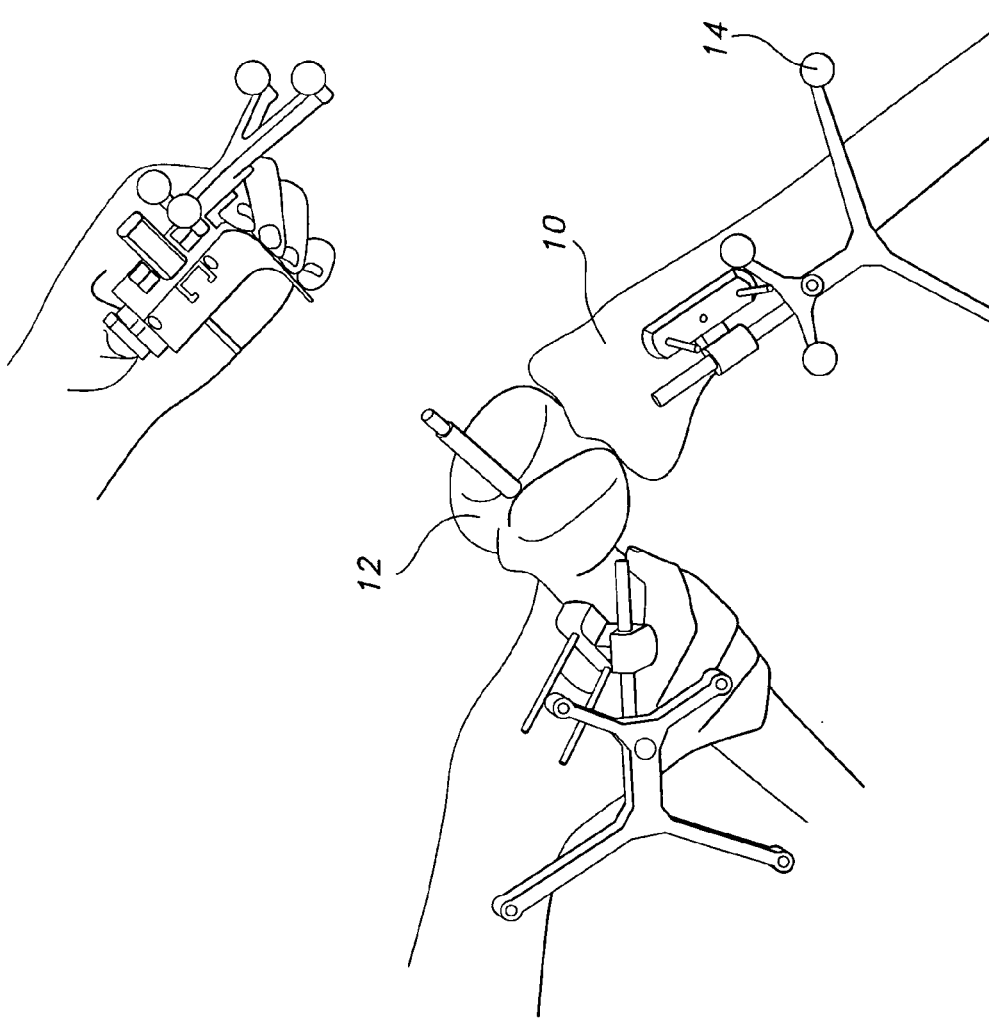
FIG. 32 is a view which shows navigation and placement of an alignment guide according to one embodiment of the present invention.
Figure 33:
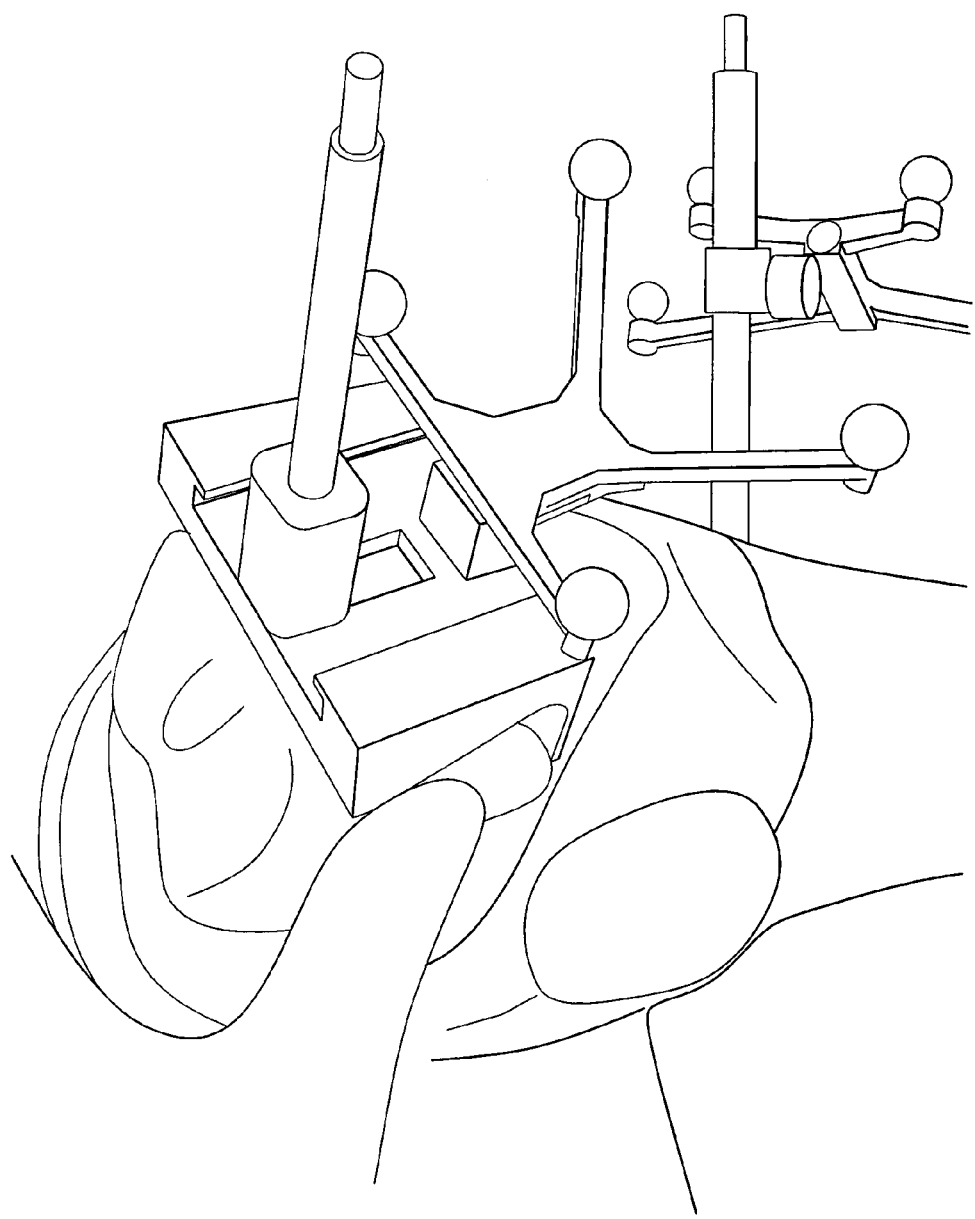
FIG. 33 is another view which shows navigation and placement of an alignment guide according to one embodiment of the present invention.

FIG. 27 shows orientation of an extramedullary rod 36 to which a fiducial 14 is attached via impactor 22. The surgeon views the screen 24 which has an image as shown in FIG. 32 of the rod 36 overlain on or in combination with the femur 12 fluoroscopic image as the two are actually positioned and oriented relative to one another in space. The surgeon then navigates the rod 36 into place preferably along the mechanical axis of the femur and drives it home with appropriate mallet or other device.

Figure 28:
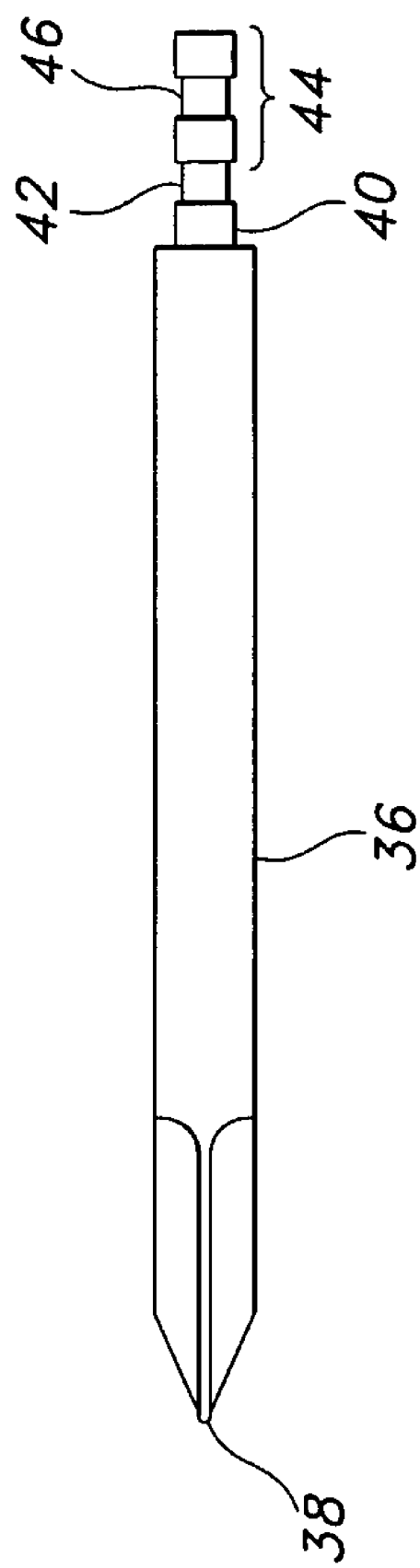
FIG. 28 is a view of an extramedullary rod according to one embodiment of the present invention.

FIG. 28 shows an extramedullary rod 36, according to one embodiment of the invention, which includes a first end that is adapted to fasten to bone and a second end that is adapted for attachment or connection to a cutting block 34 or other instrumentation. In a preferred embodiment of this invention, the first end of the extramedullary rod 36 has a pointed, splined tip 38 that is capable being being driven or otherwise introduced into and fastened to bone with a mallet, wrench or other suitable tool or device. The tip can feature threads, curved spines, or any structure that is suitable for efficient and effective introduction into and purchase of or fastening bone sufficient to support cutting block 34 or other instrumentation while being used to alter bone. Devices according to aspects of the present invention thus avoid the need to bore a hole in the metaphysis of the femur and place a reamer or other rod 36 into the medullary canal which can cause fat embolism, hemorrhaging, infection and other untoward and undesired effects.

As shown in FIG. 28, the second end of the extramedullary rod 36 may be attached to a base member 40 (permanently or in releasable fashion) and that is capable of permanent or releasable attachment to a cylindrical connector 42. The cylindrical connector 42 is capable of permanent or releasable attachment to a cylindrical knob 44 that has an integrated, circumferential groove 46. The circumferential groove 46 is adapted to secure an impactor or any other desired structure to the second end of the extramedullary rod 36. The base member 40, connector 42, and knob 44 may form a unitary structure that is capable of permanent or releasable attachment to an extramedullary rod 36. Any desired connection structure can be employed.

Figure 29:
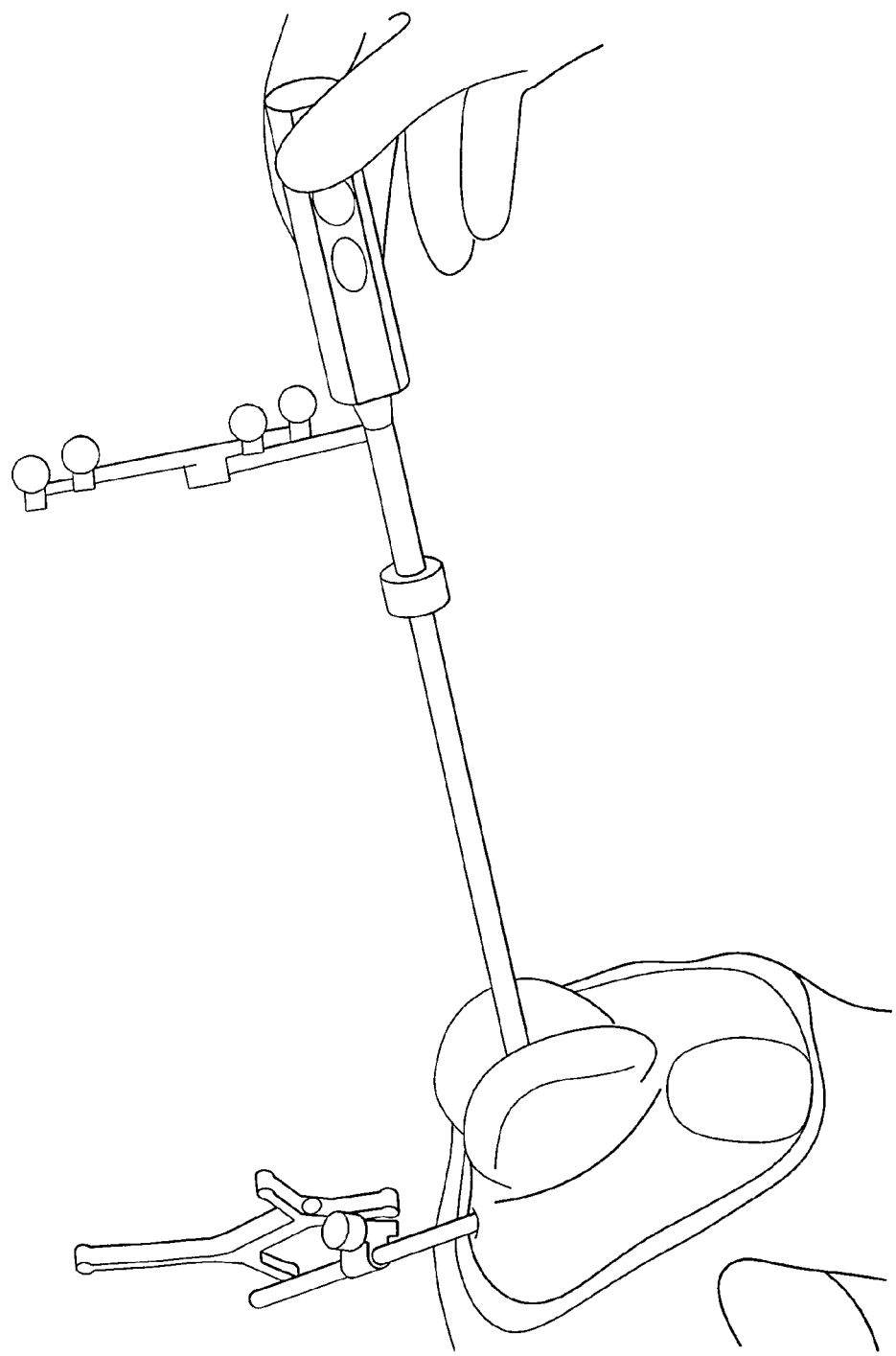
FIG. 29 is another view showing navigation and placement of an extramedullary rod according to one embodiment of the present invention.
Figure 30:
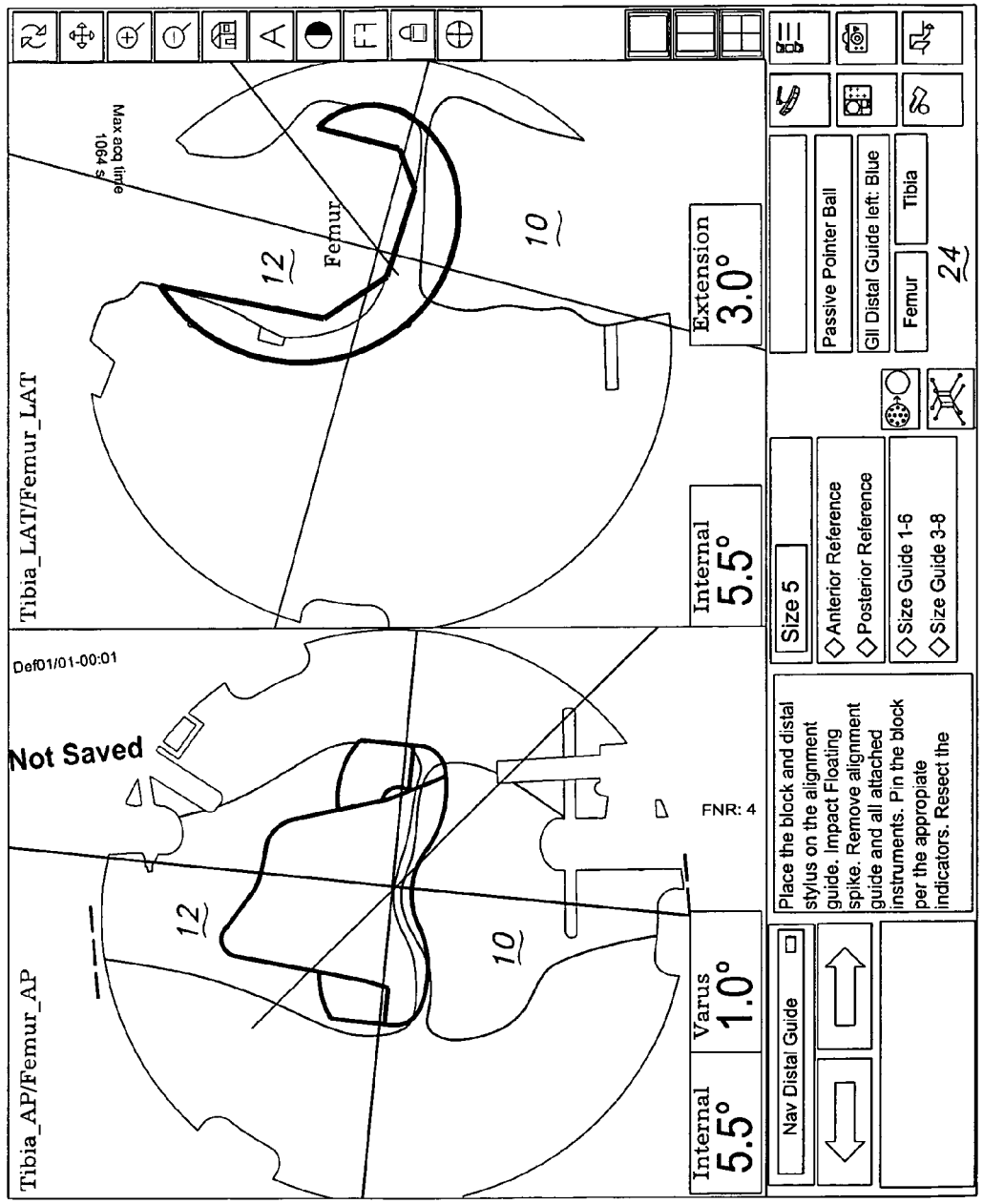
FIG. 30 is a screen face produced according to one embodiment of the present invention which assists in navigation and/or placement of an extramedullary rod.
Figure 31:
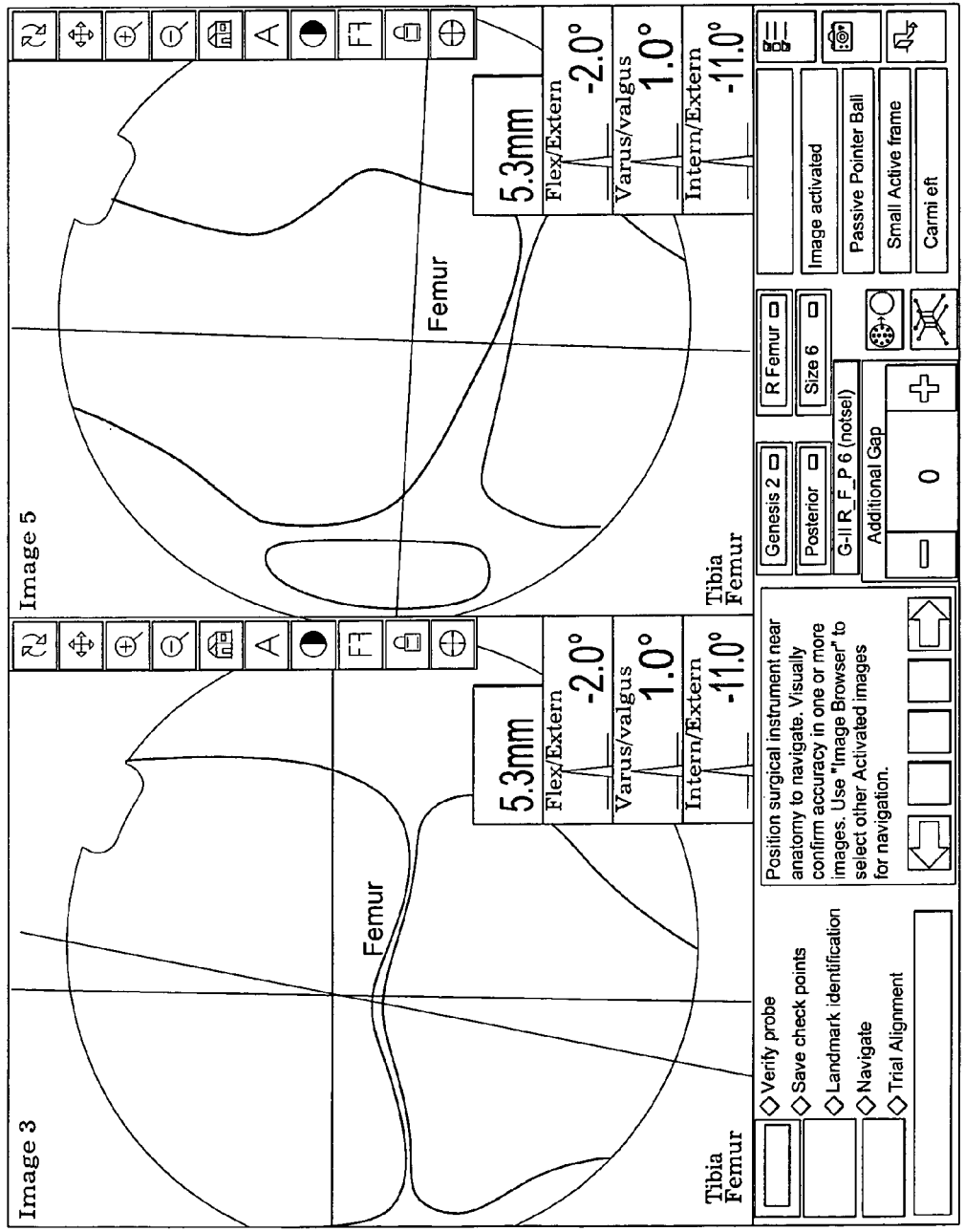
FIG. 31 is another view of a screen face produced according to one embodiment of the present invention which assists in navigation and/or placement of an extramedullary rod.

FIG. 29 also shows the extramedullary rod 36 being located through computer assisted navigation. FIG. 30 shows fluoroscopic images, both anterior-posterior and lateral, with axes, and with a computer generated and tracked image of the rod 36 superposed or in combination with the fluoroscopic images of the femur and tibia. FIG. 31 shows the rod 36 superposed on the femoral fluoroscopic image similar to what is shown in FIG. 30.

FIG. 30 also shows other information relevant to the surgeon such as the name of the component being overlain on the femur image (new EM nail), suggestions or instructions at the lower left, and angle of the rod 36 in varus/valgus and extension relative to the axes. Any or all of this information can be used to navigate and position the rod 36 relative to the femur. At a point in time during or after placement of the rod 36, its tracking may be "handed off" from the impactor fiducial 14 to the femur fiducal 14 as discussed below.

Once the extramedullary rod 36, intramedullary rod, other type of rod or any other type of structural member has been placed, instrumentation can be positioned as tracked in position and orientation by sensor 16 and displayed on screen face 24. Thus, a cutting block 34 of the sort used to establish the condylar anterior cut, with its fiducial 14 attached, is introduced into the field and positioned on the rod 36. Because the cutting block 34 corresponds to a particular implant product and can be adjusted and designated on screen to correspond to a particular implant size of that product, the computer 18 can generate and display a graphic of the cutting block 34 and the femoral component overlain on the fluoroscopic image as shown in FIGS. 34–37. The surgeon can thus navigate and position the cutting block 34 on screen using not only images of the cutting block 34 on the bone, but also images of the corresponding femoral component which will be ultimately installed. The surgeon can thus adjust the positioning of the physical cutting block 34 component, and secure it to the rod 36 in order to resect the anterior of the condylar portion of the femur in order to optimally fit and position the ultimate femoral component being shown on the screen. FIG. 35 is another view of the cutting block 34 of FIG. 32 being positioned.

Figure 41:
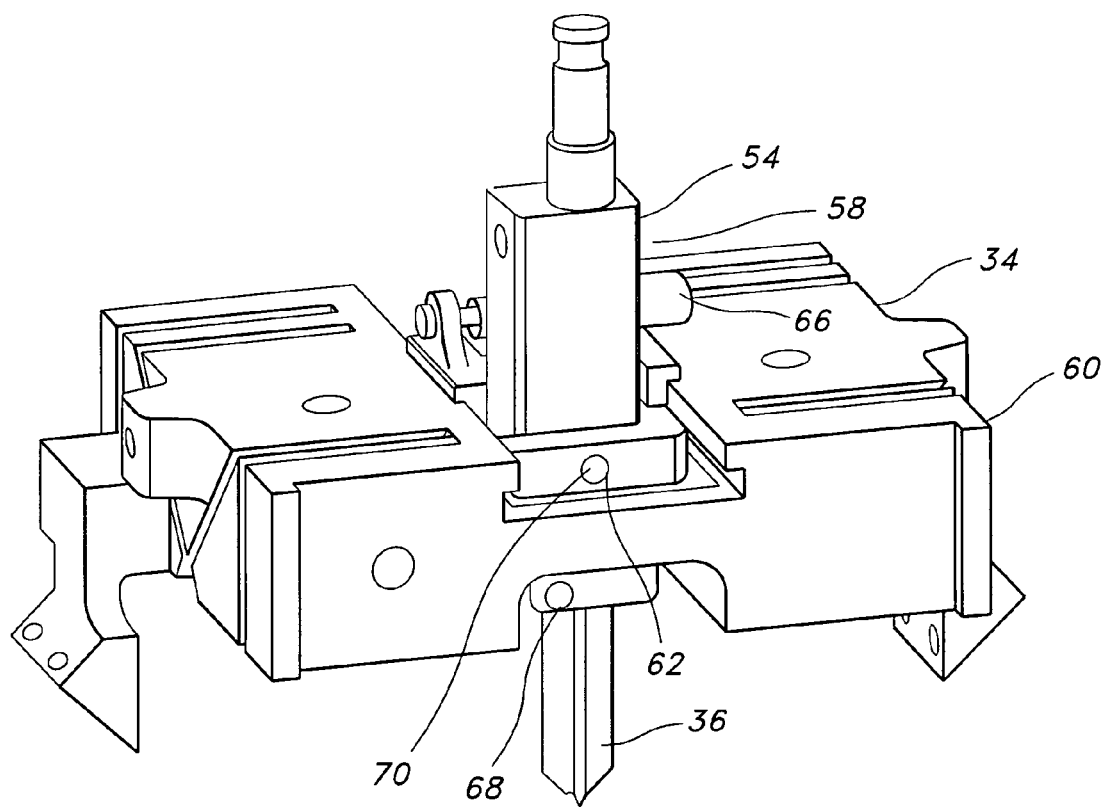
FIG. 41 shows additional aspects of the module shown in FIGS. 38A–C.
Figure 42B:
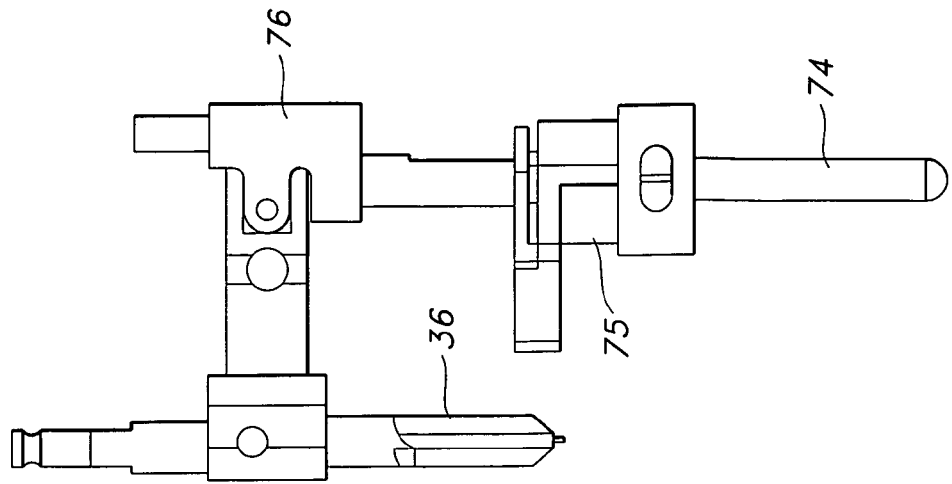
FIGS. 42A and 42B are an exploded perspective view showing certain aspects of a tibial gimbal alignment module according to one embodiment of the present invention.
Figure 42A:
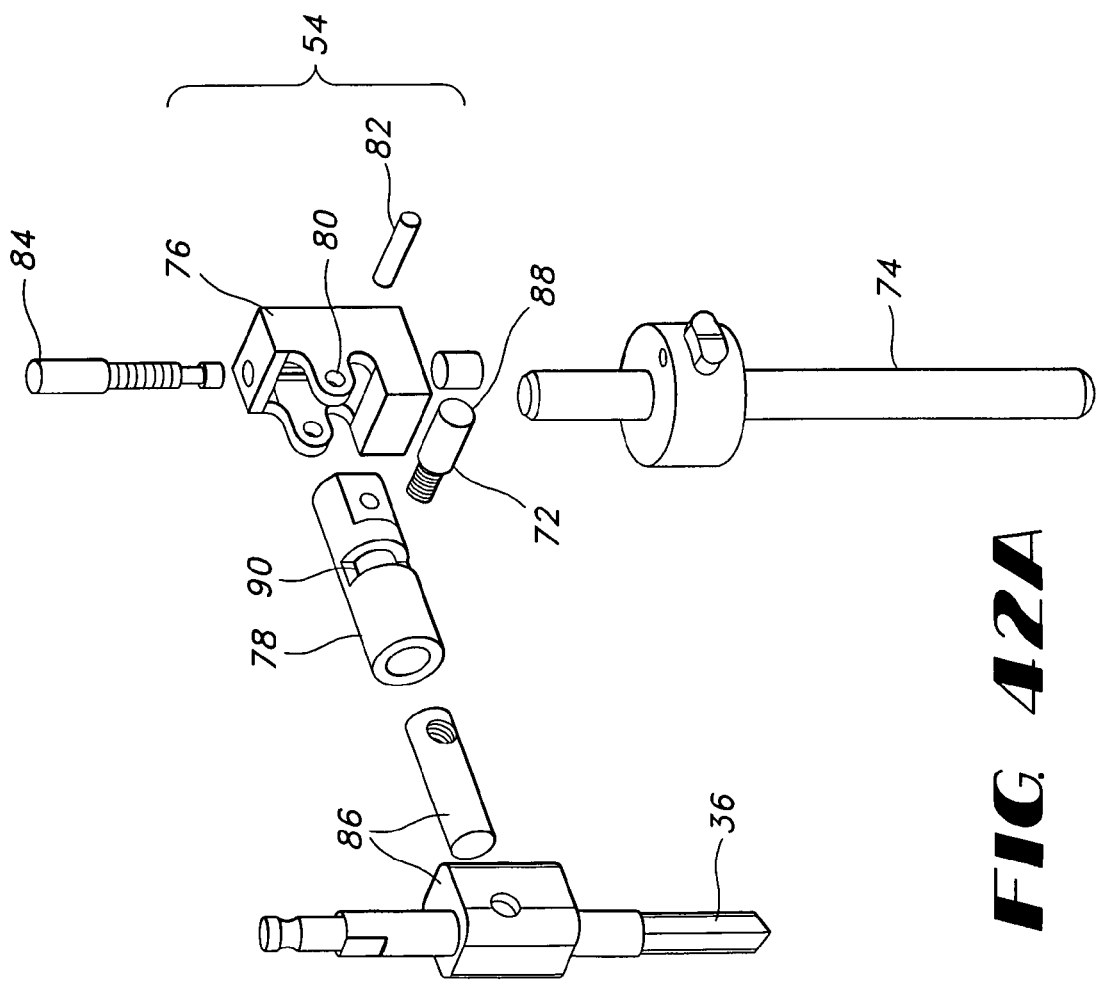
Figure 44:
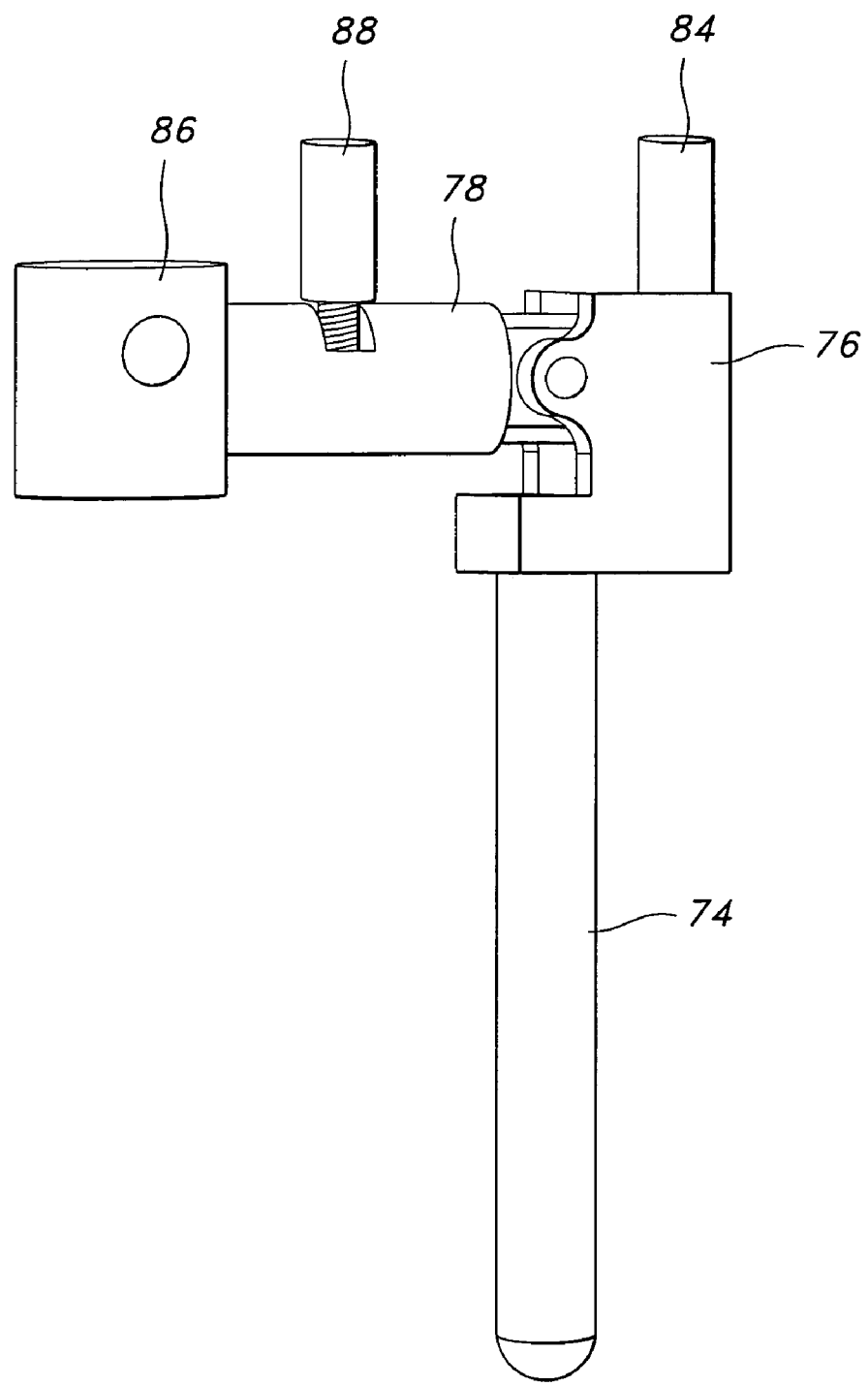
FIG. 44 shows additional aspects of the module shown in FIGS. 42A and 42B.
Figure 45:
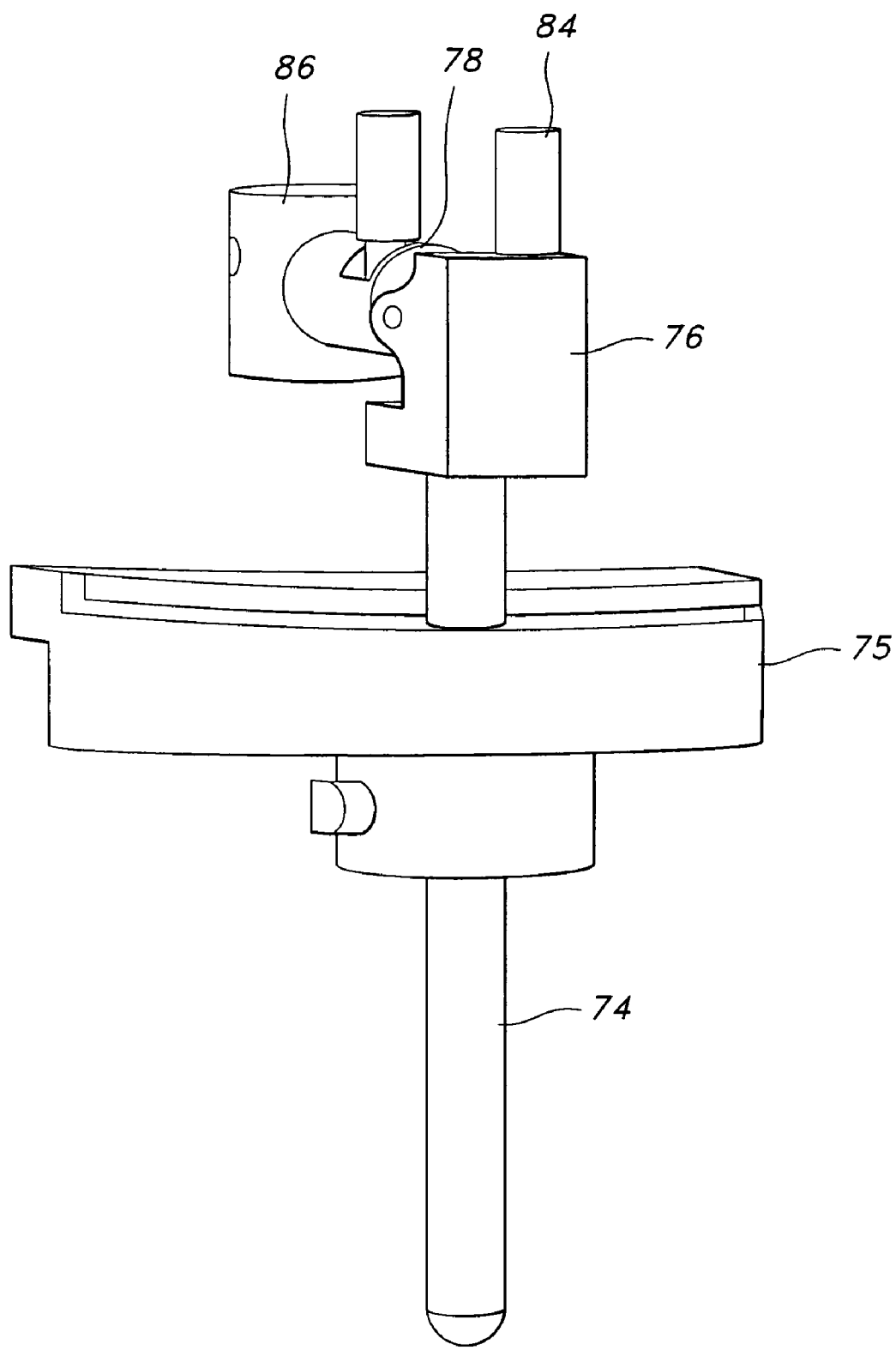
FIG. 45 shows additional aspects of the module shown in FIGS. 42A and 42B.

Cutting blocks 34 and other instrumentation may be positioned relative to femoral, tibial or other bone using instruments and devices such as variable alignment or orientation modules, versions of which according to particular aspects of the invention are shown in FIGS. 38–47. FIGS. 38–41 show a first version of a variable alignment module 54. It includes a post 58 which may be connected to an extramedullary rod 36 as shown in FIG. 28, an intramedullary rod or as otherwise desired. Post 58 connects to a cutting block or other instrument 34 via two gimbal members, first or outer gimbal 60 and a second or inner gimbal 62. First or outer gimbal 60, which may be mechanically connected to cutting block 34 as shown in FIGS. 40 and 41, is connected in pivoting fashion to second gimbal 62 using, for example, openings 64 and pins 70. First gimbal 60 receives a worm gear 66 which cooperates with a first follower (located on the second gimbal 62) whose teeth follow action of the worm gear 66 in order to vary the angle of the first and second gimbals 60, 62 relative to each other. In the embodiment shown in FIGS. 38–41, worm gear 66 in this fashion adjusts varus/valgus angulation of cutting block or instrument 34 relative to bone.

Figure 39B:
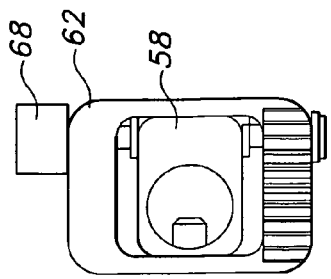
FIGS. 39A–C are views showing other aspects of the module shown in FIGS. 38A–C.
Figure 39C:
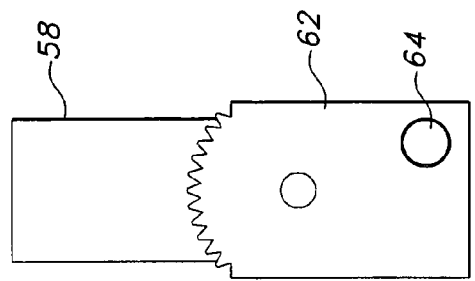
Figure 39A:
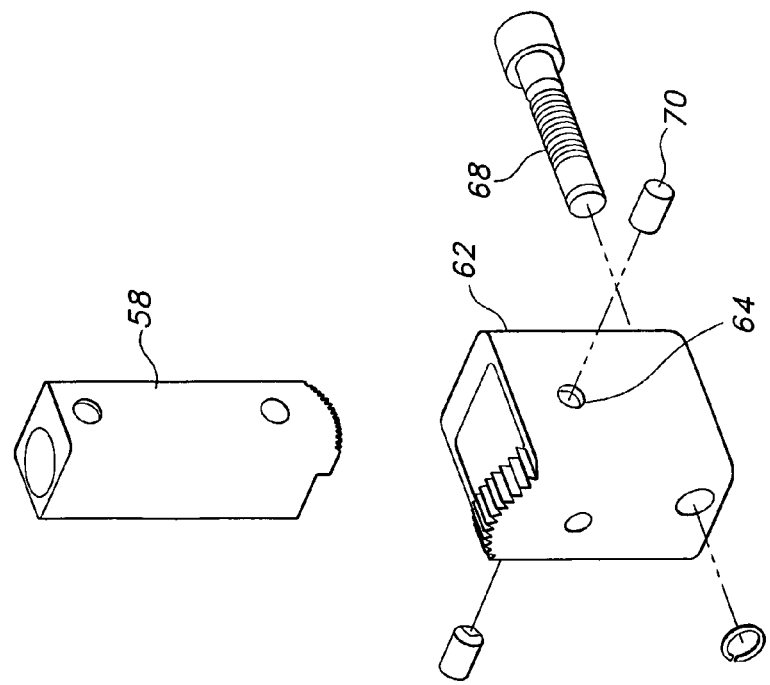

FIG. 39 shows more clearly the post 58 (which can receive and be secured to extramedullary rod 36 or other devices using, for example, a bore and pin 70) and second gimbal 62 connected in pivoting relationship in a fashion conceptually similar to the manner in which first and second gimbals 60 and 62 are connected. As shown in FIG. 39, post 58 penetrates gimbal 62 in pivoting fashion using openings 64 and pins 70. Second gimbal 62 receives a worm gear 68 which cooperates with a second follower on post 58 to vary the angle of post 58 relative to second gimbal 62.

As shown in FIGS. 40 and 41, the angulation of cutting block 34 relative to rod 36 may be varied in varus and valgus using worm gear 66 and flexion/extension using worm gear 68.

FIGS. 42–45 show a variable alignment module which may used for instrumentation employed in connection with the tibia. The operation and structure are conceptually similar to the femoral module shown in FIGS. 38–41. Here, a first gimbal 76 may be rigidly or otherwise mounted to a member 74 which in turn receives instrumentation such as a cutting block 75. First gimbal 76 connects to second gimbal 78 using pin 82 extending through holes 80 in first gimbal 76 to capture second gimbal 78 so that it may pivot relative to first gimbal 76. A worm gear 84 connects to first gimbal 76 and drives a follower on second gimbal 78 to adjust angulation of second gimbal 78 relative to first gimbal 76. Worm gear 84 can thus adjust flexion/extension orientation of the cutting block 75 relative to the tibia.

A post 86 which receives extramedullary rod 36 or other rod or bone-connecting structure, and which may be formed of a cylindrical member in combination with other structure for retaining rod 36 in desired relationship, is received relative to second gimbal 78 in adjustable fashion. In the embodiment shown in FIGS. 42–45, an adjustment screw 88 cooperates with a slot in the second gimbal 78 in order to allow the post 86 to rotate within gimbal 78 and be secured at desired angulation. Adjustment screw 88 and slot 90 are but one variation of any adjustment mechanism, such as worm and follower, rack and pinion, vernier, or other angulation control devices or structures which could be used in this embodiment, the embodiment shown in FIGS. 38–41 other embodiments. Accordingly, this structure may be used to adjust varus/valgus alignment of cutting block 75.

With respect to the femoral structure shown in FIGS. 38–41 and the tibial structure shown in FIGS. 42–45, other structures which allow adjustment of angulation or orientation not only of the two axis, but any desired angulation of cutting block 75 relative to rod 36 (and thus bone) can be used. Gimbals can be reversed in structure and function, different calibration and adjustment mechanisms can be used including with indicia in order to introduce repeatability, and other structures may be employed as well. Fiducials 14 can be attached to any desired portion of these structures, directly or indirectly, for tracking in accordance with aspects of the invention.

Figure 46B:
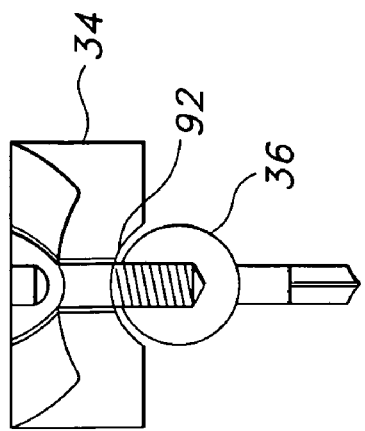
FIGS. 46A and 46B show another structure for alignment modules according to alternative embodiments of the present invention.
Figure 46A:
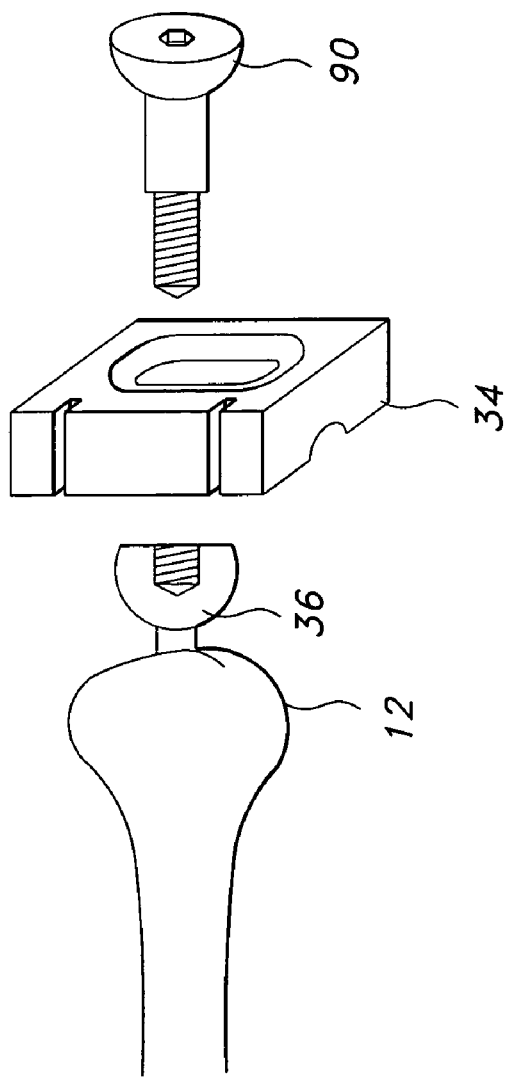
Figure 47:
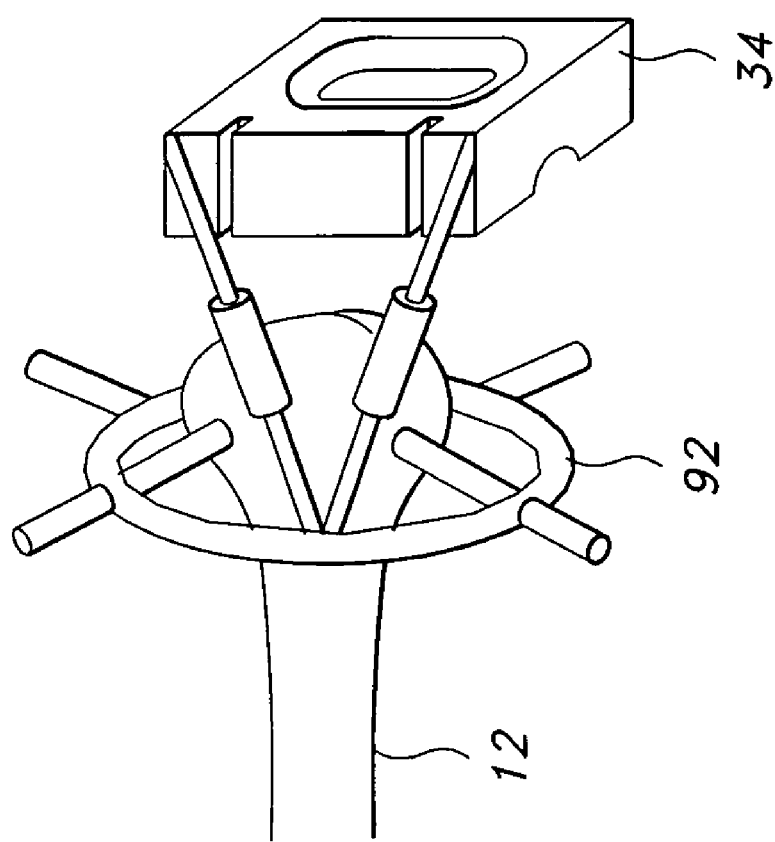
FIG. 47 shows another structure for alignment modules according to alternative embodiments of the present invention.
Figure 48:
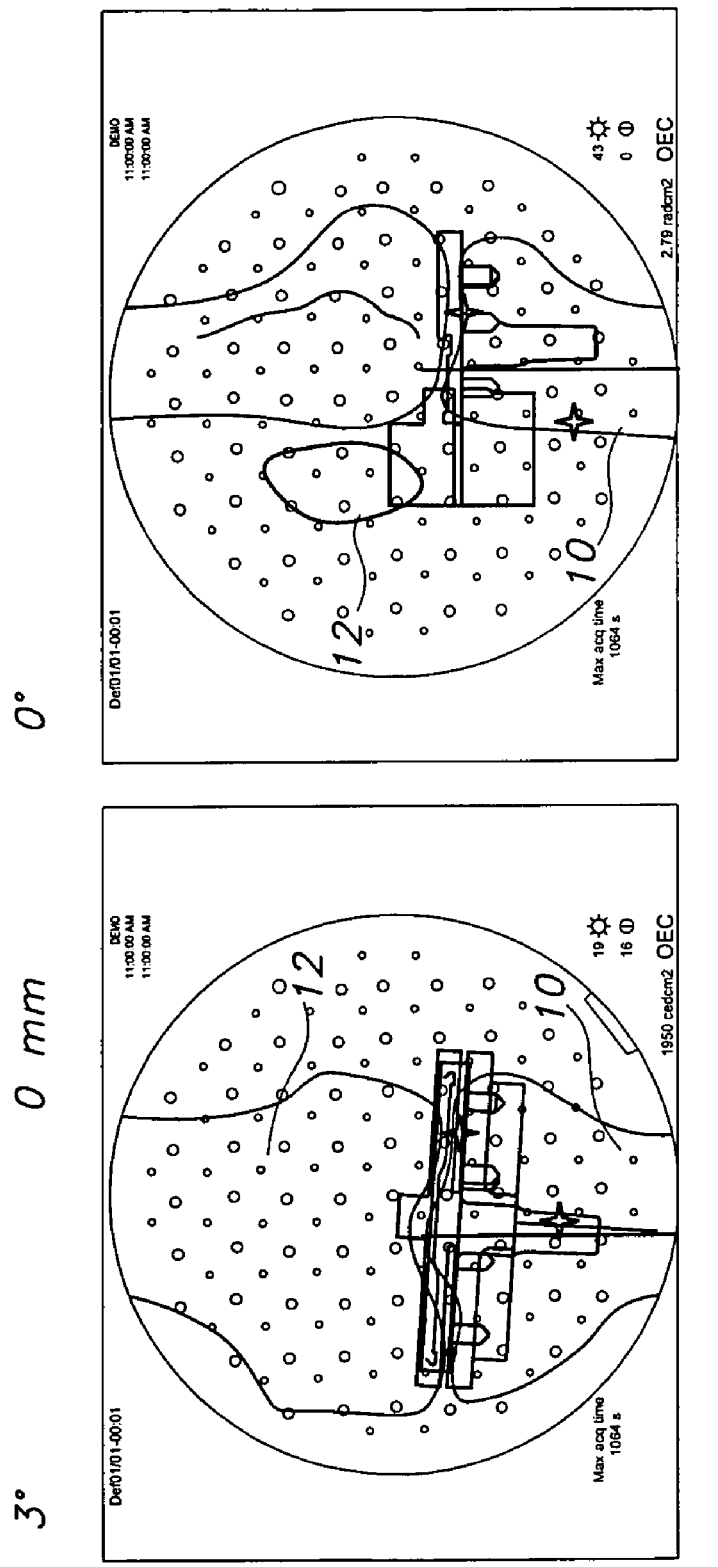
FIG. 48 is a screen face which shows a fluoroscopic image of bone in combination with computer generated images of axes and components in accordance with one embodiment of the present invention.
Figure 49:
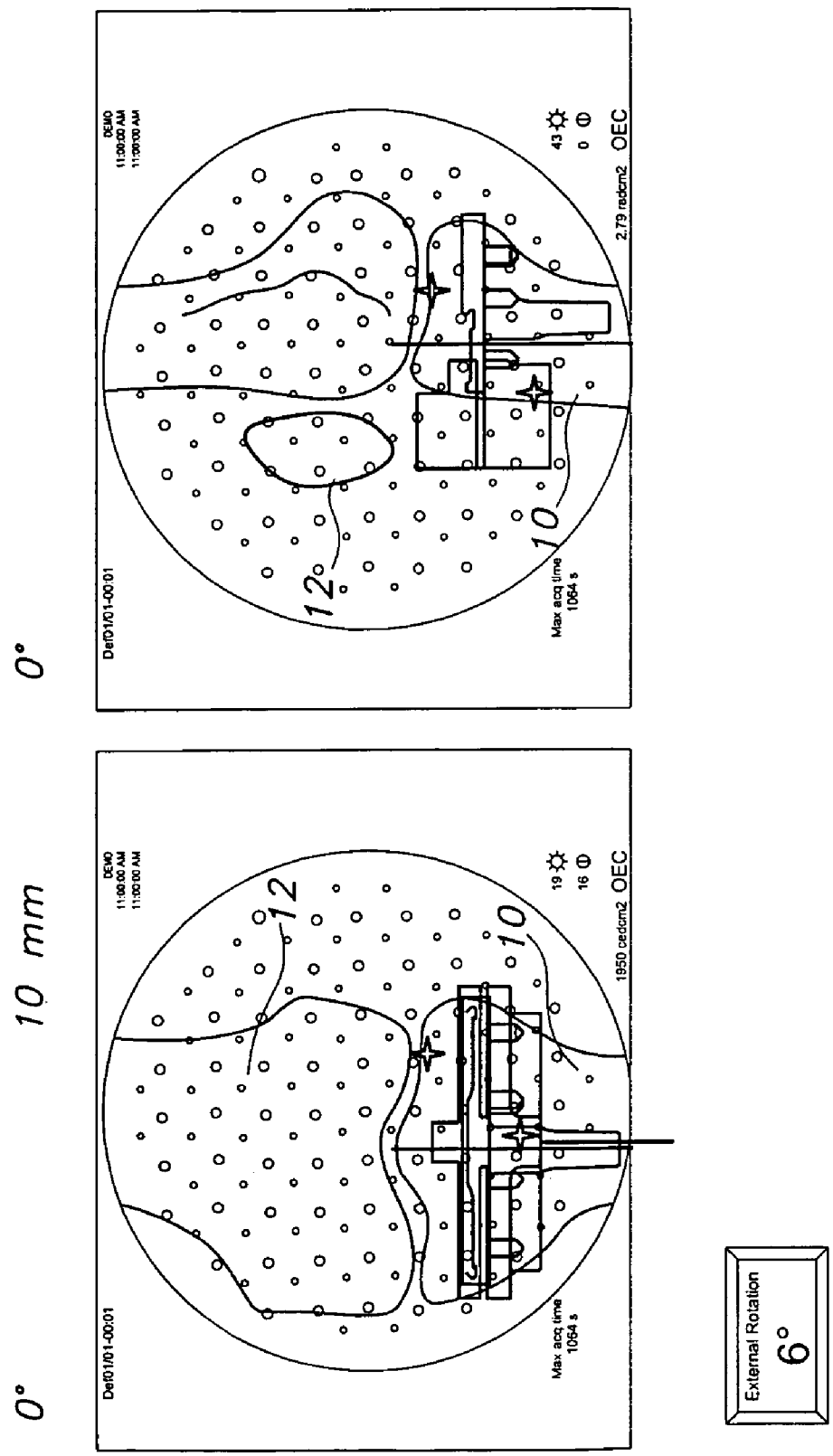
FIG. 49 is a screen face which shows a fluoroscopic image of bone in combination with computer generated images of axes and components in accordance with one embodiment of the present invention.
Figure 51:
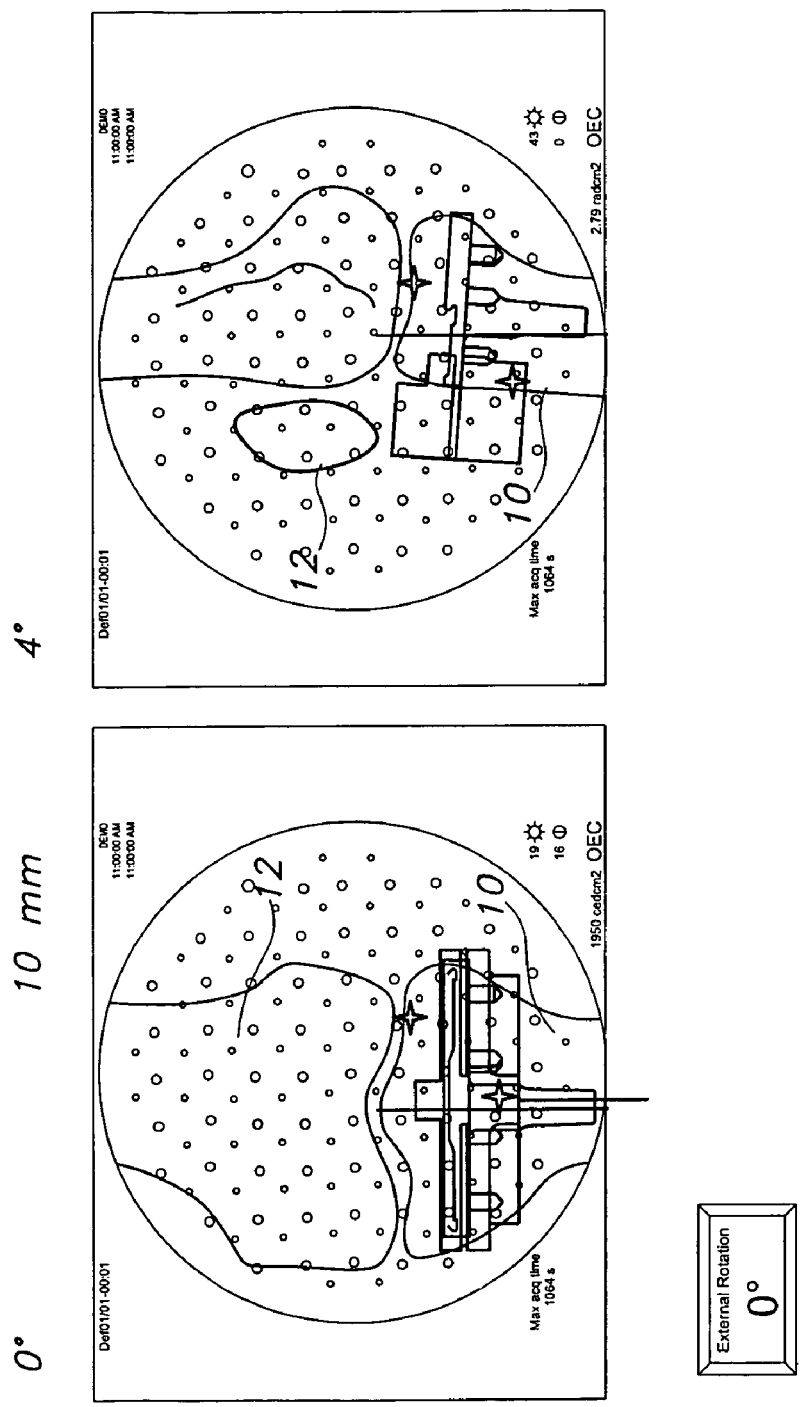
FIG. 51 is a screen face which shows a fluoroscopic image of bone in combination with computer generated images of axes and components in accordance with one embodiment of the present invention.

FIGS. 46 and 47 show two structures among many which can be used to adjust positioning of cutting block 34 or other instrumentation relative to rod 36. In the version shown in FIG. 46, rod 36 which may be extramedullary, intramedullary, or otherwise, features a spherical or otherwise curved three-dimensional head with a generally concentric threaded bore. An adjustment bolt 90 features threads which cooperate with the threads in head 36. The bolt 90 penetrates cutting block 34 in desired fashion so that the cutting block 34, which features a recess 92 on its bottom surface that corresponds to the shape of the head of 36, however closely, can be angulated as desired in any dimension and then set via tightening of bolt 90 at any desired angulation in multiple planes.

FIG. 47 shows a variation in which the cutting block 34 may be connected to external fixation systems 92, such as those described U.S. Pat. No. 5,728,095, which is incorporated herein by this reference, in order to adjustably position the cutting block 34 relative to femoral or tibial bone. As described in that patent and others on the subject, calibrations may be employed on the struts connecting the cutting block 34 and the fixator element 92 in order for repeatability and controllability of angulation of cutting block 34 relative to fixation element or device 92.

Figure 52:
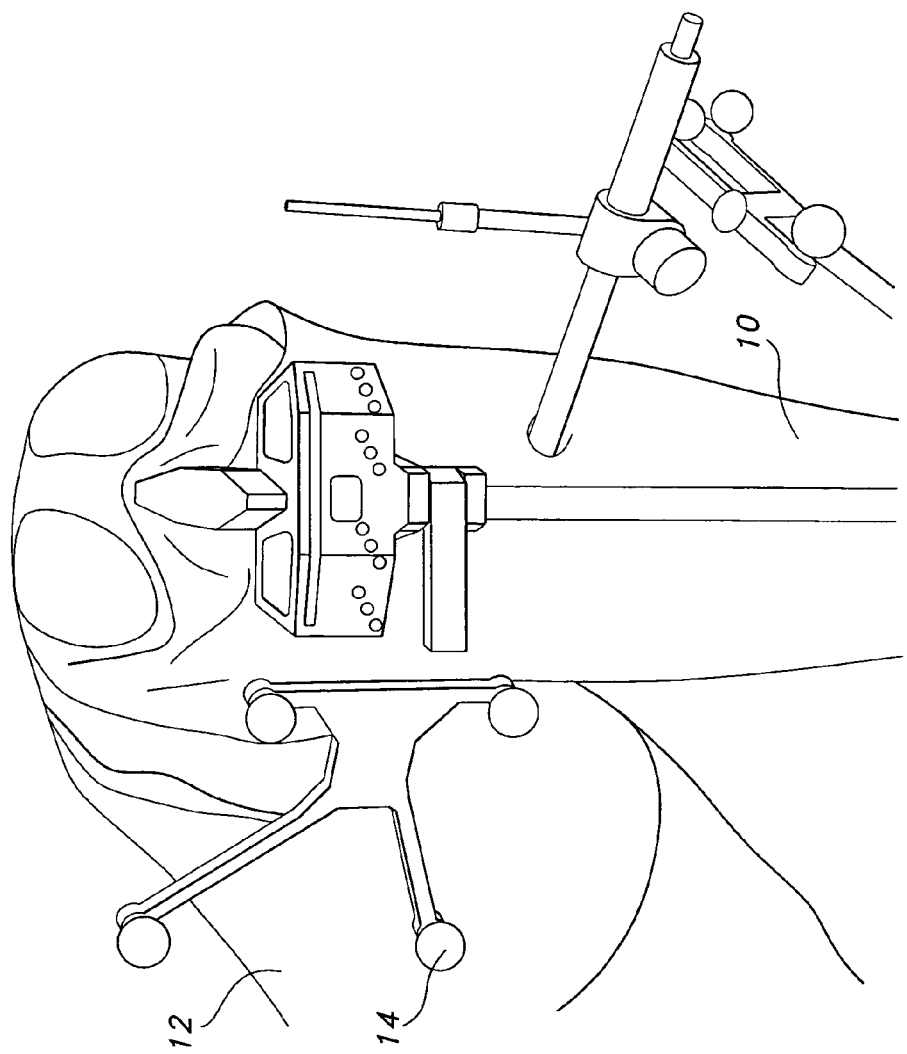
FIG. 52 is a view showing placement of a cutting block according to one embodiment of the present invention.

FIGS. 48–52 show instrumentation that has been navigated and positioned on the proximal portion of the tibia 10 as shown in FIG. 52 and as tracked by sensor 16 and on screen by images of the cutting block and the implant component as shown in FIGS. 48–51.

Figure 53:
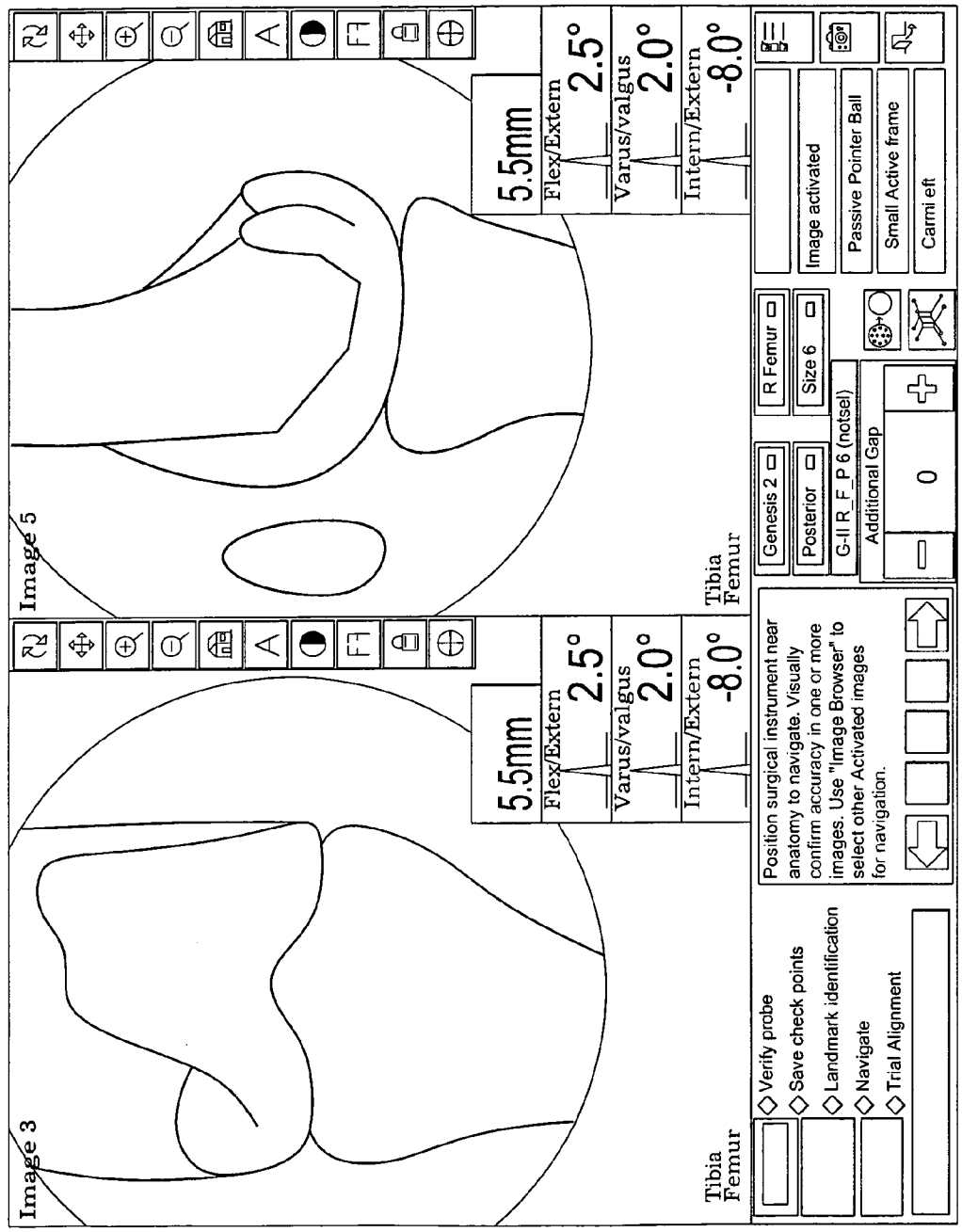
FIG. 53 is a screen face according to one embodiment of the present invention which may be used to assist in navigation and placement of instrumentation.
Figure 54:
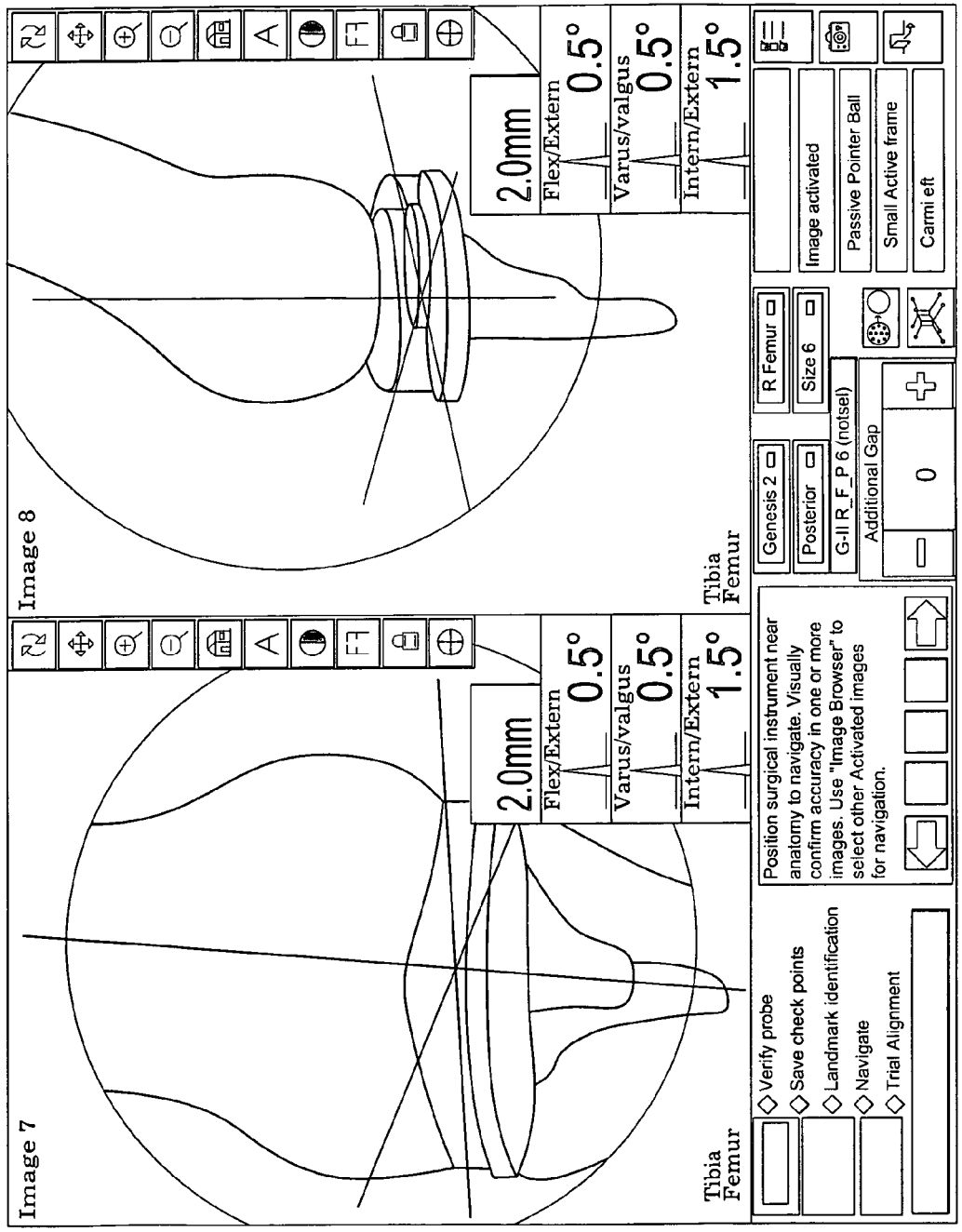
FIG. 54 is another screen face according to one embodiment of the present invention which may be used to assist in navigation and/or placement of instrumentation.
Figure 55:
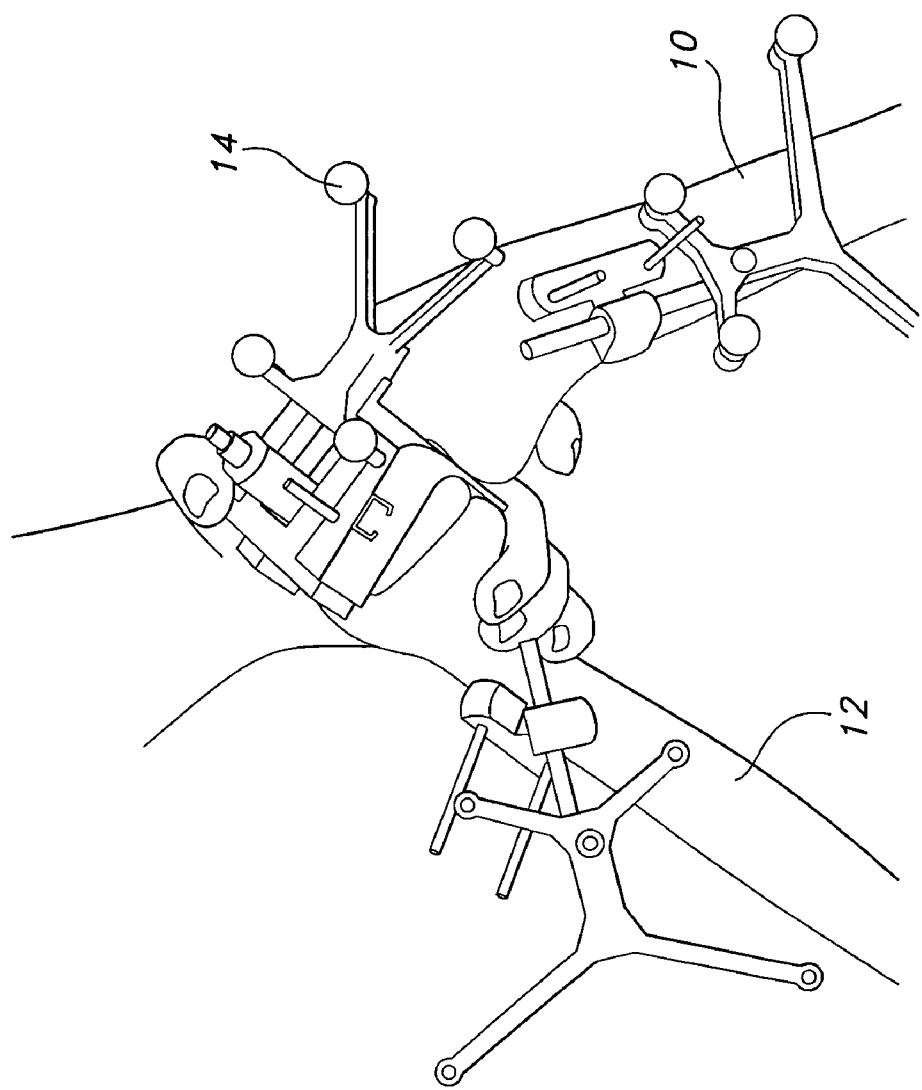
FIG. 55 is a view showing placement of an alignment guide according to one embodiment of the present invention.
Figure 56:
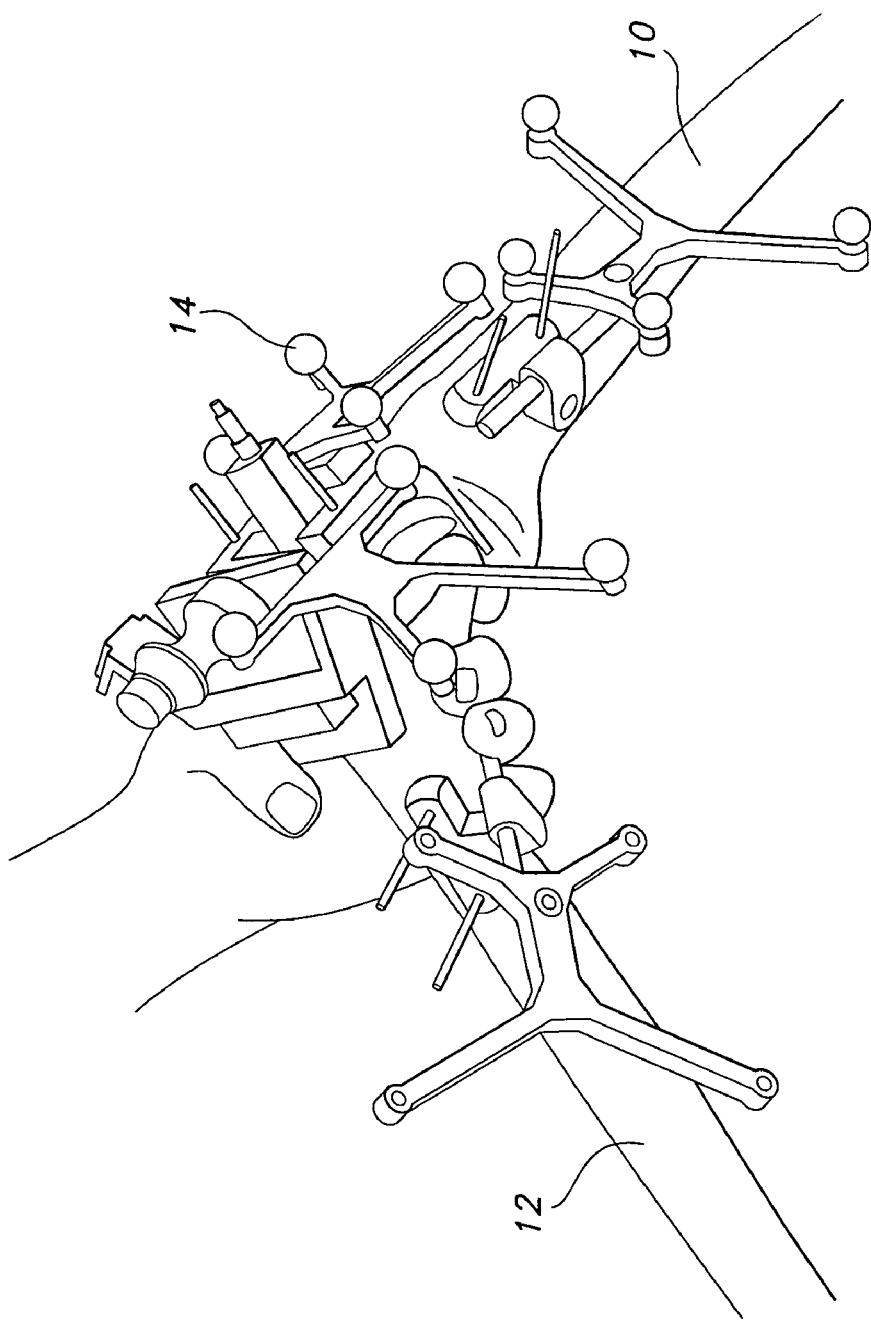
FIG. 56 is another view showing placement of a cutting block according to one embodiment of the present invention.
Figure 57:
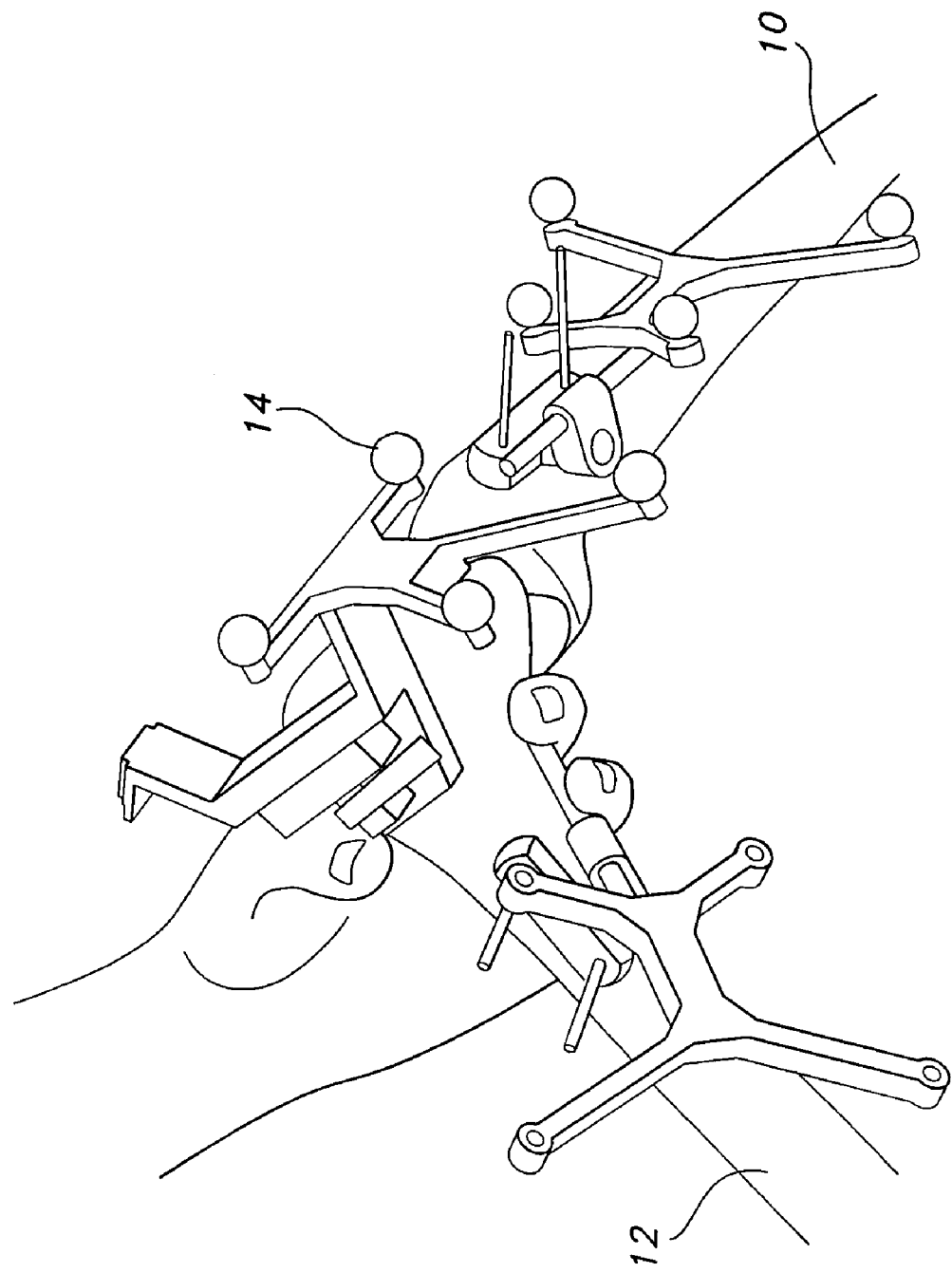
FIG. 57 is a view showing navigation and placement of the cutting block of FIG. 45.
Figure 53:
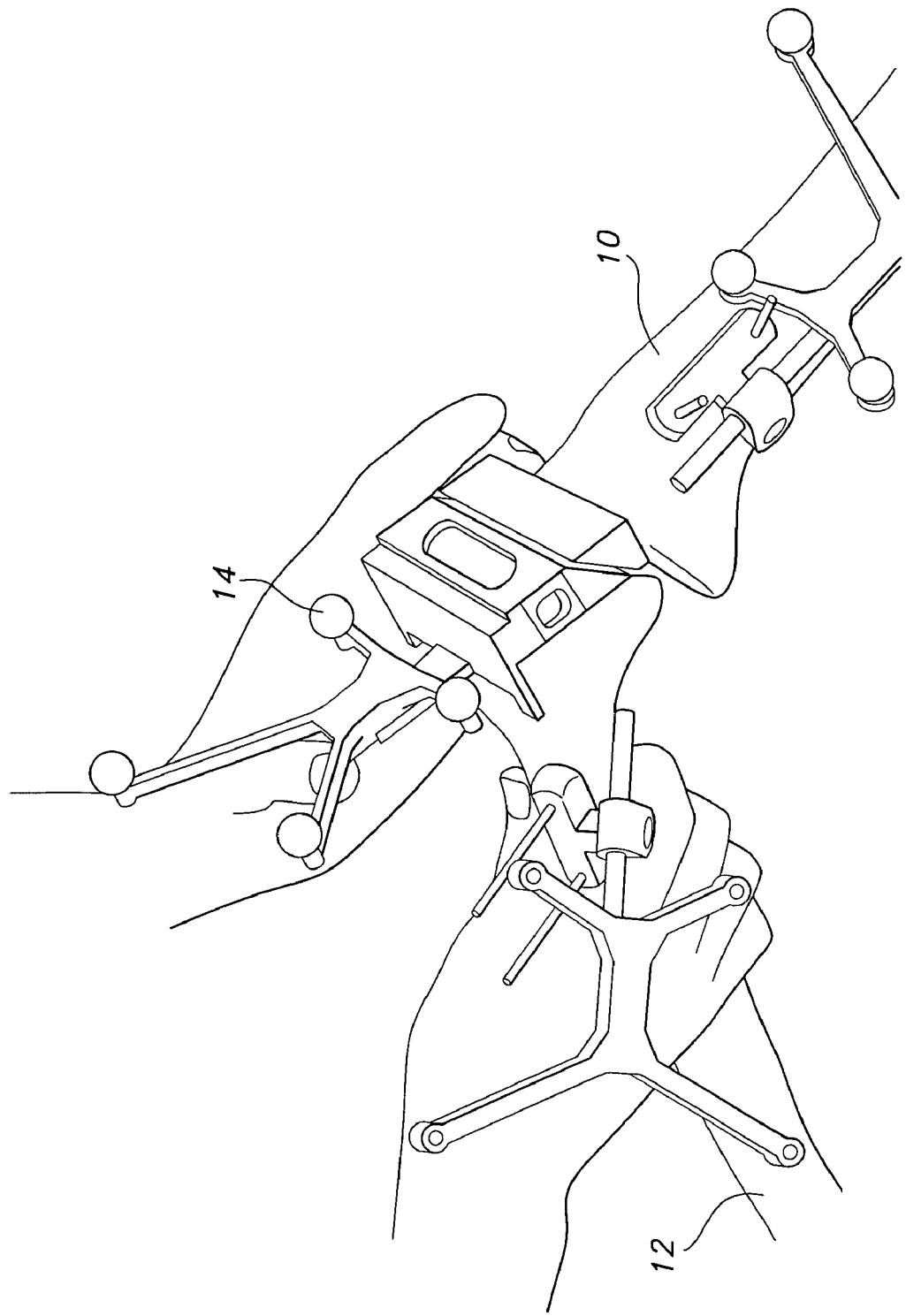
Figure 59:
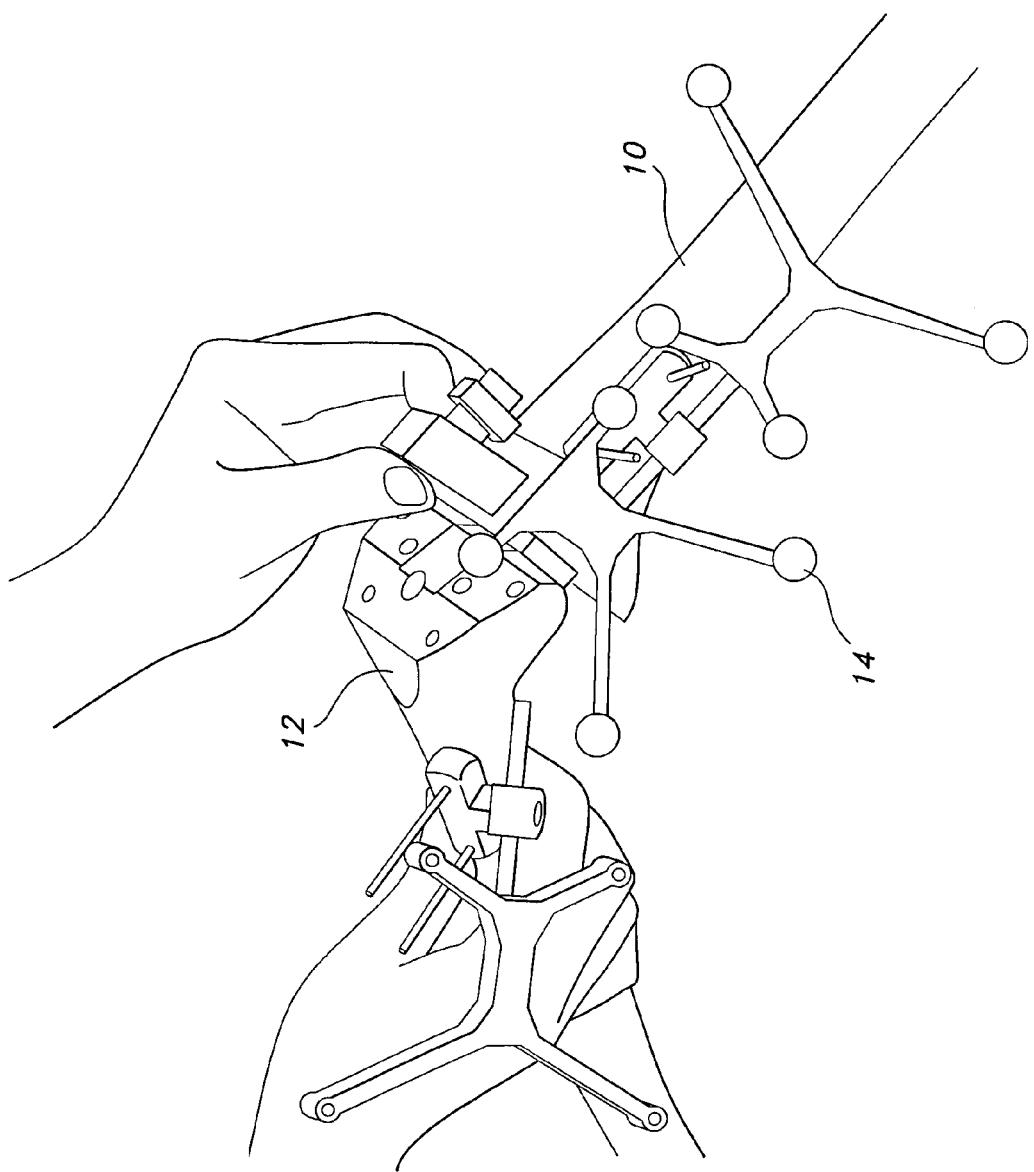
FIG. 59 is a view showing navigation and placement of a tibial cutting block according to one embodiment of the present invention.

FIGS. 53 and 54 show other onscreen images generated during this bone modification process for purposes of navigation and positioning cutting blocks 34 and other instrumentation for proper resection and other modification of femur and tibia in order to prepare for trial components and implant components according to instrumentation, systems, and processes of the embodiment of the present invention shown in FIGS. 4–75.

FIGS. 55–59 also show instrumentation being positioned relative to femur 12 as tracked by the system for resection of the condylar component in order to receive a particular size of implant component. Various cutting blocks 34 and their attached fiducials can be seen in these views.

Figure 60:
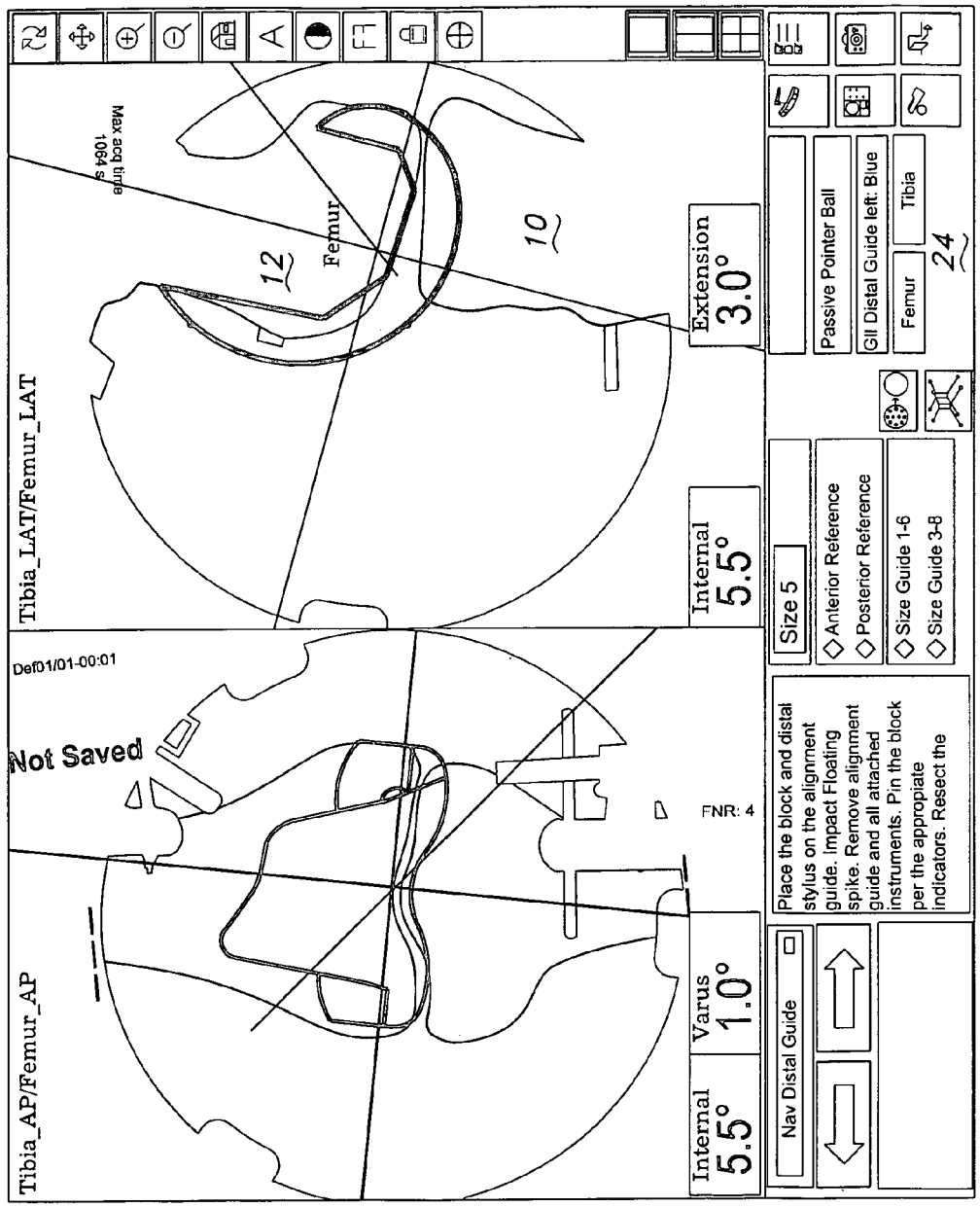
FIG. 60 is a screen face according to one embodiment of the present invention which may be used to assist in navigation and placement of instrumentation.
Figure 61:
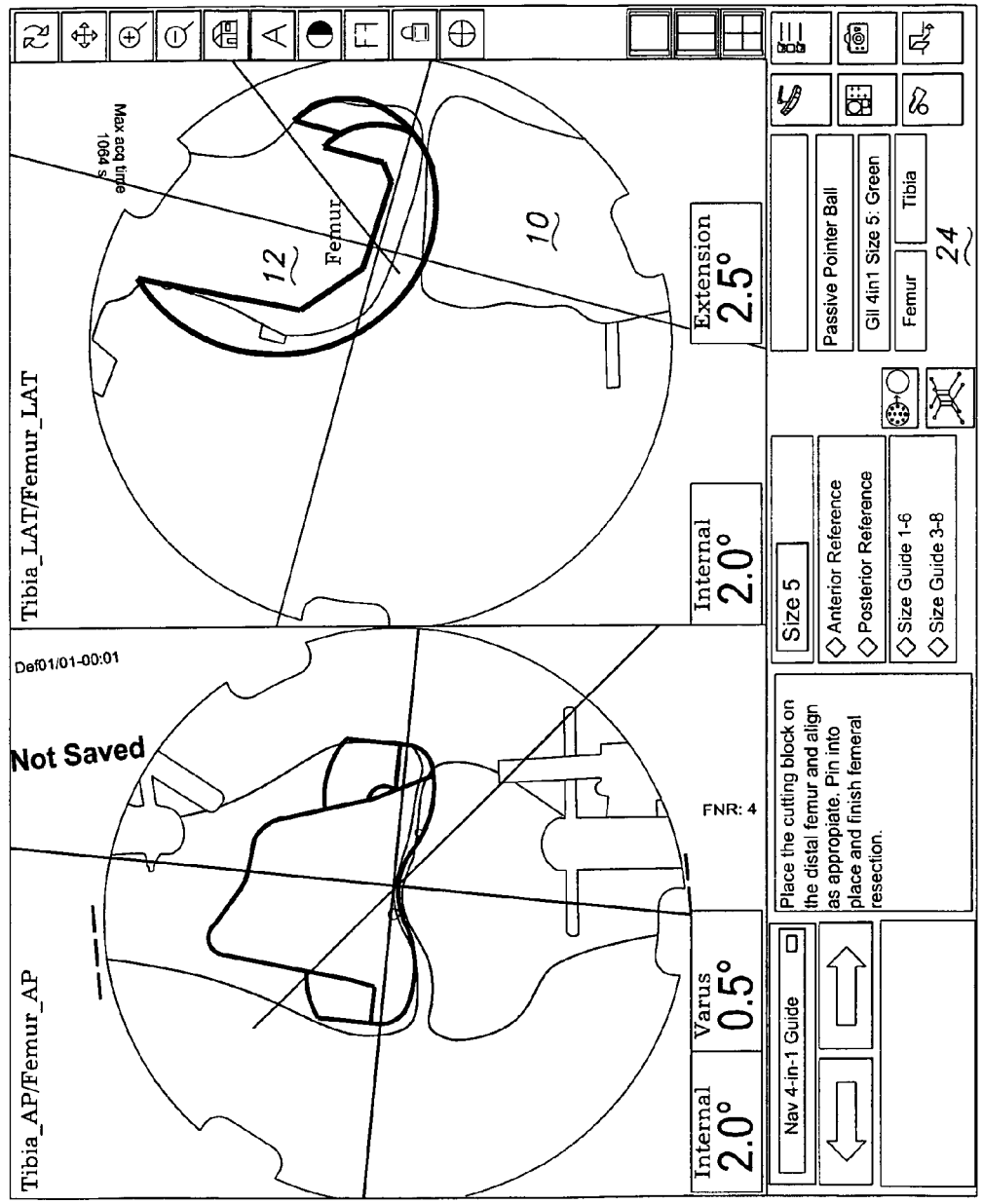
FIG. 61 is another screen face according to one embodiment of the present invention which may be used to assist in navigation and placement of instrumentation.

FIG. 60 shows a femoral component overlaid on the femur as instrumentation is being tracked and positioned in order for resection of bone properly and accurately to be accomplished. FIG. 61 is another navigational screen face showing a femoral component overlay as instrumentation is being positioned for resection of bone.

Figure 62:
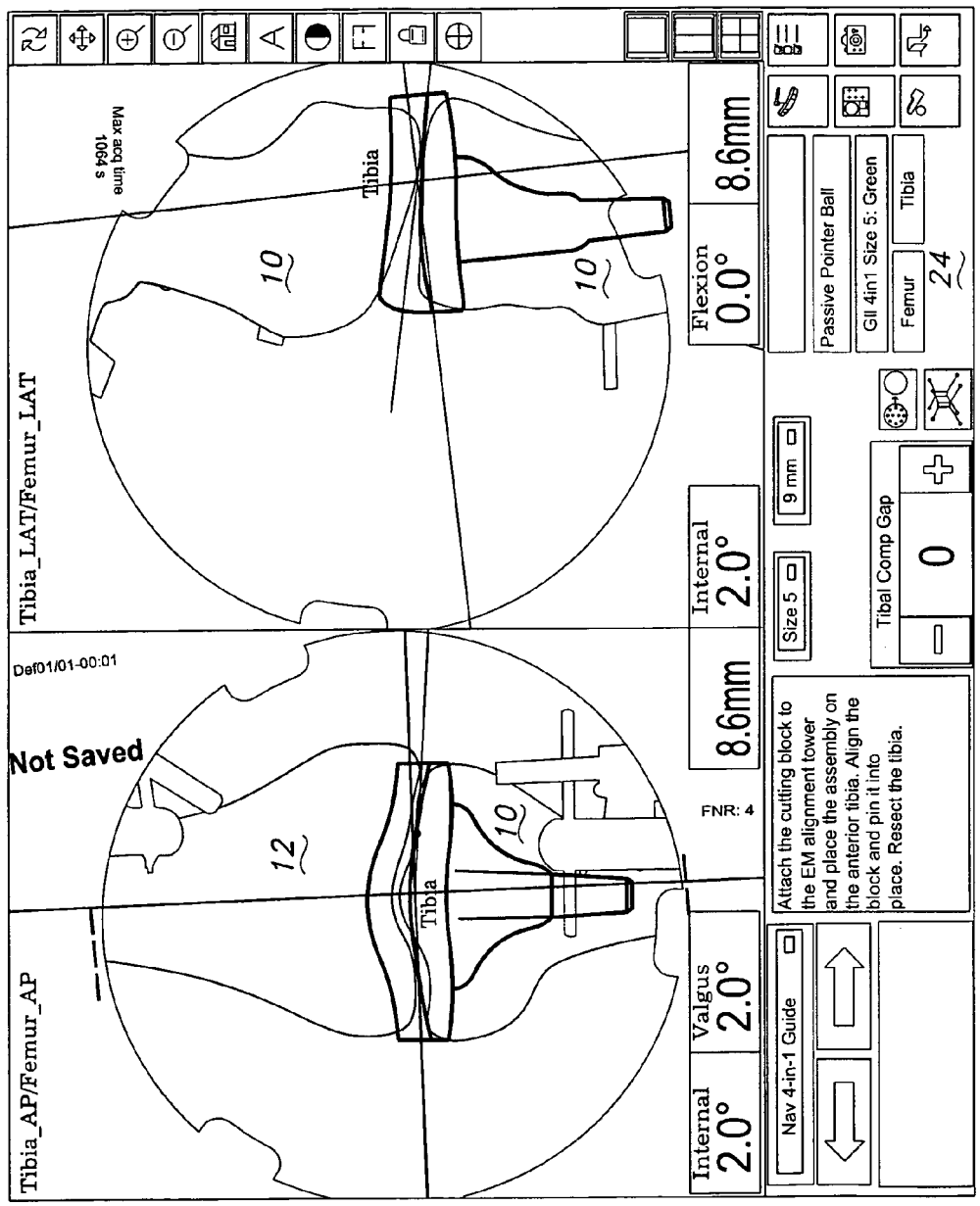
FIG. 62 is another screen face according to one embodiment of the present invention which may be used to assist in navigation and placement of instrumentation.

FIG. 62 is tibial component overlay information on a navigation screen as the cutting block 34 for the tibial plateau is being positioned for bone resection.

Figure 63:
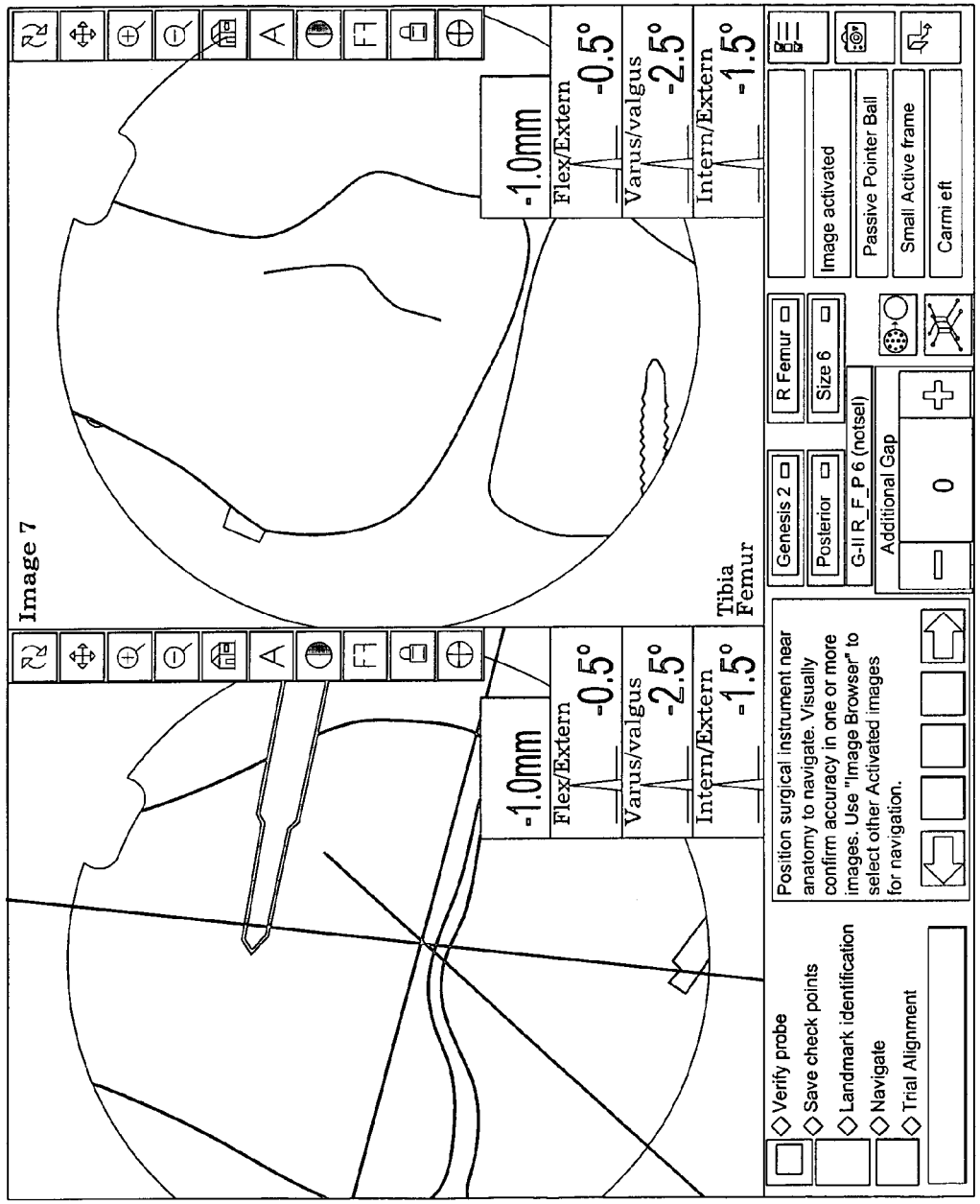
FIG. 63 is another screen face according to one embodiment of the present invention which may be used to assist in navigation and placement of instrumentation.
Figure 64:
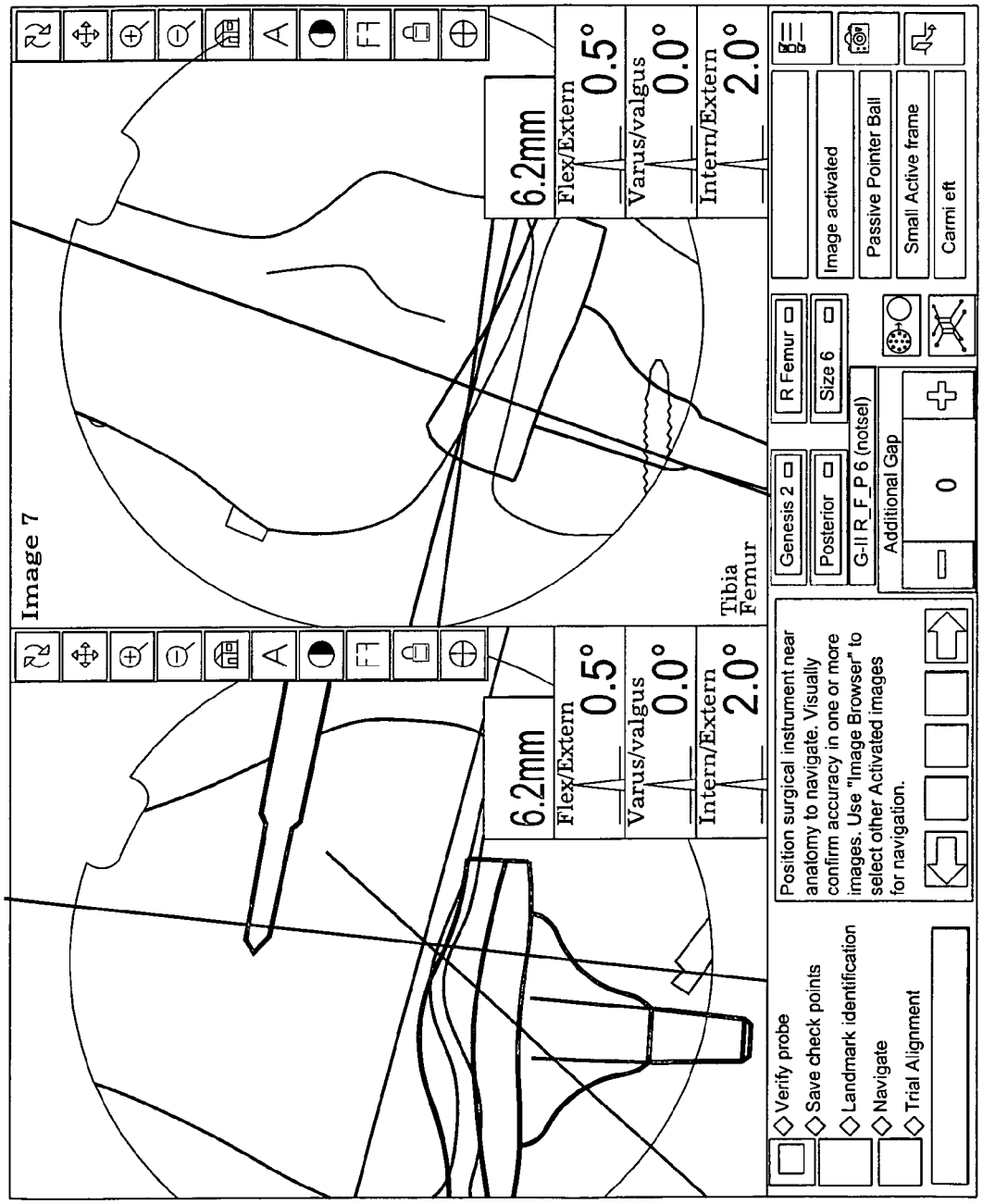
FIG. 64 is another screen face according to one embodiment of the present invention which may be used to assist in navigation and placement of instrumentation.
Figure 65:
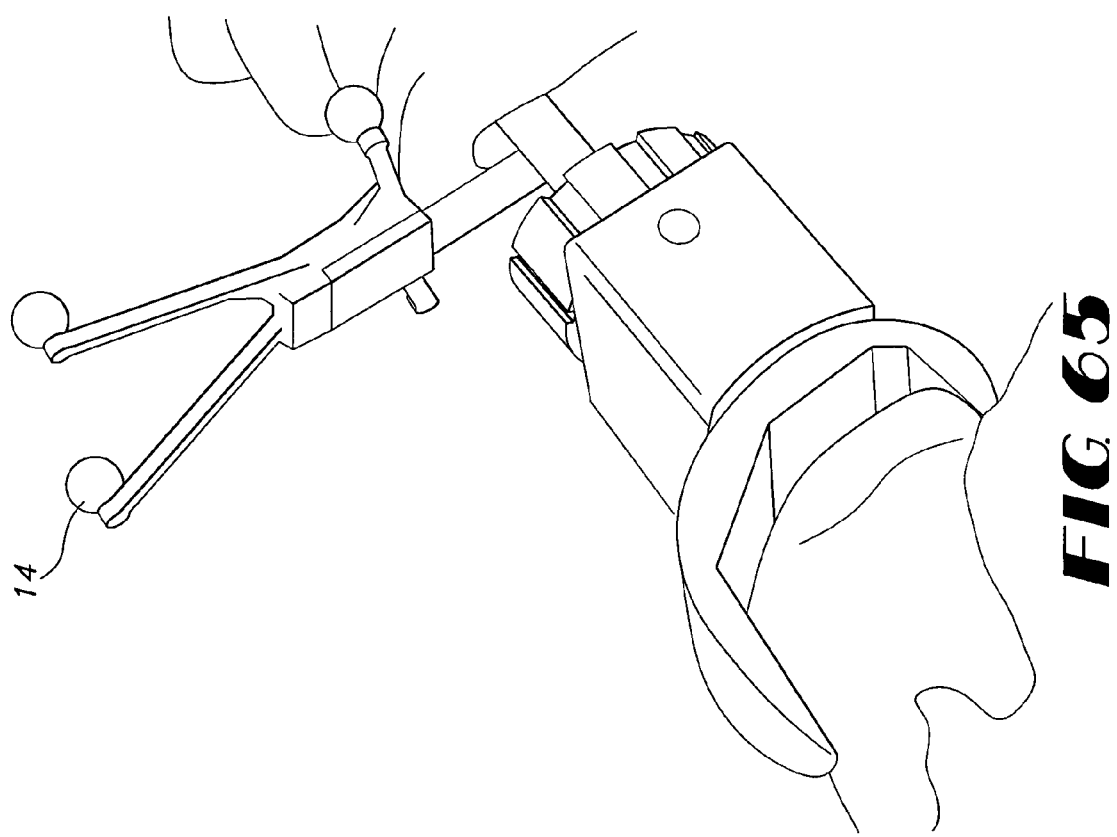
FIG. 65 is a view showing navigation and placement of a femoral component using an impactor to which a fiducial according to one embodiment of the present invention is attached.

FIGS. 63 and 64 show femoral component and tibial component overlays, respectively, according to certain position and orientation of cutting blocks/instrumentation as resecting is being done. The surgeon can thus visualize where the implant components will be and can assess fit, and other things if desired, before resections are made.

Navigation, Placement and Assessment of Trials and Implants

Once resection and modification of bone has been accomplished, implant trials can then be installed and tracked by the system in a manner similar to navigating and positioning the instrumentation, as displayed on the screen 24. Thus, a femoral component trial, a tibial plateau trial, and a bearing plate trial may be placed as navigated on screen using computer generated overlays corresponding to the trials.

During the trial installation process, and also during the implant component installation process, instrument positioning process or at any other desired point in surgical or other operations according to the present invention, the system can transition or segue from tracking a component according to a first fiducial to tracking the component according to a second fiducial. Thus, as shown as FIG. 36, the trial femoral component is mounted on an impactor to which is attached a fiducial 14. The trial component is installed and positioned using the impactor. The computer 18 "knows" the position and orientation of the trial relative to the fiducial on the impactor (such as by prior registration of the component attached to the impactor) so that it can generate and display the image of the femoral component trial on screen 24 overlaid on the fluoroscopic image of the condylar component. At any desired point in time, before, during or after the trial component is properly placed on the condylar component of the femur to align with mechanical axis and according to proper orientation relative to other axes, the system can be instructed by foot pedal or otherwise to begin tracking the position of the trial component using the fiducial attached to the femur rather than the one attached to the impactor. According to the preferred embodiment, the sensor 16 "sees" at this point in time both the fiducials on the impactor and the femur 12 so that it already "knows" the position and orientation of the trial component relative to the fiducial on the impactor and is thus able to calculate and store for later use the position and orientation of the trial component relative to the femur 12 fiducial. Once this "handoff" happens, the impactor can be removed and the trial component tracked with the femur fiducial 14 as part of or moving in concert with the femur 12. Similar handoff procedures may be used in any other instance as desired in accordance with the present invention.

Figure 66:
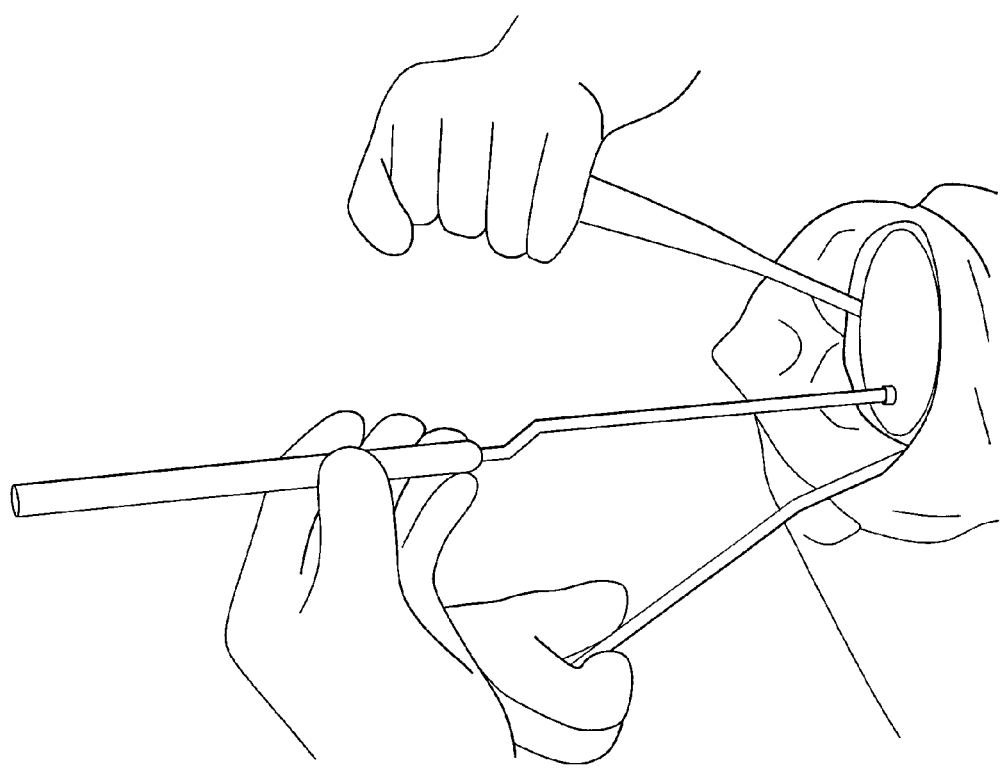
FIG. 66 is a view showing navigation and placement of a tibial trial component according to one embodiment of the present invention.

FIG. 66 shows the tibial plateau trial being tracked and installed in a manner similar to femoral component trial as discussed above. Alternatively, the tibial trial can be placed on the proximal tibia and then registered using the probe 26. Probe 26 is used to designate preferably at least three features on the tibial trial of known coordinates, such as bone spike holes. As the probe is placed onto each feature, the system is prompted to save that coordinate position so that the system can match the tibial trial's feature's coordinates to the saved coordinates. The system then tracks the tibial trial relative to the tibial anatomical reference frame.

Once the trial components are installed, the surgeon can assess alignment and stability of the components and the joint. During such assessment, in trial reduction, the computer can display on monitor 24 the relative motion between the trial components to allow the surgeon to make soft tissue releases and changes in order to improve the kinematics of the knee. The system can also apply rules and/or intelligence to make suggestions based on the information such as what soft tissue releases to make if the surgeon desires. The system can also display how the soft tissue releases are to be made.

Figure 67:
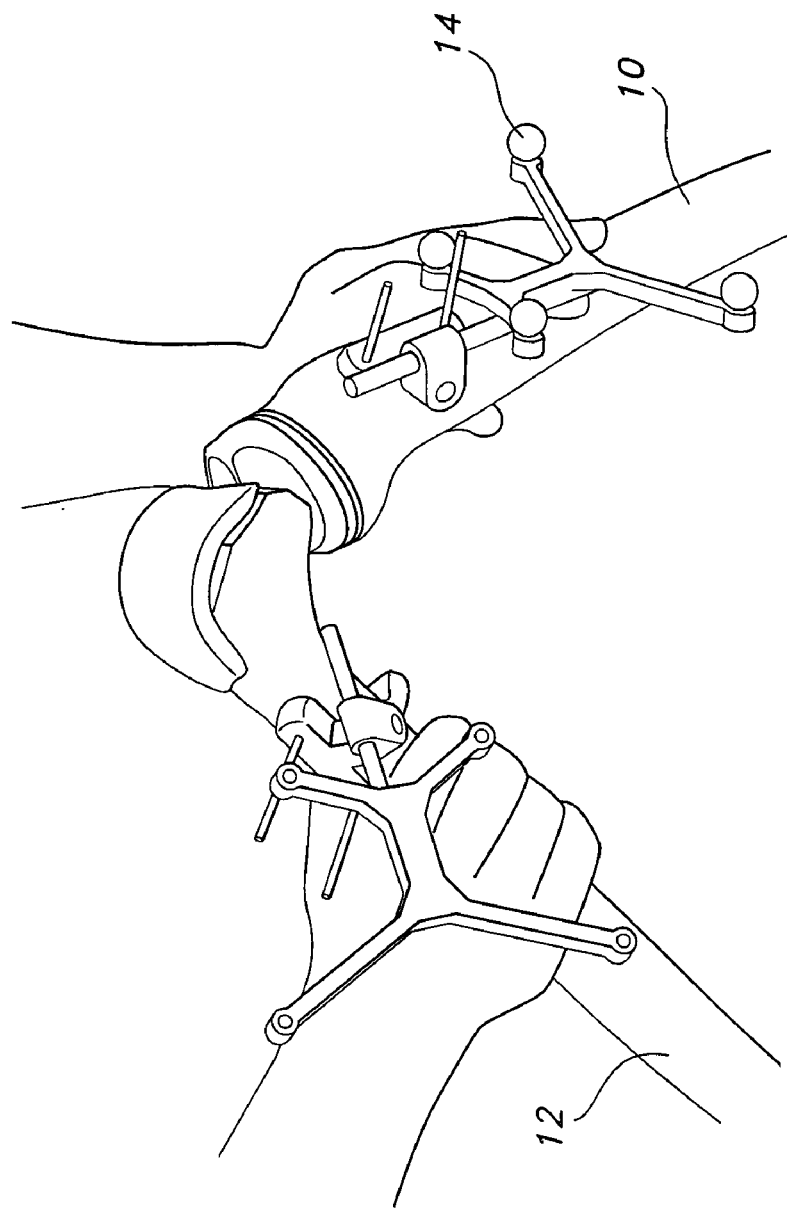
FIG. 67 is a view showing articulation of trial components during trial reduction according to one embodiment of the present invention.
Figure 68:
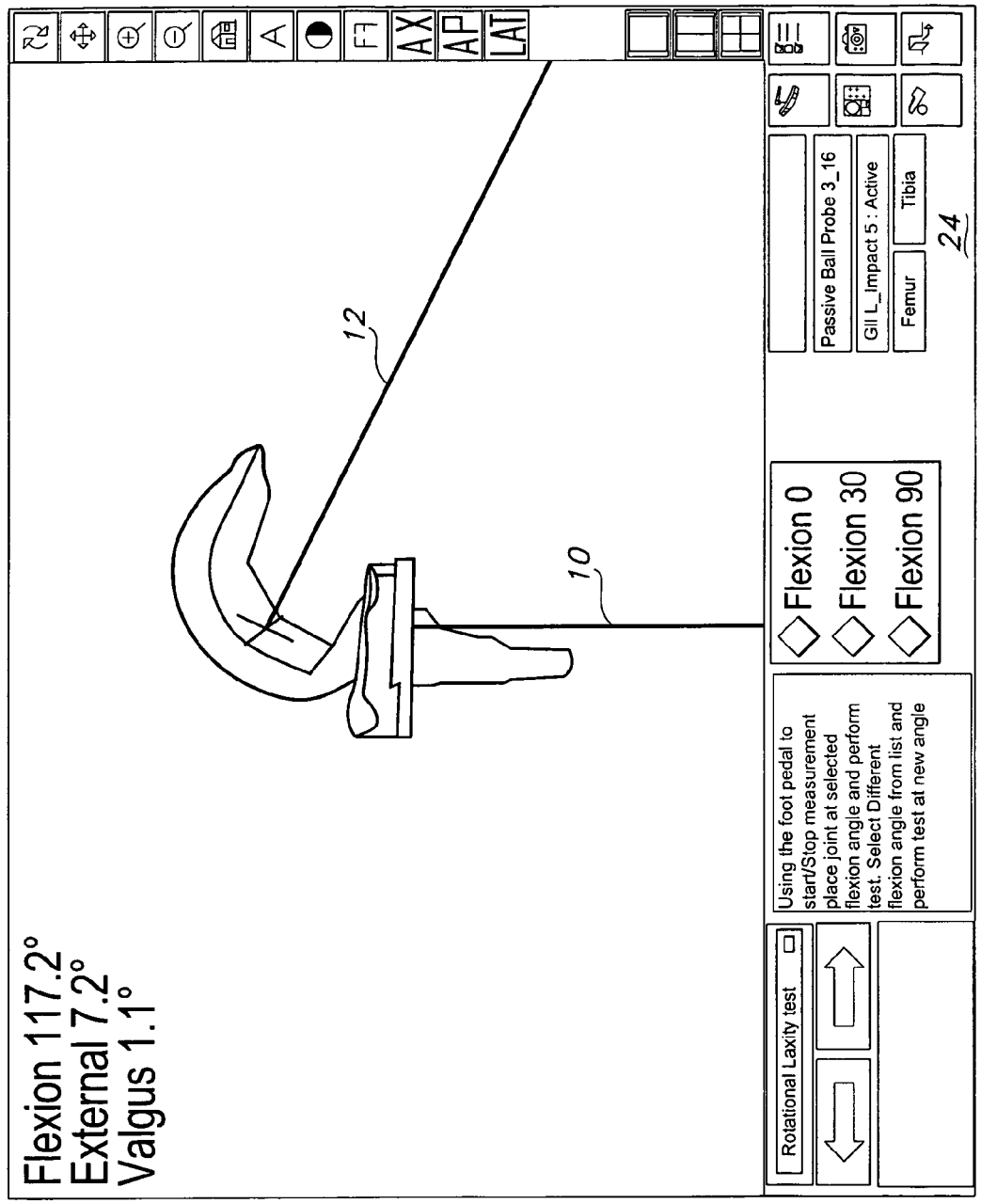
FIG. 68 is a screen face according to one embodiment of the present invention which may be used to assist in assessing joint function.
Figure 69:
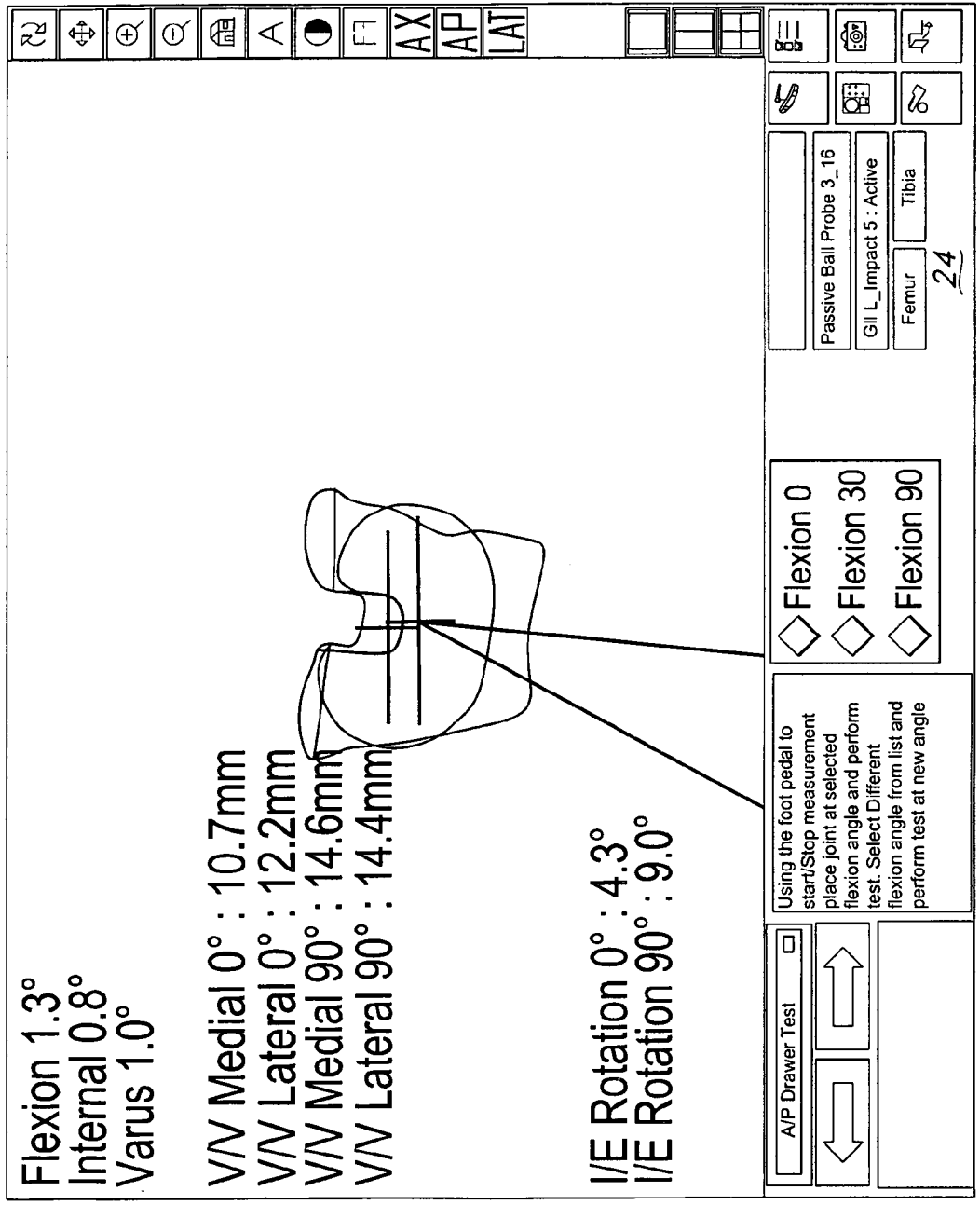
FIG. 69 is a screen face according to one embodiment of the present invention which may be used to assist in assessing joint function.
Figure 70:
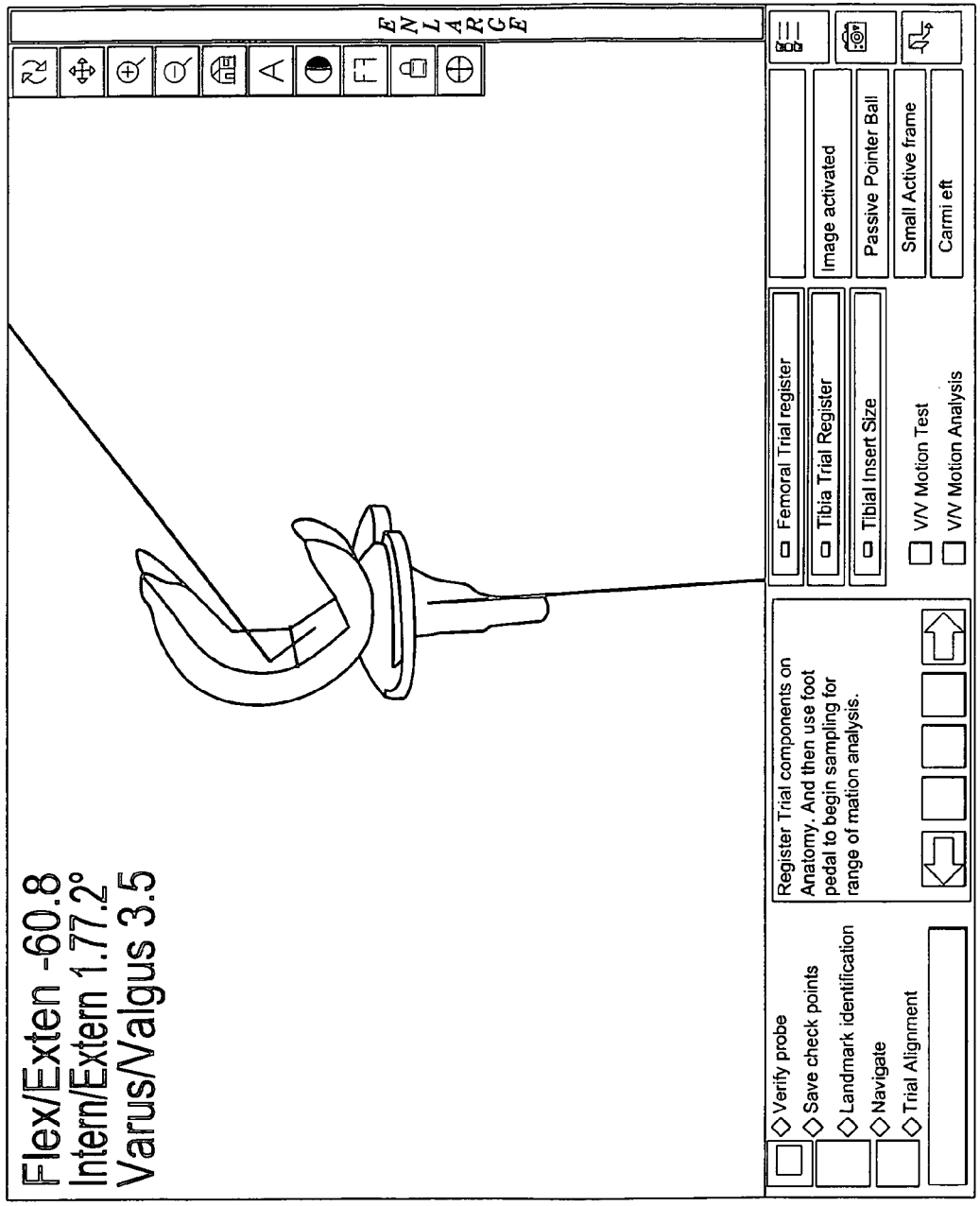
FIG. 70 is a screen face according to one embodiment of the present invention which may be used to assist in assessing joint function.
Figure 71:
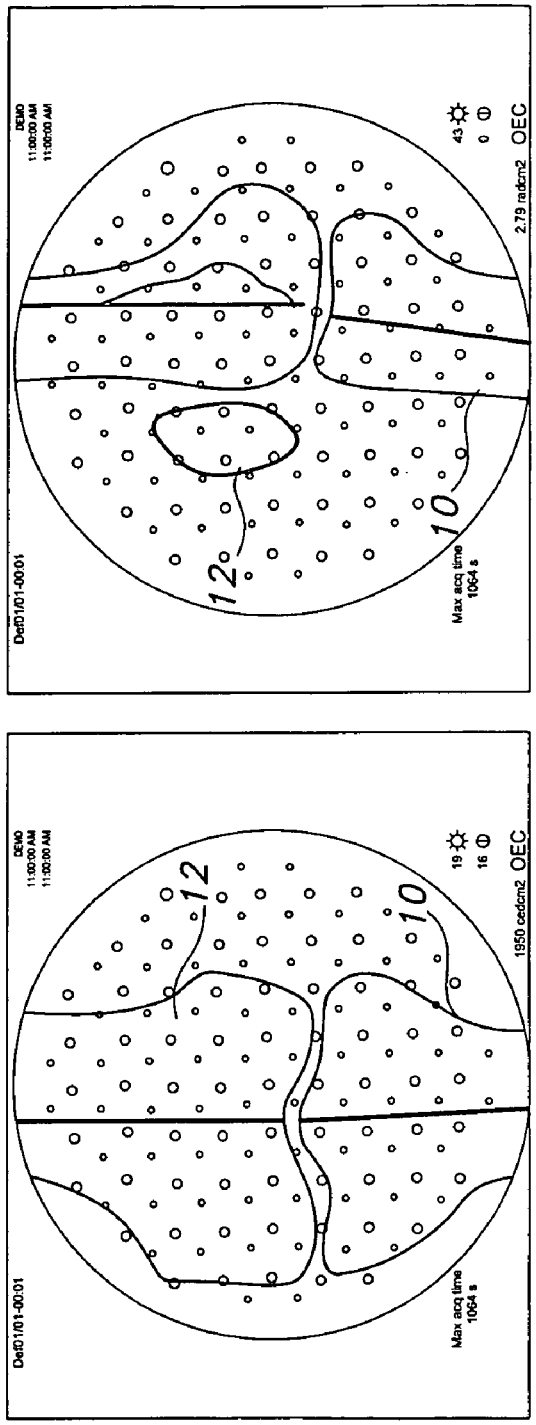
FIG. 71 is a screen face according to one embodiment of the present invention which contains images and textural suggestions for assisting in assessing performance and making adjustments to improve performance of a joint in accordance with one aspect of the invention.
Figure 73:
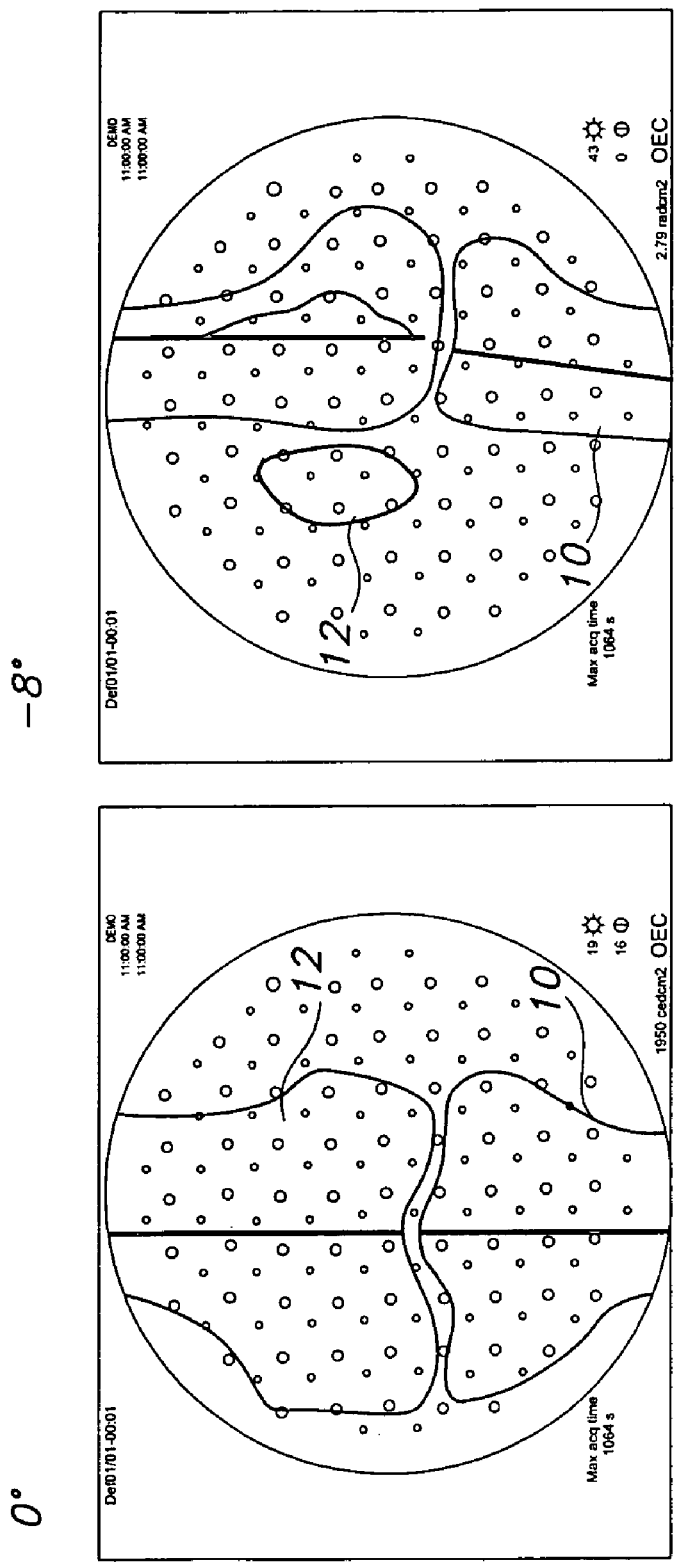
FIG. 73 is a screen face according to one embodiment of the present invention which contains images and textural suggestions for assisting in assessing performance and making adjustments to improve performance of a joint in accordance with one aspect of the invention.
Figure 74:
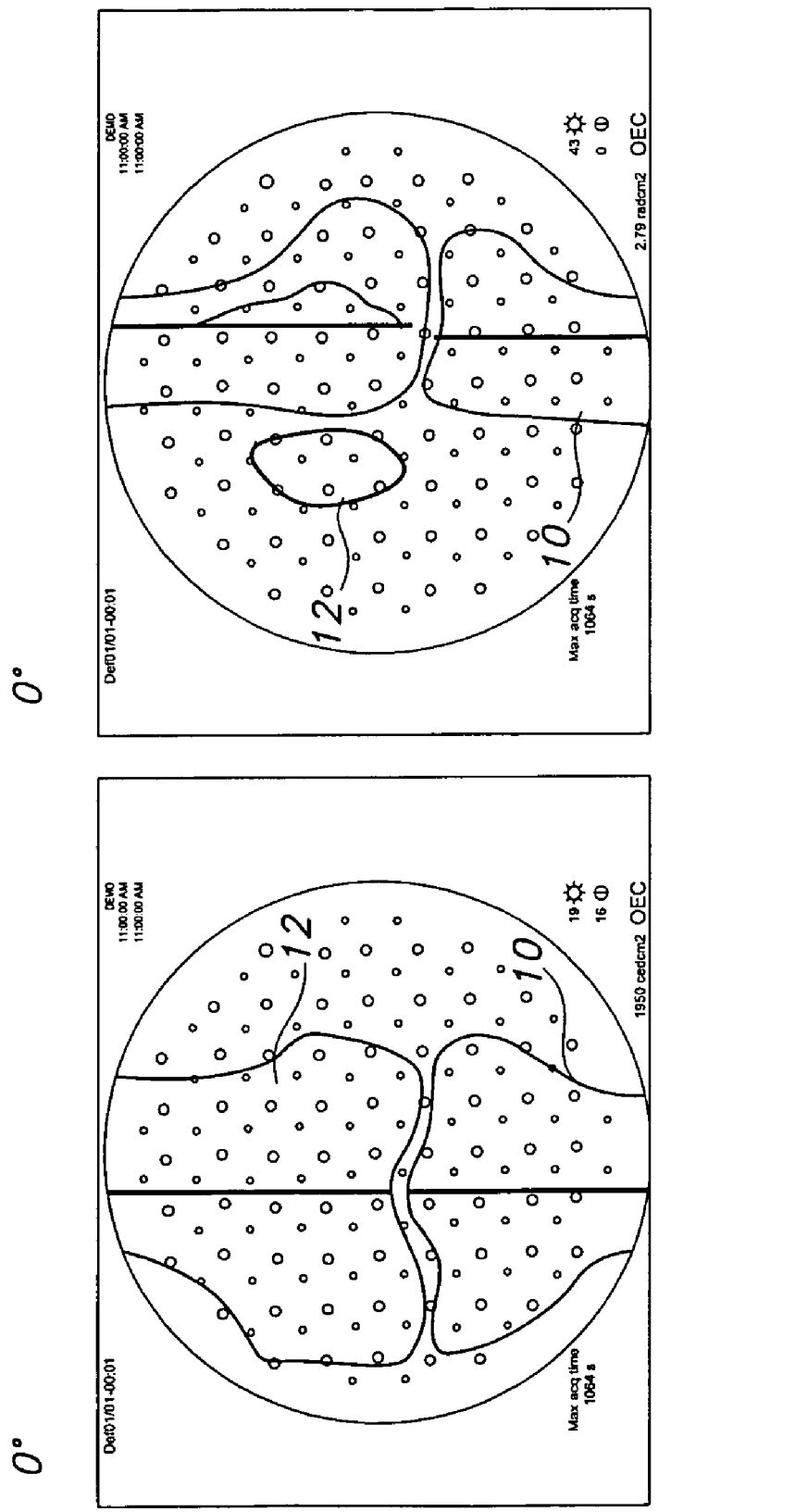
FIG. 74 is a screen face according to one embodiment of the present invention which contains images and textural suggestions for assisting in assessing performance and making adjustments to improve performance of a joint in accordance with one aspect of the invention.

FIG. 67 shows the surgeon articulating the knee as he monitors the screen which is presenting images such as those shown in FIGS. 68–70 which not only show movement of the trial components relative to each other, but also orientation, flexion, and varus/valgus. During this assessment, the surgeon may conduct certain assessment processes such as external/internal rotation or rotary laxity testing, varus/valgus tests, and anterior-posterior drawer at 0 and 90 degrees and mid range. Thus, in the AP drawer test, the surgeon can position the tibia at the first location and press the foot pedal. He then positions the tibia at the second location and once again presses the foot pedal so that the computer has registered and stored two locations in order to calculate and display the drawer and whether it is acceptable for the patient and the product involved. If not, the computer can apply rules in order to generate and display suggestions for releasing ligaments or other tissue, or using other component sizes or types, such as shown, for example, in FIGS. 71–74. Once the proper tissue releases have been made, if necessary, and alignment and stability are acceptable as noted quantitatively on screen about all axes, the trial components may be removed and actual components navigated, installed, and assessed in performance in a manner similar to that in which the trial components were navigated, installed, and assessed.

FIG. 75 is another computer generated 3-dimensional image of the trial components as tracked by the system during trialing.

At the end of the case, all alignment information can be saved for the patient file. This is of great assistance to the surgeon due to the fact that the outcome of implant positioning can be seen before any resectioning has been done on the bone. The system is also capable of tracking the patella and resulting placement of cutting guides and the patellar trial position. The system then tracks alignment of the patella with the patellar femoral groove and will give feedback on issues, such as, patellar tilt.

The tracking and image information provided by instrumentation, systems, and processes according to the present invention facilitate telemedical techniques, because they provide useful images for distribution to distant geographic locations where expert surgical or medical specialists may collaborate during surgery. Thus, instrumentation, systems, and processes according to the present invention can be used in connection with computing functionality 18 which is networked or otherwise in communication with computing functionality in other locations, whether by PSTN, information exchange infrastructures such as packet switched networks including the Internet, or as otherwise desire. Such remote imaging may occur on computers, wireless devices, videoconferencing devices or in any other mode or on any other platform which is now or may in the future be capable of rending images or parts of them produced in accordance with the present invention. Parallel communication links such as switched or unswitched telephone call connections may also accompany or form part of such telemedical techniques. Distant databases such as online catalogs of implant suppliers or prosthetics buyers or distributors may form part of or be networked with functionality 18 to give the surgeon in real time access to additional options for implants which could be procured and used during the surgical operation.

What is claimed is:

1. Apparatus for adjustably positioning surgical instrumentation relative to a femur or a tibia, comprising:
   a. a structural member adapted to fasten to the femur or the tibia;
   b. instrumentation adapted to guide a resection device employed to resect bone from the femur or the tibia;
   c. an alignment module connecting the structural member and the instrumentation, comprising:
      i. a first member connected to the instrumentation;
      ii. a second member connected to the structural member and connected to the first member in a fashion that allows the second member and the first member to be varied in orientation relative to each other about at least two substantially orthogonal axes;
      iii. adjustment structure for controlling motion of the second member relative to the first member and for fixing the position of the second member relative to the first member; and
   d. a fiducial connected at least indirectly to the instrumentation, which fiducial is capable of being tracked in position and orientation in at least three dimensions by a surgical navigation system.

2. Apparatus according to claim 1 further comprising an intermediate member connected to the first member in a fashion that allows the intermediate member to move with at least one degree of freedom relative to the first member; and also connected to the second member in a fashion that allows the intermediate member to move with at least one degree of freedom relative to the second member.

3. Apparatus according to claim 2 in which the first and intermediate members are gimbals.

4. Apparatus according to claim 2 in which the intermediate and second members are gimbals.

5. Apparatus according to claim 1 in which the structural member is an external fixation device.

6. Apparatus according to claim 1 in which the structural member cooperates with the instrumentation via a ball and socket linkage.

7. Apparatus for adjustably positioning surgical instrumentation relative to bone, comprising:
  a. a structural member adapted to fasten to bone;
  b. surgical instrumentation adapted to guide surgical devices; and
  c. an alignment module, comprising:
    i. a structural member retention component adapted to connect to the structural member;
    ii. a surgical instrumentation retention component adapted to connect to the surgical instrumentation; and
    iii. an intermediate component adapted to connect to the structural member retention component in a fashion that allows the structural member retention component and the intermediate component to rotate relative to each other about at least one axis, and adapted to connect to the surgical instrumentation retention component in a fashion that allows the surgical instrumentation retention component and the intermediate component to rotate relative to each other about at least one axis two axes;
    iv. an adjustment mechanism connecting the intermediate component and the structural member retention component, the adjustment mechanism adapted to control and fix orientation of the intermediate component relative to the structural member retention component; and
    v. an adjustment mechanism connecting the intermediate component and the surgical instrumentation retention component, the adjustment mechanism adapted to control and fix orientation of the intermediate component and the surgical instrumentation retention component;
  wherein at least one of the adjustment mechanisms is a worm gear and follower mechanism.

8. Apparatus according to claim 7 in which the surgical instrumentation retention component and the intermediate component are gimbals.

9. Apparatus according to claim 7 in which the structural member retention component and the intermediate component are gimbals.

10. Apparatus according to claim 7 in which the structural member is an extramedullary rod.

11. Apparatus according to claim 7 further comprising at least one fiducial connected at least indirectly to the instrumentation for tracking the instrumentation in a surgical navigation system.

12. A system for performing knee surgery comprising:
  (a) an imager for obtaining an image of at least portions of the knee joint, wherein the imager and at least one bone forming part of the knee joint are each attached to a fiducial capable of being tracked by a position sensor;
  (b) at least one position sensor adapted to track position of said fiducials;
  (c) a computer adapted to store at least one image of at least portions of the knee joint and to receive information from said at least one sensor in order to track position and orientation of said fiducials and thus the knee joint;
  (d) a rod adapted to be fastened to bone in the vicinity of the knee joint;
  (e) surgical instrumentation adapted to guide devices adapted to cut bone in the vicinity of the knee joint;
  (f) a variable alignment module connecting the rod and the surgical instrumentation, and adapted to allow adjustment and fixation of angular orientation of the surgical instrumentation relative to the rod about at least two axes;
  (g) a fiducial at least indirectly connected to the surgical instrumentation in order to allow position and orientation of the instrumentation to be tracked by the system; and
  (h) a monitor adapted to receive information from the computer in order to display at least one image of the surgical instrumentation, positioned and oriented relative to the knee joint for navigation and positioning of the surgical instrumentation relative to the knee joint.

13. Apparatus for adjustably positioning surgical instrumentation relative to bone, comprising:
  a. a structural member adapted to fasten to bone;
  b. surgical instrumentation adapted to guide surgical devices; and
  c. an alignment module, comprising:
    i. a structural member retention component adapted to connect to the structural member;
    ii. a surgical instrumentation retention component adapted to connect to the surgical instrumentation; and
    iii. an intermediate component adapted to connect to the structural member retention component in a fashion that allows the structural member retention component and the intermediate component to rotate relative to each other about at least one axis, and adapted to connect to the surgical instrumentation retention component in a fashion that allows the surgical instrumentation retention component and the intermediate component to rotate relative to each other about at least one axis two axes;
    iv. an adjustment mechanism connecting the intermediate component and the structural member retention component, the adjustment mechanism adapted to control and fix orientation of the intermediate component relative to the structural member retention component; and
    v. an adjustment mechanism connecting the intermediate component and the surgical instrumentation retention component, the adjustment mechanism adapted to control and fix orientation of the intermediate component and the surgical instrumentation retention component;
wherein the structural member is an extramedullary or an intramedullary rod.

14. Apparatus according to claim 13 in which the surgical instrumentation retention component and the intermediate component are gimbals.

15. Apparatus according to claim 13 in which the structural member retention component and the intermediate component are gimbals.

16. Apparatus according to claim 13 in which at least one of the adjustment mechanisms is a worm gear and follower mechanism.

17. An adjustment apparatus for adjustably positioning surgical instrumentation relative to a femur, comprising:
 a. an index member adapted to be secured to the femur, said index member having a longitudinal axis, wherein the index member is an intramedullary or an extramedullary rod;
 b. a cutting guide adapted to assist in guidance of a resection device employed to resect bone from said femur; and
 c. an alignment module, comprising:
  i. an index member retention structure adapted to connect to the index member;
  ii. a cutting guide retention structure adapted to connect to the cutting guide; and
  iii. an intermediate adjustment structure coupling the index member retention structure and the cutting guide retention structure, the intermediate structure permitting the cutting guide retention structure to be adjusted and fixed in place in an infinite number of positions throughout at least the following ranges;
 a first rotational range relative to the index member,
 a first translational range relative to the index member;
wherein the intermediate adjustment structure couples the index member retention structure and the cutting guide retention structure via at least one of a ball an socket mechanism, a gimbal, or a worm gear and follower mechanism.

18. An adjustment apparatus for adjustably positioning surgical instrumentation relative to a femur, comprising:
 a. an index member adapted to be secured to the femur, said index member having a longitudinal axis;
 b. a cutting guide adapted to assist in guidance of a resection device employed to resect bone from said femur; and
 c. an alignment module, comprising:
  i. an index member retention structure adapted to connect to the index member;
  ii. a cutting guide retention structure adapted to connect to the cutting guide; and
  iii. an intermediate adjustment structure coupling the index member retention structure and the cutting guide retention structure, the intermediate structure permitting the cutting guide retention structure to be adjusted and fixed in place in an infinite number of positions throughout at least the following ranges;
 a first rotational range relative to the index member, wherein the first rotational range is about the longitudinal axis of the index member;
 a first translational range relative to the index member;
wherein the intermediate adjustment structure couples the index member retention structure and the cutting guide retention structure via at least one of a ball an socket mechanism, a gimbal, or a worm gear and follower mechanism.

19. The adjustment apparatus of claim 18, wherein the intermediate structure further permits the cutting guide retention structure to be adjusted and fixed in place in an infinite number of positions throughout a second rotational range.

20. The adjustment apparatus of claim 19, wherein the second rotational range is perpendicular to the longitudinal axis of the index member.

21. The adjustment apparatus of claim 19, wherein the intermediate structure further permits the cutting guide retention structure to be adjusted and fixed in place in an infinite number of positions throughout a third rotational range.

22. The adjustment apparatus of claim 21, wherein the rotational range is perpendicular to the longitudinal axis of the index member.

* * * * *